US011466069B2

(12) United States Patent
Green et al.

(10) Patent No.: US 11,466,069 B2
(45) Date of Patent: Oct. 11, 2022

(54) METHODS OF TREATMENT AND NOVEL CONSTRUCTS

(71) Applicant: AUCKLAND UNISERVICES LIMITED, Auckland (NZ)

(72) Inventors: Colin Richard Green, Auckland (NZ); Frazer Paul Coutinho, Auckland (NZ); Ilva Dana Rupenthal, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 177 days.

(21) Appl. No.: 16/608,761

(22) PCT Filed: Apr. 30, 2018

(86) PCT No.: PCT/NZ2018/050059
§ 371 (c)(1),
(2) Date: Oct. 25, 2019

(87) PCT Pub. No.: WO2018/199777
PCT Pub. Date: Nov. 1, 2018

(65) Prior Publication Data
US 2021/0107963 A1    Apr. 15, 2021

(30) Foreign Application Priority Data

Apr. 28, 2017 (NZ) .................................... 731353
Apr. 28, 2017 (NZ) .................................... 731364

(51) Int. Cl.
| | | |
|---|---|---|
| C07K 14/705 | (2006.01) |
| A61P 27/02 | (2006.01) |
| A61P 9/00 | (2006.01) |
| A61P 35/00 | (2006.01) |
| A61K 38/00 | (2006.01) |
| C07K 14/005 | (2006.01) |

(52) U.S. Cl.
CPC ............ *C07K 14/705* (2013.01); *A61K 38/00* (2013.01); *A61P 9/00* (2018.01); *A61P 27/02* (2018.01); *A61P 35/00* (2018.01); *C07K 14/005* (2013.01); *C07K 2319/10* (2013.01); *C12N 2730/10122* (2013.01)

(58) Field of Classification Search
CPC ................ C07K 14/002; C07K 14/005; C07K 2319/00; A61K 38/00
See application file for complete search history.

(56) References Cited

U.S. PATENT DOCUMENTS

| | | |
|---|---|---|
| 3,687,808 A | 8/1972 | Merigan et al. |
| 4,861,757 A | 8/1989 | Jensen et al. |
| 5,034,506 A | 7/1991 | Summerton et al. |
| 5,044,810 A | 9/1991 | Matsuoka et al. |
| 5,166,195 A | 11/1992 | Matsuoka et al. |
| 5,998,148 A | 12/1999 | Mukherjee et al. |
| 6,458,590 B1 | 10/2002 | Mukherjee et al. |
| 6,506,559 B1 | 1/2003 | Fire et al. |
| 6,752,987 B1 | 6/2004 | Lauermann |
| 7,098,190 B1 | 8/2006 | Becker et al. |
| 7,153,822 B2 | 12/2006 | Jensen et al. |
| 7,521,191 B2 | 4/2009 | Khvorova et al. |
| 7,615,540 B2 | 11/2009 | Green et al. |
| 7,879,811 B2 | 2/2011 | Green et al. |
| 7,902,164 B2 | 3/2011 | Becker et al. |
| 7,919,474 B2 | 4/2011 | Green et al. |
| 8,034,789 B2 | 10/2011 | Laux et al. |
| 8,063,023 B2 | 11/2011 | Becker et al. |
| 8,247,384 B2 | 8/2012 | Green et al. |
| 8,314,074 B2 | 11/2012 | Becker et al. |
| 8,685,940 B2 | 4/2014 | Becker et al. |
| 8,815,819 B2 | 8/2014 | Laux et al. |
| 8,975,237 B2 | 3/2015 | Becker et al. |
| 9,035,037 B2 | 5/2015 | Becker et al. |
| 2003/0105165 A1 | 6/2003 | Griffith |
| 2003/0148968 A1 | 8/2003 | Hammond et al. |
| 2003/0215424 A1 | 11/2003 | Khvorova et al. |
| 2004/0092429 A1 | 5/2004 | Seul et al. |
| 2004/0259768 A1 | 12/2004 | Hammond |
| 2005/0119211 A1 | 6/2005 | Jensen et al. |
| 2006/0105013 A1 | 5/2006 | Chowrira et al. |
| 2007/0037765 A1 | 2/2007 | Becker et al. |
| 2007/0066555 A1 | 3/2007 | Becker et al. |
| 2007/0072819 A1 | 3/2007 | Becker et al. |
| 2007/0232526 A1 | 10/2007 | Ashkar et al. |
| 2008/0249041 A1 | 10/2008 | Becker et al. |
| 2008/0261867 A1 | 10/2008 | Klagsbrun et al. |
| 2010/0150877 A1 | 6/2010 | O'Brien et al. |
| 2010/0279921 A1 | 11/2010 | Duft |

(Continued)

FOREIGN PATENT DOCUMENTS

| | | |
|---|---|---|
| EP | 1 514 929 A1 | 3/2005 |
| JP | 2002-535377 A | 10/2002 |
| JP | 2003-238441 A | 8/2003 |
| WO | WO 91/09958 A2 | 7/1991 |
| WO | WO 1994/012633 | 6/1994 |

(Continued)

OTHER PUBLICATIONS

Extended European Search Report in EP Application No. 18790692.0, dated Dec. 11, 2020, in 12 pages.

(Continued)

*Primary Examiner* — Karen Cochrane Carlson
(74) *Attorney, Agent, or Firm* — Duane Morris LLP

(57) ABSTRACT

The present invention provides novels method of targeting delivery of a compound to hypoxic cells, for example treatment of diseases and disorders associated with hypoxia, comprising administration of a construct comprising a targeting carrier peptide and a compound for delivery to a hypoxic cell. The invention also provides novel methods for the treatment of diseases or disorders of the eye by administration of a novel construct, a nucleic acid encoding a novel construct, and/or a nucleic acid vector comprising a nucleic acid encoding a novel construct. The invention further provides novel constructs, nucleic acids encoding such constructs, and/or nucleic acid vectors comprising nucleic acids encoding such constructs.

30 Claims, 15 Drawing Sheets

Figure 1:
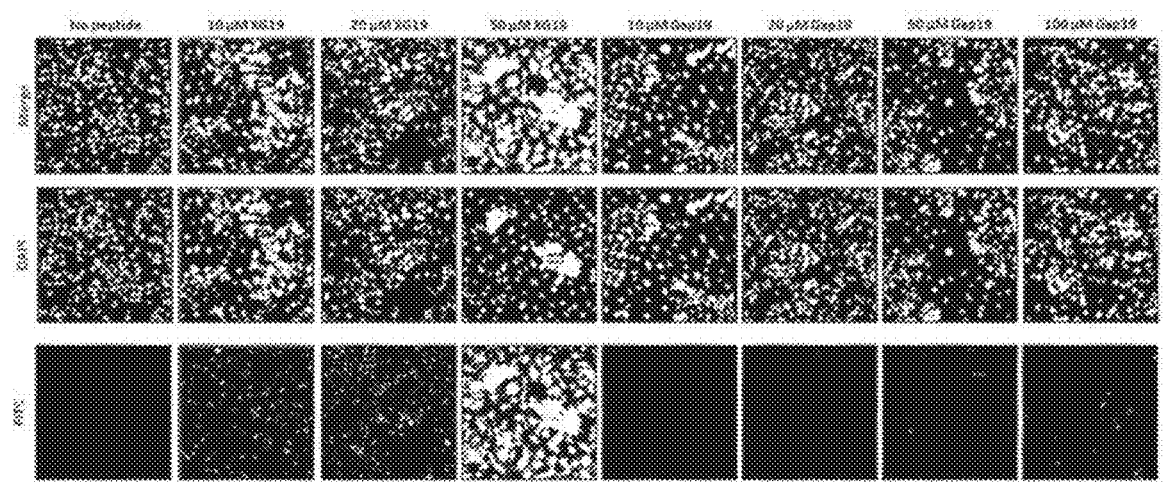

Specification includes a Sequence Listing.

(56) References Cited

U.S. PATENT DOCUMENTS

| | | |
|---|---|---|
| 2011/0038920 A1 | 2/2011 | Mori et al. |
| 2011/0092449 A1 | 4/2011 | Duft |
| 2011/0130710 A1 | 6/2011 | Becker et al. |
| 2011/0144182 A1 | 6/2011 | Becker et al. |
| 2011/0217313 A1 | 9/2011 | Becker et al. |
| 2011/0223204 A1 | 9/2011 | Duft et al. |
| 2011/0243964 A1 | 10/2011 | Duft |
| 2011/0245184 A1 | 10/2011 | Duft |
| 2011/0300130 A1 | 12/2011 | Becker et al. |
| 2013/0184220 A1 | 7/2013 | Duft |

FOREIGN PATENT DOCUMENTS

| | | |
|---|---|---|
| WO | WO 1998/024797 | 6/1998 |
| WO | WO 00/29427 A2 | 5/2000 |
| WO | WO 2000/044409 A1 | 8/2000 |
| WO | WO 01/13957 A2 | 3/2001 |
| WO | WO 2003/032964 A2 | 4/2003 |
| WO | WO 03/064459 A1 | 8/2003 |
| WO | WO 2003/063891 A1 | 8/2003 |
| WO | WO 2005/053600 A2 | 6/2005 |
| WO | WO 2005/119211 A1 | 12/2005 |
| WO | WO 2006/069181 A2 | 6/2006 |
| WO | WO 2006/134494 A2 | 5/2008 |
| WO | WO 2008/060622 A2 | 5/2008 |
| WO | WO 2008/073479 A2 | 6/2008 |
| WO | WO 2008/151022 A2 | 12/2008 |
| WO | WO 2009/075881 A2 | 6/2009 |
| WO | WO 2009/075882 A2 | 6/2009 |
| WO | WO 2009/085268 A2 | 7/2009 |
| WO | WO 2009/085269 A2 | 7/2009 |
| WO | WO 2009/085270 A2 | 7/2009 |
| WO | WO 2009/085271 A2 | 7/2009 |
| WO | WO 2009/085272 A2 | 7/2009 |
| WO | WO 2009/085273 A2 | 7/2009 |
| WO | WO 2009/085274 A2 | 7/2009 |
| WO | WO 2009/085275 A2 | 7/2009 |
| WO | WO 2009/085277 A2 | 7/2009 |
| WO | WO 2009/148613 A1 | 12/2009 |
| WO | WO 2011/155853 A1 | 12/2011 |
| WO | WO 2013/165262 A1 | 11/2013 |
| WO | WO-2016/029191 A2 | 2/2016 |

OTHER PUBLICATIONS

Chen, Qing, et al. "Carcinoma-astrocyte gap junctions promote brain metastasis by cGAMP transfer." Nature 533.7604 (2016): 493-498.
A Chinese procedure involving stem cell transplants is providing some very interesting results. Oct. 24, 2003. Canadian Paraplegic Association. Sep. 27, 2006 http://www.canparaplegic.org/national/level12.tpl?var1=story&var2=20031024154627.
Abudara, V. et al., "The Connexin43 Mimetic Peptide Gap19 Inhibits Hemichannels Without Altering Gap Junctional Communication in Astrocytes", Frontiers in Cellular Neuroscience. 2014, vol. 8 (article 306), pp. 1-8.
Adwan, et al. "Downregulation of osteopontin and bone sialoprotein II is related to reduced colony formation and metastasis formation of MDA-MB-231 human breast cancer cells." Cancer Gene Therapy (2004) 11: p. 109-120: Nature Publishing Group.
Agrawal, ed., "Antisense Oligonucleotides, towards clinical trials." Protocols for Oligonucleotides and Analogs, Synthesis and Properties, TIBS, vol. 14(10), Human Press Inc., New Jersey, pp. 376-387; 1996.
Aguayo, A.J., et al. J. Exp. Biol. 95:231-240 (1981).
Ahmadi, et al. Int. Ophthalmol. Clinics, 42(3):13-22 (2002).
Aitken, et al. "Adenoviral Down-Regulation of Osteopontin Inhibits Human Osteoclast Differentiation In Vitro." Journal of Cellular Biochemistry (2004) 93: p. 896-903. Wiley-Liss, Inc.
Altschul S.F. J Mol Biol 215:403-10 (1990).
Altschul S.F. J Mol Evol 36:290-300 (1993).
Antisense Research and Applications (1993), CRC Press, Chps. 2, 19, 28, 32.
Aqil, Mohammed, et al. "Status of terpenes as skin penetration enhancers." Drug Discovery Today 12.23-24 (2007): 1061-1067.
Aramaki, Yukihiko, et al. "Intradermal delivery of antisense oligonucleotides by the pulse depolarization iontophoretic system." Biological and Pharmaceutical Bulletin 26.10 (2003): 1461-1466.
Arnold, et al., Seminars in Ophthalmology 17:39-46 (2002).
Ashcroft, et al. Nat Cell Biol. 1:260-6 (1999).
Baker, D.W. et al., "ACC/AHA Guidelines for the Evaluation and Management of Chronic Heart Failure in the Adult." 2001 American College of Cardiology and the American Heart Association.
Baldwin, Heather C., et al., "Growth factors in corneal wound healing following refractive surgery: A Review" ACTA Ophthalmologica Scandinavica 80(3):2002-06 (Jun. 2002).
Barany and Merrifield, "The Peptides," eds. E. Gross and F. Meienhofer, vol. 2 (Academic Press, 1980) pp. 3-285.
Bashyam, Hema. "Scar-free healing." (Jan. 7, 2008) JEM 205(1): p. 2-3.
BBC News "Gels "heal wounds more quickly""; http://news.bbc.co.uk/1/hi/health/3243633.stm. (May 26, 2006).
Beaucage et al., eds., Current Protocols in Nucleic Acid Chemistry John Wiley & Sons, Inc., New York, 2000.
Becker DL, Green CR (2001) Gap junction-mediated interactions between cells. Chapter 3 in Cell-Cell Interactions—A Practical Approach ed. TP Fleming. Oxford University Press, pp. 47-70.
Becker, D.L. and Davies, C.S. (1995) The role of gap junctions in the development of the preimplantation mouse embryo. In Microscopy of Intercellular Communicating Junctions. Ed. R. Gourdie. Microsc. Res. Tech. 31, 364-374.
Becker, D.L. and Mobbs, P. (1999) Connexin alpha1 and cell proliferation in the developing chick retina. Expl. Neurol. 156(2): 326-332.
Becker, D.L., Bonness, V., and Mobbs, P. (1998) Cell coupling in the retina: Patterns and purpose. Cell Biol. Int. 22, 781-792.
Becker, D.L., Bonness, V., Catsicas, M. and Mobbs, P. (2002) Changing patterns of ganglion cell coupling and connexin expression during chick retinal development. J. Neurobiol. 52, 280-293.
Becker, D.L., Ciantar, D., Catsicas, M., Pearson, R. and Mobbs, P. (2001) Use of pIRES vectors to express EGFP and connexin constructs in studies of the role of gap junctional communication in the early development of the chick retina and brain. Cell Commun. Adhes. 8, 355-359.
Becker, D.L., Cook, J.E., Davies, C.S., Evans, W.H. and Gourdie, R. (1998) Expression of major gap junction connexin types in the working myocardium of eight chordates. Cell Biol. Int. 22, 527-543.
Becker, D.L., David-Leclerc, C. and Warner A.E. (1992) The relationship of gap junctions and compaction in the preimplantation mouse embryo. Development Suppl., 113-118.
Becker, D.L., Evans, W.H., Green C.R. and Warner, A.E. (1995) Functional analysis of amino acid sequences in connexin 43 involved in intercellular communication through gap junctions. J. Cell Sci. 108, 1455-1467.
Becker, D.L., Evans, W.H., Green C.R. and Warner, A.E. (1995) Functional block of gap junctional communication using antipeptide antibodies: Molecular localization of the putative binding sites. Intercellular communication through gap junctions: Ed. Y. Kanno. Progress in Cell Research, 4; 427-430.
Becker, D.L., Lin, J.S. and Green G.R. (1999) Pluronic gel as a means of antisense delivery. In Antisense techniques in the CNS. A practical approach. Eds. R. Leslie, A.J. Hunter and H.A. Robertson, pp. 149-157.
Becker, D.L., McGonnell, I., Makarenkova, H., Patel, K., Tickle, C., Lorimer, J., and Green, C.R. (1999) Roles for alpha-1 connexin in morphogenesis of chick embryos using a novel antisense approach. Dev. Genetics. 24, 33-42.
Beeley N., Trends Biotechnol. Jun;12(6): 213-6 (1994).
Behrend, et. al. "Reduced Malignancy of ras-transformed NIH 3T3 Cells Expressing Antisense Osteopontin RNA." Cancer Research (Feb. 1, 1994) 54: p. 832-837.
Bennett MV, Zukin RS. Electrical coupling and neuronal synchronization in the Mammalian brain. Neuron. Feb. 19, 2004; 41(4):495-511.

(56) References Cited

OTHER PUBLICATIONS

Berge, et al., J. of Pharma Sci. 66, 1-19 (1977).
Berkovitz, B.K.B. and Becker, D.L. (2003) The detailed morphology and distribution of gap junction protein associated with cells from the intra-articular disc of the rat temporomandibular joint. Conn. Tiss. Res. 44, 12-18.
Bernstein, et. al. Invest Ophthalmol Vis Sci 44:4153-4162 (2003).
Berthoud, V.M. and Seul, K.H., Am J. Physiol. Jung Cell Mol. Physiol. 279:L619-L622 (2000).
Bioconjugate Techniques (Greg T. Hermanson, ed., Academic Press, 1996), Chapter 2 and 17.
Bittman, K. , Becker, D.L., Cicirata, F. and Parnavelas, J.G. (2002) Connexin expression in homotypic and heterotypic cell coupling in the developing cerebral cortex. J. Compo Neurol 443, 201-212.
Blackburn JP, Connat JL, Severs NJ, Green CR. Connexin43 gap junction levels during development of the thoracic aorta are temporally correlated with elastic laminae deposition and increased blood pressure. Cell Biol Int. Feb. 1997;21(2):87-97. PMID: 9080656 [PubMed—indexed for MEDLINE.
Blackburn JP, Peters NS, Yeh HI, Rothery S, Green CR, Severs NJ. Upregulation of connexin43 gap junctions during early stages of human coronary atherosclerosis. Arterioscler Thromb Vasc Biol. Aug. 1995;15(8):1219-28. PMID: 7627716 [PubMed—indexed for MEDLINE].
Boitano S. and Evans W., Am J Physiol Lung Cell Mol Physiol 279:L623-L630 (2000).
Bork et al. Go hunting in sequence databases but watch out for the traps. Trends in Genetics. 12(10): 425-427, 1996.
Bork, A. Powers and pitfalls in sequence analysis: the 70% hurdle. Genome Res 10: 398-400, 2000.
Braasch, D.A. and Corey, D.R., Biochemistry 41, 4503-4510 (2002).
Braet, K., et al., "Pharmacological senstivity of ATP release triggered by photoliberation of inositol-1,4,5-triphosphate and zero extracellular calcium in brain endothelial cells," Journal of Cellular Physiology, 197(2):205-213 (2003).
Branch, A.D. Hepatology 24, 1517-1529 (1996).
Branch, et. al. "A good antisense molecule is hard to find." TIBS (Feb. 1998) 23: p. 45-50. Elsevier Science Ltd.
Brandner, et. al., "Connexins 26, 30, and 43: Differences Among Spontaneous, Chronic, and Accelerated Human Wound Healing." J. Invest Dermatol. 122:1310-20 (2004).
Brenner, S.E. Errors in genome function. Trends in Genetics 15(4): 132-133, 1999.
Browne, George W., and C. S. Pitchumoni. "Pathophysiology of pulmonary complications of acute pancreatitis." World Journal of Gastroenterology 12.44 (2006): 7087-7096.
Brummelkamp T., et al., Science 296:550-553 (2002).
Brunton. Chapter 38. In: Goodman & Gilman's The Pharmacological Basis of Therapeutics, 9th Ed. (1996).
Brysch, W. Antisense Technology in the Ventral Nervous System, ed. H.A. Robertson; Oxford University Press, pp. 21-41 (1999).
Buono, et. al. Survey of Ophthalmology 50:15-26 (2005).
Buur, et al. J. Control Rel. 14:43-51 (1990).
Cairns, et al. Nat. Biotech 17:480-486 (1999).
Camelliti P, Devlin GP, Matthews KG, Kohl P, Green CR. Spatially and temporally distinct expression of fibroblast connexins after sheep ventricular infarction. Cardiovasc Res. May 1, 2004;62(2):415-25. PMID: 15094361 [PubMed—indexed for MEDLINE].
Camelliti P, Green CR, Kohl P. Structural and functional coupling of cardiac myocytes and fibroblasts. Adv Cardiol. 2006;42:132-49. Review. PMID: 16646588 [PubMed—indexed for MEDLINE].
Caplen N. et al., Proc Natl Acad Sci 98:9742-9747 (2001).
Cech, Biotechnology 13:323 (1995) Group I Introns: New Molecular Mechanisms for MRNA repair.
Celetti, et. al. "Overexpression of the Cytokine Osteopontin Identifies Aggressive Laryngeal Squamous Cell Carcinomas and Enhances Carcinoma Cell Proliferation and Invasiveness." (2005) Clinical Cancer Res 11(22): p. 8019-8027. AACR Journals.
Chakraborti, S. and Banerjea, A.C., Mol. Ther. 7, 817-826 (2003).

Chen Y-S, Green CR, Teague R, Perrett J, Danesh-Meyer HV, Toth I, Rupenthal ID. Intravitreal injection of lipoamino acid modified Connexin43 mimetic peptide enhances neuroprotection after retinal ischemia. Drug Deliv Transl Res. 2015; 5:480-488.
Chen Y-S, Green CR, Wang K, Danesh-Meyer HV and Rupenthal ID. Sustained intravitreal delivery of connexin43 mimetic peptide by poly(D,L-lactide-co-glycolide) acid micro- and nanoparticles—Closing the gap in retinal ischaemia. European Journal of Pharmaceutics and Biopharmaceutics. 2015. 95(Pt B):378-386.
Chen YS, Toth I, Danesh-Meyer HV, Green CR and Rupenthal ID. Cytotoxicity and vitreous stability of chemically modified connexin43 mimetic peptides for the treatment of optic neuropathy. Journal of Pharmaceutical Science. 2013; 102:2322-2331.
Cheng et al., J. Biol. Chem. 263:15110-15117 No. 29, (Oct. 15, 1988).
Cheng, H., et al. Science 273:510-513 (1996).
Chonn, et al., Current Op. Biotech. 6, 698-708 (1995).
Chou, et al. Ad. Enzyme Reg. 22:27-55 (1984).
Coffey KL, Krushinsky A, Green CR, Donaldson PJ. Molecular profiling and cellular localization of connexin isoforms in the rat ciliary epithelium. Exp Eye Res. Jul. 2002;75(1):9-21. PMID: 12123633 [PubMed—indexed for MEDLINE].
Collaborative Neuroscience the Spinal Cord Injury Project. Care Cure Community Postings for "Gel 'is helping wounds heal in half the time'/nexagon." Sep. 29, 2006 http://sci.rutgers.edu/forum/showthread.php?t=6653.
Collignon et al., Ophthalmology 111:1663-1672 (2004).
Common, J.E.A, Becker, D.L., Di, W.L., Leigh, I.M., O'Toole, E.A. and Kelsell, D.P. (2002) Functional studies of human skin disease- and deafness-associated Connexin 30 mutations. Biochem. Biophys. Res. Commun. 298, 651-656.
Comparison of Age-related Macular Degeneration Treatments Trials (CATT) Research Group, Maguire, M.G. et al. "Five-Year Outcomes with Anti-Vascular Endothelial Growth Factor Treatment of Neovascular Age-Related Macular Degeneration: The Comparison of Age-Related Macular Degeneration Treatments Trials" Ophthalmology Aug. 2016;123(8):1751-1761.
Comparison of Age-related Macular Degeneration Treatments Trials (CATT) Research Group, Martin, D.F. et al. "Ranibizumab and bevacizumab for treatment of neovascular age-related macular degeneration: two-year results" Ophthalmology Jul. 2012;119(7):1388-1398.
Concise Encyclopedia of Polymer Science and Engineering, pp. 858-859 (1990).
Cook, J.E. and Becker, D.L. (1995) Gap Junctions in the vertebrate retina. In Microscopy of Intercellular Communicating Junctions. Ed. R. Gourdie. Microsc. Res. Tech. 31, 408-419.
Cooper, et.al. "Wound healing and inflammation genes revealed by array analysis of macrophageless PU.I null mice." Genome Biology (2004) 6(I): Article 5.
Cotrina, et. al. "Astrocytic gap junctions remain open during ischemic conditions." (Apr. 1, 1998) J. Neurosci., 18: p. 2520-2537.
Cotter et al. Curr Opin Cardiol 16: 159-163, 2001.
Courtman, et al. J Biomed Mater Res 28:655-666 (1994).
Coutinho, et al. "Dynamic Changes in connexin expression correlate with key events in the wound healing process." Cell Biology International 27 (2003) 525-541.
Coutinho, F. P. et al., "Intracellular Oligonucleotide Delivery Using the Cell Penetrating Peptide Xentry", Scientific Reports. Jul. 2018, vol. 8 ( article 11256), pp. 1-10.
Coutinho, P., Frank, S., Qiu, C., Wang, C.M., Brown, T., Green, C.R. and Becker D.L. (2005) Limiting wound extension by transient inhibition of connexin43 expression at the site of injury. Brit. J. Plast. Surg. 58, 658-667.
Cronin M, Anderson PN, Green CR, Becker DL. "Antisense delivery and protein knockdown within the intact central nervous system." Front Biosci 11 (2006): 2967-2975.
Crooke et al., J. Pharmacol. Exp. Ther. 277, 923-937 (1996).
Current Protocols in Immunology (J.E. Coligan et al., eds., 1991) vol. I, Ch. 1.
Current Protocols in Molecular Biology (F.M. Ausubel et al., 1987, including supplements through 2001).
Dagle et al., Nucleic Acids Research 19:1805(1991).

(56) References Cited

OTHER PUBLICATIONS

Dahl G., et al., Biophys J 67:1816-1822 (1994).
Danesh-Meyer, Helen V., et al. "Connexin43 in retinal injury and disease" Progress in Retinal and Eye Research 51 (2016): 41-68.
Danesh-Meyer, Helen V., et al. "Connexin43 mimetic peptide reduces vascular leak and retinal ganglion cell death following retinal ischaemia" Brain 135.2 (2012): 506-520.
Dang, et. al. "The carboxy-tail of connexin-43 localizes to the nucleus and inhibits cell growth." Molecular and Cellular Biochemistry (2003) 242: p. 35-38. Kluwer Academic Publishers. Netherlands.
Dao-Yi et al. Pathogenesis and intervention strategies in diabetic retinopathy. Clin Exp Ophthalmol 29: 164-166, 2001.
Database EMBL, Jul. 9, 2006, "Rattus norvegicus piRNA piR-152346, complete sequence." Retrieved from EBI accession No. EMBL: DQ737024.
Database Geneseq, Dec. 28, 2007, "Viral regulatory miRNA SEQ ID No. 263327" Retrieved from EBI accession No. GSN: AJK11008.
Database Geneseq, Dec. 28, 2007, "Viral regulatory miRNA SEQ ID No. 286128" Retrieved from EBI accession No. GSN AJK33809.
Davis, et al. "Modulation of Connexin43 Expression: Effects on Cellular Coupling" Journal of Cardiovascular Electrophysiology, Futura Publishing Co., 6(2):103-114 (1995).
De Vriese A.S., et al. Kidney Int. 61:177-185 (2002).
Derossi, Daniele, et al. "The third helix of the Antennapedia homeodomain translocates through biological membranes." Journal of Biological Chemistry 269.14 (1994): 10444-10450.
Devereux, et al. Nucleic Acids Research 12:387-395 (1984).
Devlin, G., et al. J. "An ovine model of chronic stable heart failure" J. Card. Fail. 6:140-143 (2000).
DeVries, S.H. and E.A. Schwartz, "Hemi-gap-junction channels in solitary horizontal cells of the catfish retina," Journal of Physiology, 445:201-230 (1992).
Di, W.-L., Lachelin, G.C.L., McGarrigle, H.H.G., Thomas, N.S.B. and Becker, D.L. (2001) Oestriol and oestradiol increase cell to cell communication and connexin 43 protein expression in cultured human myometrial cells. Mol. Human Reprod. 7, 671-679.
Dias, N. and Stein, C.A. Mol. Cancer Thor. Vol. 1, pp. 347-355 (2002).
Diegelmann, et. al. "Wound Healing: An Overview of Acute, Fibrotic and Delayed Healing." (Jan. 1, 2004) Frontiers in Bioscience 9: p. 283-289. Irvine, CA.
Dietz, et al. Ophthalmology 93:1284 (1986).
Doerks et al. Protein annotation: detective work for function prediction. Trends in Genetics 14(6): 248-250, 1998.
Dovi, J.V., et al. J Leukoc Biol 73:448-55 (2003).
Dublin, et. al. "Satellite glial cells in sensory ganglia: Their possible contribution to inflammatory pain." (2007) Brain, Behaviior, and Immunity 21: p. 592-598. Elsevier Inc.
Eckstein, F., ed. Oligonucleotides and Analogues, A Practical Approach, IRL Press at Oxford University Press (1991).
Edgington, Biotechnology 10:256 (1992).
Einarson, M.B. and Orlinich, J.R., "Identification of Protein-Protein Interactions with Glutathione S-Transferase Fusion Proteins," In Protein-Protein Interactions: A Molecular Cloning Manual, Cold Springs Harbor Laboratory Press, pp. 37-57 (2002).
Elbashir S., et al., "Duplexes of 21-nucleotide RNAs mediate RNA interference in cultured mammalian cells." Nature 411:494-498 (2001).
El-Hariri, et al. J. Pharm. Pharmacol. 44:651-654 (1992).
Englisch et al., Angewandte Chemie, International Edition, 30, 613-722 (1991).
Escobar-Chávez, José Juan, et al. "Electroporation as an efficient physical enhancer for skin drug delivery." The Journal of Clinical Pharmacology 49.11 (2009): 1262-1283.
Evans et al., J. Med. Chem. 30:1229 (1987).
Evans, W.H. and Boitano, S., Biochem. Soc. Trans. 29:606-612 (2001).

Extended European Search Report dated Jan. 21, 2014, from corresponding European Patent Application No. 12172475.1, 12 pages.
Fauchere, J. Adv. Drug Res. 15:29-69 (1986).
Ferrin and Camerini-Otero, Science 254:1494-1497 (1991).
Figueroa, Xavier F., and Brian R. Duling. "Gap junctions in the control of vascular function." Antioxidants & Redox Signaling 11.2 (2009): 251-266.
Fingl et al., 1975, "General Principles" In: Goodman & Gilman's The Pharmacological Basis of Therapeutics, 5th Edition, Ch.1, p. 1-46.
Flower NE, Green CR. A new type of gap junction in the phylum Brachiopoda. Cell Tissue Res. 1982;227(1):231-4.
Fonseca CG, Green CR, Nicholson LF. Upregulation in astrocytic connexin 43 gap junction levels may exacerbate generalized seizures in mesial temporal lobe epilepsy Brain Res. Mar. 1, 2002; 929(1):105-16. PMID: 11852037 [PubMed—indexed for MEDLINE].
Foote, et al., J Cell Biol 140(5): 1187-97 (1998).
Forge, A, Becker, D.L., Casalotti, S., Edwards, J., Evans, W.H., Lench, N. and Souter, M. (1999) Gap junctions and connexin expression in the inner ear. In gap junction-mediated intercellular signalling in health and disease. Novartis foundation symposium 219. 134-156. Wiley.
Forge, A., Becker, D.L., Casalotti, S., Edwards, J., Marziano, N. and Nevill, G. (2003) "Gap junctions in the inner ear: comparison of distribution patterns in different vertebrates and assessement of connexin composition in mammals." J. Compo Neurol. 467, 207-231.
Forge, A., Becker, D.L., Casalotti, S., Edwards, J., Marziano, N. and Nickel, R. (2002) Connexins and gap junctions in the inner ear. Audiol. Neuro. Otol. 7,141-145.
Forge, A., Marziano, N., Casalotti, S.O., Becker, D.L. and Jagger, D. (2003). The inner ear contains heteromeric channels composed of Cx26 and Cx30 and deafness-related mutations in Cx26 have a dominant negative effect on Cx30. Cell Commun. Adhes. 10, 341-346.
Fortes, P. et al., Proc. Natl. Acad. Sci. USA 100, 8264-8269 (2003).
Foulkes MR, et al., Stroke 19:547-54 (1988).
Frantseva, M., et al. "Ischemia-Induced Brain Damage Depends on Specific Gap-Junctional Coupling." Journal of Cerebral Blood Flow and Metabolism, 22:453-462 (2002).
Fraser SE, Green CR, Bode HR, Gilula NB. Selective disruption of gap junctional communication interferes with a patterning process in hydra. Science. Jul. 3, 1987;237(4810):49-55. PMID: 3037697 [PubMed—indexed for MEDLINE].
Fujita, Nobuyuki, et al. "HIF-1-PHD2 axis controls expression of syndecan 4 in nucleus pulposus cells." The FASEB Journal 28.6 (2014): 2455-2465.
Galasso, et. al. Seminars in Ophthalmology 19:75-77 (2004).
Garcia-Dorada et al., Circulation 96:3579-3586 (1997).
Gee et al., in Huber and Carr, 1994, "Molecular and Immunologic Approaches," Futura Publishing co, Mt. Kisco NY.
GenBank accession No. U64573.1, "Human connexin43 gap junction protein (connexin43) gene, exon 1 and promoter region," Sep. 28, 1996.
Gerrits, et al., Pediatr Res 57(3):342-6 (2005).
Giani, Andrea, et al. "In vivo evaluation of laser-induced choroidal neovascularization using spectral-domain optical coherence tomography." Investigative Ophthalmology & Visual Science 52.6 (2011): 3880-3887.
Giaume, C., et al. "Control of gap-junctional communication in astrocytic networks." TINS, 19:319-325 (1996).
Giepmans B., J. Biol. Chem., 276(11):8544-8549 (Mar. 16, 2001).
Gil, J., Esteban M., "Induction of apoptosis by the dsRNA-dependent protein kinase (PKR): Mechanisms of action." Apoptosis 2000, 5:107-114.
Gong, Yan, et al. "Optimization of an image-guided laser-induced choroidal neovascularization model in mice." PloS One 10.7 (2015) 15 pages; e0132643. doi:10.1371/journal.pone.0132643.
Goodenough D.A. J Cell Biol 107:1817-1824 (1988).

(56) References Cited

OTHER PUBLICATIONS

Görbe, A., Becker, D.L, Dux, L. and Krenács, T. (2005) In differentiating prefusion myoblasts connexin43 gap junction coupling is upregulated before myoblast alignment then reduced in postmitotic cells. Histochem Cell Biol 123:573-583 [Epub May 14, 2005].
Görbe, A., Becker, DL., Dux, L., Stelkovics, E., Krenács, L., Bagdi, E., and Krenács, T. (2005) Transient upregulation of connexin 43 gap junction coupling in myoblasts may synchronize cell cycle control preceding syncytial fusion during skeletal muscle differentiation Histochem. Cell Biol. 123; 573-583.
Gourdie RG, Green CR, Severs NJ, Anderson RH, Thompson RP. Evidence for a distinct gap-junctional phenotype in ventricular conduction tissues of the developing and mature avian heart. Circ Res. Feb. 1993;72(2):278-89. PMID: 8380357 [PubMed—indexed for MEDLINE].
Gourdie RG, Green CR, Severs NJ, Thompson RP. Immunolabelling patterns of gap junction connexins in the developing and mature rat heart. Anat Embryol (Berl). 1992;185(4):363-78. PMID: 1319120 [PubMed—indexed for MEDLINE].
Gourdie RG, Green CR, Severs NJ. Gap junction distribution in adult mammalian myocardium revealed by an anti-peptide antibody and laser scanning confocal microscopy. J Cell Sci. May 1991;99 (Pt 1):41-55. PMID: 1661743 [PubMed—indexed for MEDLINE].
Gourdie RG, Harfst E, Severs NJ, Green CR. Cardiac gap junctions in rat ventricle: localization using site-directed antibodies and laser scanning confocal microscopy. Cardioscience. Mar. 1990;1(1):75-82. PMID: 1966373 [PubMed—indexed for MEDLINE].
Gourdie, et al. "The spatial distribution and relative abundance of gap-junctional connexin40 and connexin43 correlate to functional properties of components of the cardiac atrioventricular conduction system." Journal of Cell Science 105, 985-991 (1993).
Gourdie, et. al. "The Unstoppable Connexin43 Carboxyl-Terminus" (2006) Ann. N.Y. Acad. Sci. 1080: p. 49-62. New York Academy of Sciences.
Grant G. Evaluation of the Synthetic Product. Synthetic Peptides, A User's Guide, Grant GA, Ed., Second Edition, (2002) 93-219; 220-291, Oxford University Press, New York.
Grazul-Bilska, et al. Abstract, Biology Reproduction, 58(1):78 (1998).
Green C.R, Law, L.Y., Lin, U.S. and Becker, D.L. (2001) "Spatiotemporal depletion of connexins using antisense oligonucleotides. Techniques in the study of gap junctions." Connexin methods and protocols Methods in Molecular Biology, 154 175-185. Eds R. Bruzzone and C. Giuame.
Green CR, Bowles L, Crawley A, Tickle C. Expression of the connexin43 gap junctional protein in tissues at the tip of the chick limb bud is related to the epithelial-mesenchymal interactions that mediate morphogenesis. Dev Biol. Jan. 1994;161(1):12-21. PMID: 8293868 [PubMed—indexed for MEDLINE].
Green CR, Harfst E, Gourdie RG, Severs NJ. Analysis of the rat liver gap junction protein: clarification of anomalies in its molecular size. Proc R Soc Lond B Biol Sci. Mar. 22, 1988;233(1271):165-74. PMID: 2898146 [PubMed—indexed for MEDLINE].
Green CR, Peters NS, Gourdie RG, Rothery S, Severs NJ. Validation of immunohistochemical quantification in confocal scanning laser microscopy: a comparative assessment of gap junction size with confocal and ultrastructural techniques. J Histochem Cytochem. Sep. 1993;41 (9):1339-49. PMID: 8354875 [PubMed—indexed for MEDLINE].
Green CR, Severs NJ. Connexon rearrangement in cardiac gap junctions: evidence for cytoskeletal control? Cell Tissue Res. 1984;237(1):185-6. PMID: 6090023 [PubMed—indexed for MEDLINE].
Green CR, Severs NJ. Gap junction connexon configuration in rapidly frozen myocardium and isolated intercalated disks. J Cell Biol. Aug. 1984;99(2):453-63.
Green CR, Severs NJ. Robert Feulgen Prize Lecture. Distribution and role of gap junctions in normal myocardium and human ischaemic heart disease. Histochemistry. Feb. 1993;99(2): 105-20. Review.

Green CR. Evidence mounts for the role of gap junctions during development. Bioessays. Jan. 1988;8(1):7-10. Review. No abstract available. PMID: 2835035 [PubMed—indexed for MEDLINE].
Green, Maurice, and Paul M. Loewenstein. "Autonomous functional domains of chemically synthesized human immunodeficiency virus tat trans-activator protein." Cell 55.6 (1988): 1179-1188.
Guan, et al., Neuroscience 95(3):831-839 (1999).
Gunn, et al., J Clin Invest 99(2):248-256 (1997).
Gunn, et al., Pediatr Res 46(3):274-280 (1999).
Günther S, Fischer L, Pult I, Sterneck M, Will H. Naturally occurring variants of hepatitis B virus. Adv Virus Res. 1999;52:25-137.
Guo CX, Nor MNM, Danesh-Meyer HV, Vessey K, Fletcher EL, O'Carroll SJ, Acosta ML, Green CR. Connexin43 mimetic peptide improves retinal function and reduces inflammation in a light damaged albino rat model. Investigative Ophthalmology and Visual Science, 2016; 57: 3961-3973.
Guo, Yabing, et al. "Establishment of the consensus sequence of hepatitis B virus prevailing in the mainland of China." Chinese Journal of Microbiology and Immunology—Beijing—19 (1999): 197-200.
Hall, Celia. "Gel is helping wounds heal in half the time." Telegraph UK. Oct. 20, 2003. http://www.telegraph.co.uk/news/main.jhtmil?xml=/news/2003/10/20/ngel20.xml&sSheet=. . . .
Hardman, et al. McGraw-Hill, New York, N.Y., 934-935 (1996).
Hardy, K., Spanos, S. and Becker, D.L. (2003) Cell death (Apoptosis) in human blastocysts. Chpt. 9 p. 185-202 an Atlas of Human Blastocysts. Eds. L.L. Veeck and N. Zaninovic. CRC Press.
Hardy, K., Warner, A.E., Winston, R.M.L. and Becker, D.L. (1996) Expression of intercellular junctions during the preimplantation development of the human embryo. Molec. Human Reprod. 2, 621-632.
Harfst E, Severs NJ, Green CR. Cardiac myocyte gap junctions: evidence for a major connexon protein with an apparent relative molecular mass of 70,000. J Cell Sci. Aug. 1990;96 (Pt 4):591-604.
Harlow and Lane (1988) Antibodies, A Laboratory Manual, Cold Spring Harbor Publications, New York.
Haseloff and Gerlach, Nature Aug. 18;334(6183):585-91 (1988).
Heasman, J., Dev. Biol., 243, 209-214 (2002).
Heier, Jeffrey S., et al. "Intravitreal aflibercept (VEGF trap-eye) in wet age-related macular degeneration." Ophthalmology 119.12 (2012): 2537-2548.
Henikoff and Henikoff Proc. Natl. Acad. Sci. USA 89:10915-10919 (1992).
Hennemann, H., et al. Eur. J. Cell Biol. 58(1):81-9 (1992).
Herbertt, et. al. "Protein Kinase C a Expression is required for heparin inhibition of rat smotth muscle cell proliferation in vitro and in vivo." (Oct. 18, 1996) J Biol Chem. 271(42):259 p. 28-35. The American Society for Biochemistry and Molecular Biology, Inc. U.S.A.
Herve et al. Diversity in protein-protein interactions of connexins: emerging roles. Biochim Biophys Acta 1662: 22-41, 2004.
Ho, et. al., Journal of Neurosurgical Anesthesiology 17:38-44 (2005).
Hodgins, M. "Connecting Wounds with Connexins" J. Invest. Dermatol. 122:(5):ix-x commentary (2004).
Huang, Di, et al. "Hyaluronic acid coated albumin nanoparticles for targeted peptide delivery in the treatment of retinal ischaemia." Biomaterials 168 (2018): 10-23.
Huang, et al. J Cell Biol 143:1725-34 (1998).
Hunter, et. al. "Zonula occludens-1 alters connexin43 gap junction size and organization by influencing channel accretion." (Dec. 2005) Molecular Biology of the Cell 16: p. 5686-5698. The American Society for Cell Biology.
Hunter, Francis W., Bradly G. Wouters, and William R. Wilson. "Hypoxia-activated prodrugs: paths forward in the era of personalised medicine." British Journal of Cancer 114.10 (2016): 1071-1077.
Ilvesaro et al. Connexin-mimetic peptide Gap 27 decreases osteoclastic activity. BMC Musculoskel Dis 2:10, 2001 (6 pages total).
International Search Reeport, PCT Application No. PCT/US08/014022, dated Aug. 12, 2009, 5 pages.
International Search Report in International Patent Application No. PCT/NZ2018/050059, dated Aug. 15, 2018, in 5 pages.

(56) References Cited

OTHER PUBLICATIONS

International Search Report, PCT Application No. PCT/GB00/00238, dated Jun. 19, 2000, 4 pages.
International Search Report, PCT Application No. PCT/US07/024085, dated Jul. 15, 2008, 3 pages.
International Search Report, PCT Application No. PCT/US07/025446, dated Jun. 4, 2008, 3 pages.
International Search Report, PCT Application No. PCT/US08/013655, dated Jun. 8, 2009, 4 pages.
International Search Report, PCT Application No. PCT/US08/013656, dated Jun. 15, 2009, 5 pages.
International Search Report, PCT Application No. PCT/US08/014019, dated Aug. 11, 2009, 5 pages.
International Search Report, PCT Application No. PCT/US08/014020, dated Aug. 6, 2009, 5 pages.
International Search Report, PCT Application No. PCT/US08/014021, dated Aug. 5, 2009, 3 pages.
International Search Report, PCT Application No. PCT/US08/014023, dated Jun. 8, 2010, 3 pages.
International Search Report, PCT Application No. PCT/US08/014024, dated Aug. 11, 2009, 3 pages.
International Search Report, PCT Application No. PCT/US08/014025, dated Aug. 10, 2009, 5 pages.
International Search Report, PCT Application No. PCT/US08/014026, dated Aug. 5, 2009, 5 pages.
International Search Report, PCT Application No. PCT/US08/014028, dated Oct. 14, 2009, 6 pages.
International Search Report, PCT Application No. PCT/US09/00129, dated Nov. 13, 2009, 11 pages.
International Search Report, PCT Application No. PCT/US09/003408, dated Nov. 23, 2009, 3 pages.
J. Goliger, et al., Molecular Biology of the Cell. 6:1491-1501 (1995).
Jackowski et al. Brit J Neurosurg 9: 303-317, 1995.
Janes, Andrew. "Speed healing." Dec. 1, 2004. Issue 67. Unlimited. Sep. 29, 2006 http://unlimited.co.nz/unlimited.nsf/ulfuture/250EA628CE599A70CC256F6B00046325.
Jen, et al., Stem Cells 18:307-319 (2000).
Jester, et al., Cornea 11:191 (1992).
Johnson et al. Am J Opthalmol 147: 11-21, 2009.
Johnsson et al. Transplant Int 12: 235-243, 1999.
Kaal et al. Curr Opin Oncol 16: 593-600, 2004.
Kabanov et al., FEBS Lett. 259, 327 330 (1990).
Kandel ER, Schwartz JH, Jessell TM. Principles of Neural Science, 4th ed., pp. 178-180. McGraw-Hill, New York (2000).
Kandyba, et al. "A murine living skin equivalent amenable to live cell imaging: analysis of the roles of connexins in the epidermis." (Apr. 2008) The Society for Investigative Dermatology.
Kanter, H. Lee, et al., Molecular Cloning of Two Human Cardiac Gap Junction Proteins, Connexin40 and Connexin45, 1994, 861-864, vol. 26, J Mol Cell Cardiol, Academic Press Limited.
Kaplan, Ian M., Jehangir S. Wadia, and Steven F. Dowdy. "Cationic TAT peptide transduction domain enters cells by macropinocytosis." Journal of Controlled Release 102.1 (2005): 247-253.
Karlin and Altschul Proc. Natl. Acad. Sci. USA 90:5873-5787 (1993).
Kawaguchi, Yoshimasa, et al. "Syndecan-4 is a receptor for clathrin-mediated endocytosis of arginine-rich cell-penetrating peptides." Bioconjugate Chemistry 27.4 (2016): 1119-1130.
Keirstead, H.S., et al. Exp. Neurol. 159:225-236 (1999).
Khosla, et. al., Journal of Postgraduate Medicine 50:219-221 (2004).
Kieber-Emmons T, et al., Curr Opin Biotechnol. Aug;8(4):435-41 (1997).
Kim, Won-Young, and Sang-Bum Hong. "Sepsis and acute respiratory distress syndrome: recent update." Tuberculosis and Respiratory Diseases (Seoul) 79.2 (2016): 53-57.
Kim, Y et al., "Characterizing the Mode of Action of Extracellular Connexin43 Channel Blocking Mimetic Peptides in an in vitro Ischemia Injury Model", Biochimica et Biophysica Acta. Feb. 2017, vol. 1861(2), pp. 68-78.
Kim, Yeri, et al. "Role of hemichannels in CNS inflammation and the inflammasome pathway." Advances in Protein Chemistry and Structural Biology. vol. 104. Academic Press, 2016. 1-37.
Kojima, T. et al., "Plasma Levels of Syndecan-4 (Ryudocan) Are Elevated in Patients with Acute Myocardial Infarction", Thromb Haemost. 2001, vol. 85(5), pp. 793-799.
Koo, Heebeom, et al. "The movement of self-assembled amphiphilic polymeric nanoparticles in the vitreous and retina after intravitreal injection." Biomaterials 33.12 (2012): 3485-3493.
Kurpakus-Wheater, et al. Biotech. Histochem. 74:146-59 (1999).
Lambert, Vincent, et al. "Laser-induced choroidal neovascularization model to study age-related macular degeneration in mice." Nature Protocols 8.11 (2013): 2197-2211.
Lampugnani, M.G., "Cell Migration into a wounded area in vitro" Methods Mol Biol 96:177-182 (1999).
Landau et al. Am Heart J 129(5): 924-931, 1995.
Laux-Fenton WT, Donaldson PJ, Kistler J, Green CR. Connexin expression patterns in the rat cornea: molecular evidence for communication compartments. Cornea. Jul. 2003;22(5):457-64. PMID: 12827052 [PubMed—indexed for MEDLINE].
Law, et. al. "In vitro optimization of antisense ologodeoxynucleotide design: an example using the connexin gene family." Journal of Biomolecular techniques. (Sep. 2006) 17(4): p. 270-282.
Law, L.-Y., Lin, J.S, Becker, D.L. and Green, C.R. (2002) Knockdown of Connexin 43 mediated regulation of ZPA activity in the developing chick limb bud leads to digit truncation. Dev. Growth Differ. 44, 537-547.
Lee et al. Critical Reviews in Therapeutic Drug Carrier Systems 8:91-192 (1991).
Lemanske et al. J Allergy Clin Immunol 111 :S502-19, 2003.
Letsinger et al., Proc. Natl. Acad. Sci. USA 86, 6553-6556 (1989).
Leybaert et. al., Cell Commun Adhes 10:251-257 (2003).
Li, et al. Dev. 129:2031-42 (2002).
Li, H., et al., "properties and regulation of gap junctional hemichannels in the plasma membranes of cultured cells," Journal of Cell Biology 134(4): 1019-1030 (1996).
Liaw, et. al. "Altered wound healing in mice lacking a functional osteopontin gene (sppl)" (Apr. 1998) The Journal of Clinical Investigation 101(7): p. 1468-1478.
Lin, et. al. "v-Src phosphorylation of connexin 43 on Tyr247 and Tyr265 disrupts gap junctional communication." (Aug. 20, 2001) Journal of Cell Biology. 154: p. 815-827. The Rockefeller University Press.
Lin, J.H. et al.,"Gap-Junction-mediated propogation and amplification of cell injury." Nature Neurosci. 1:431-432(1998).
Linker Database of the Centre for Integrative Bioinformatics VU at Vrije University of Amsterdam, found at http://www.ibi.vu.nl/programs/linkerdbwww/, downloaded Jan. 23, 2020, 2 pages.
Liu, et. al. "The Inhibition of in vivo tumorigenesis of osteosarcoma (OS)-732 Cells by antisense human osteopontin RNA." (2008) 13: p. 11-19. University of Wroclaw, Poland.
Lohman, Alexander W., and Brant E. Isakson. "Differentiating connexin hemichannels and pannexin channels in cellular ATP release." FEBS Letters 588.8 (2014): 1379-1388.
Makarenkova, H., Becker, D.L., Tickle, C. and Warner, A.E. (1997) Fibroblast growth factor 4 directs gap junction expression in the mesenchyme of the vertebrate limb bud. J. Cell Biol. 138, 1-13.
Malone, et al. J Vasc Surg 1:181-91 (1984).
Manoharan et al. Nucleosides & Nucleotides 14, (3-5) 969-973 (1995).
Manoharan et al., Bioorg. Med. Chem. Let. 3(12), 2765-2770 (1993).
Manoharan et al., Bioorg. Med. Chem. Lett. 4, 1053-1060 (1994).
Manoharan et al., Tetrahedron Lett. 36(21), 3651-3654 (1995).
Marmarou, A. Neurosurg Focus 22(5): E1-10, 2007.
Martin et al., Helv. Chim. Acta 1995, 78, 486-504.
Martin, P. Science 276:75-81 (1997).
Martin, P., et al. Curr Biol 13:1122-8 (2003).
Marx, Jean. "Interfering with Gene Expression." Science 288:1370-1372 (2000).

(56) References Cited

OTHER PUBLICATIONS

Marziano, N., Casalotti, S.O., Portelli A.E., Becker, D.L. and Forge, A. (2003) Deafness-related mutations in gap junction protein connexin 26 have a dominant negative effect on connexin 30. Human Molecular Genetics 203, 805-812.
Matsune, Shoji, et al. "Hypoxia in paranasal sinuses of patients with chronic sinusitis with or without the complication of nasal allergy." Acta Oto-laryngologica 123.4 (2003): 519-523.
Mattu et al. Emerg Med Clin N Am 23: 1105-1125, 2005.
Mcdonald, et al. Scientific American. 55-63 (Sep. 1999).
McDonnell and Schanzlin, Arch. Ophthalmol. 106:212 (1988).
McGonnell, I., Green, C.R., Tickle, C. and Becker, D.L. (2001) Communication through connexin 43 gap junction channels contributes to the normal development of the embryonic face. Dev. Dynam. 222, 420-438.
Medical Futures—Innovation Awards. May 26, 2006 http://www.medicalfutures.co.uk/runner.php?txtWin=1.
Meienhofer in "Hormonal Proteins and Peptides," ed.; C.H. Li, vol. 2 (Academic Press, 1973) pp. 48-267.
Melton, D.A. Antisense RNA and DNA, Ed., Cold Spring Harbor Laboratory, Cold Spring Harbor, NY (1988).
Même, William, et al. "Proinflammatory cytokines released from microglia inhibit gap junctions in astrocytes: potentiation by ß-amyloid." The FASEB Journal 20.3 (2006): 494-496.
Merrifield, J. Am. Chem. Soc. 85 2149 (1963).
Methods of Immunological Analysis (R. Masseyeff, W.H. Albert, and N.A. Staines, eds., Weinheim: VCH Verlags gesellschaft mbH, 1993) vol. I, Ch. 1, 2, 3, 4, vol. III, Ch. 4.
Meyer R.A., J Cell Biol. 119:179-189 (1992).
Miller, J.M., & Calos, M.P., eds. 1987) Gene Transfer Vectors for Mammalian Cells, Introduction.
Mishra et al., Biochim. Biophys. Acta 1264, 229-237 (1995).
Miyazaki, et. al. "Corneal Wound Healing in an Osteopontin-Deficient Mouse." (Apr. 2008) Investigative Ophthalmology & Visual Science 49(4): p. 1367-1375. Association for Research in Vision and Ophthalmology.
Molecular cloning: A Laboratory Manual, 3rd Edition Chapter 10 (Sambrook and Russel, 2001).
Montrose, K. et al., "The Tetrapeptide Core of the Carrier Peptide Xentry is Cell-Penetrating: Novel Activatable Forms of Xentry", Scientific Reports. 2014, vol. 4 (article 4900), pp. 1-11.
Montrose, K. et al., "Xentry, a New Class of Cell-Penetrating Peptide Uniquely Equipped for Delivery of Drugs" Scientific Reports 2013, vol. 3 (article 1661), pp. 1-7.
Moore, et al., Am. J. Physiology. 267(5):C1371-C1388 (Nov. 1, 1994).
Mori, et al. Supplemental Materials and Methods. Online Supplemental Material. (2008) http://www.jem.org/cgi/content/full/jem.20071412/DC1 JEM The Rockefeller University Press.
Mori, et al., "Acute downregulation of connexin43 at wound sites leads to a reduced inflammatory response, enhanced keratinocyte proliferation and wound fibroblast migration." Journal of Cell Science. 119(24): p. 5193-5203 (Dec. 2006). The Compny of Biologists 2006.
Mori, et. al. "Molecular mechanisms linking wound inflammation and fibrosis: knock down of osteopontin leads to rapid repair and reduced scarring." Department of Physiology and Biochemistry, School of Medical Sciences, University of Bristol, Bristol BS8 1TD, United Kingdom. (Jan. 7, 2008); p. 43-55.
Mori, R., et al. "Impairment of skin wound healing in beta-1,4-galactosyltransferase-deficient mice with reduced leukocyte recruitment." Am J. Pathol. 164:1303-14 (2004).
Morrissey, et al. J. Neuroscience 11:2433-2442 (1991).
Mugisho 00, Green CR, Kho DT, Zhang J, Scott Graham E, Acosta ML, Rupenthal ID. The inflammasome pathway is amplified and perpetuated in an autocrine manner through connexin43 hemichannel mediated ATP release. Biochim Biophys Acta. Nov. 17, 2017. pii: S0304-4165(17)30380-X. doi: 10.1016/j.bbagen.2017.11.015. [Epub ahead of print].
Muramatsu, et. al. "Inhibition of osteopontin expression and function in oral cancer cell lines by antisense oligonucleotides." (2005) Cancer Letters 217:87-95. Elsevier.
Muranishi. Critical Reviews in Therapeutic Drug Carrier Systems. 7:1-33 (1990).
Mustoe, T.A., et al. Science 237, 1333-6 (1987).
Nadarajah, B., Makarenkova, H., Becker, D.L., Evans, W.H. and Parnavelas, J.G. (1998) Basic FGF increases communication between cells of the developing neocortex. J. Neurosci. 18, 7881-7890.
Nakano, et. al. "Changes in the expression of the gap junction protein connexin43 during wound healing of the rat corneal endothelium." (Dec. 2004) Bioimages 12(2-4). Bioimaging Society.
Neckers, et al. "Anti-sense technology: biological utility and practical considerations." Am. J. Physiol. 265 (lung cell mol physiol), L1-L12 (1993).
News bio-active gel cuts wound healing time in half. Oct. 20, 2003. UCL Media Relations. University College London. Sep. 29, 2006 http://www.ucl.ac.uk/media/library/nexagon0.
Ngo et al. Computational complexity, protein structure prediction, and the Levinthal paradox. The Protein Folding Problem and Tertiary Structure Prediction, pp. 492-495, 1994.
Nice blurb on biologies on cbsnews.com. Laxat. Sep. 9, 2006 http://www.laxat.com/Nice-blurb-on-biologics-on-cbsnews-com-1219610.html.
Nickel, R., Becker, D.L. and Forge, A. Molecular and functional characterization of gap junctions in the avian inner ear. J. Neurosci. Jun. 7, 2006;26(23):6190-9.
Nielsen et al., Science 254:1497 (1991).
Nowak, J.Z. Age-related macular degeneration (AMD): pathogenesis and therapy. Pharmacol Reports 58: 353-363, 2006.
Oberhauser et al., Nucl. Acids Res. 20, 533-538 (1992).
Okada, et. al. "Osteopontin expressed by renal tubular epithelium mediates interstitial monocyte infiltration in rats." Am Physiol Renal Physiol. (2000) 278:F110-F121. The American Physiological Society.
Oligonucleotide Synthesis Chapter 1 (M.J. Gait, ed., 1984).
Oviedo-Orta E., et. al. "Gap Junctions and Connexin-Mediated Communication in the Immune System." Biochimica et Biophysica Acta. Biomembranes, Amsterdam, NL vol. 1662, No. 1-2, 23, Mar. 2004, pp. 102-112.
Oviedo-Orta et al. Gap junctions and connexins: potential contributors to the immunological synpase. J Leuk Biol 72: 636-642, 2002.
Paddison, P., Caudy A., Bernstein, E., Hannon, G., Conklin, D., "Short hairpin RNAs (shRNAs) induce sequence-specific silencing in mammalian cells." Genes & Dev 16:948-958 (2002).
Paddison, P., Caudy A., Hannon G., "Stable suppression of gene expression by RNAi in mammalian cells." Proc Natl Acad Sci USA 99:1443-1448 (2002).
Papangelou et al. Curr Treatment Options in Neurol 11:64-73, 2009.
Parker, J.D., et al. Nucleic Acids Res 19:3055-60 (1991).
Partial European Search Report dated Sep. 26, 2013, from corresponding European Patent Application No. 12172475.1, 8 pages.
PCR: The Polymerase Chain Reaction Chapter 1-19 (Mullis et al., eds., 1994).
Pearson, R., Lüneborg N., Becker D.L. and Mobbs P. (2005) Gap junctions modulate interkinetic nuclear migration in retinal progenitor cells. J. Neurosci. 25, 10803-10814.
Penn, et. al., Autoimmunity Reviews 2:199-203 (2003).
Pepose, J.S., et al. "The cornea; Adler's Physiology of the eye: Clinical application," 9th Ed. St. Louis: Mosby Year Book, 1992, 29-47.
Peters NS, Green CR, Poole-Wilson PA, Severs NJ. Cardiac arrhythmogenesis and the gap junction. J Mol Cell Cardiol. Jan. 1995;27(1):37-44. Review. No abstract available. PMID: 7760358 [PubMed—indexed for MEDLINE].
Peters NS, Green CR, Poole-Wilson PA, Severs NJ. Reduced content of connexin43 gap junctions in ventricular myocardium from hypertrophied and ischemic human hearts. Circulation. Sep. 1993;88(3):864-75. PMID: 8394786 [PubMed—indexed for MEDLINE].

(56) References Cited

OTHER PUBLICATIONS

Peters NS, Rowland E, Bennett JG, Green CR, Anderson RH, Severs NJ. The Wolff-Parkinson-White syndrome: the cellular substrate for conduction in the accessory atrioventricular pathway. Eur Heart J. Jul. 1994; 15(7):981-7. PMID: 7925521 [PubMed—indexed for MEDLINE].
Peters NS, Severs NJ, Rothery SM, Lincoln C, Yacoub MH, Green CR. Spatiotemporal relation between gap junctions and fascia adherens junctions during postnatal development of human ventricular myocardium. Circulation. Aug. 1994;90(2):713-25. PMID: 8044940 [PubMed—indexed for MEDLINE].
Peters, T., et al. EMBO J. 24:3400-10 (2005).
Ponsaerts, R. et al., "Intramolecular Loop/Tail Interactions are Essential for Connexin 43-Hemichannel Activity", The FASEB Journal 2010, vol. 24(11), pp. 4378-4395.
Postlethwaite, A.E., et al. J Exp Med 165:251-6 (1987).
Prausnitz, Mark R., and Robert Langer "Transdermal drug delivery." Nature Biotechnology 26.11 (2008): 1261-1268.
Qiu, et al; "Supplemental Data: Targeting Connexin43 Expression Accelerates the Rate of Wound Repair"; (2003) S1.
Qui, et al., "Targeting connexin43 expression accelerates the rate of wound repair." Current Biology 13:1967-1703 (2003).
R. Ruch, et al. Molecular Carcinogenesis, 14:269-274 (1995).
Rabinstein, A. Neurologist 12: 59-73, 2006.
Ramdas et al., J. Biol. Chem. 264:17395 (1989).
Ramer, et al. Spinal Cord. 38:449-472 (2000).
Ramezani A., et al., Frontiers in Bioscience 7:a,29-36 (2002).
Ratkay-Traub, I., Hopp, B., Bor, Zs., Dux, L., Becker, D.L. and Krenacs, T. (2001) Regeneration of rabbit cornea following excimer laser photorefractive keratectomy: a study on gap junctions, epithelial junctions and epidermal growth factor receptor expression in correlation with cell proliferation. Exp. Eye Res. 73, 291-302.
Reddy, K., et al., Pediatric Research 43(5):674-682 (1998).
Rennick RE, Connat JL, Burnstock G, Rothery S, Severs NJ, Green CR. Expression of connexin43 gap junctions between cultured vascular smooth muscle cells is dependent upon phenotype. Cell Tissue Res. Feb. 1993;271(2):323-32. PMID: 8384084 [PubMed—indexed for MEDLINE].
Retamal, Mauricio A., et al. "Cx43 hemichannels and gap junction channels in astrocytes are regulated oppositely by proinflammatory cytokines released from activated microglia." Journal of Neuroscience 27.50 (2007): 13781-13792.
Reynolds, et al. Nat. Med. 11:167-74 (2005).
Rhett, et. al. "Novel therapies for scar reduction and regenerative healing of skin wounds." (Mar. 4, 2008). Trends in Biotechnology. 26(4): 173-180. Cell Press.
Rigas et al., Proc. Natl. Acad. Sci U.S.A. 83:9591 (1986).
Rininsland et al., Proc. Natl. Acad. Sci. USA 94:5854 (1997).
Robbins, S. and Cotran, R. 1979 Pathologic basis of disease. 2nd edition. Chapters 1-3 WB Saunders Co., Philadelphia.
Roberts, et al. Proc Natl Acad Sci USA 83:4167-71 (1986).
Roberts, R., Iatropoulou, A., Ciantar, D., Stark, J., Becker, D.L., Franks, S. and Hardy, K. (2005) Follicle-stimulating hormone affects metaphase I chromosome alignment and increases aneuploidy in mouse oocytes matured in vitro. Biol. Reprod. 72, 107-118.
Roelfsema, et .al., J Cereb Blood Flow Metab 24(8):877-886 (2004).
Rosendaal M, Green CR, Rahman A, Morgan D. Up-regulation of the connexin43+ gap junction network in haemopoietic tissue before the growth of stem cells. J Cell Sci. Jan. 1994; 107 (Pt 1):29-37.
Rozenthal, et al. "Stable Transfection With Connexin43 inhibits Neuronal Differentiation of PC12 Cells" Society for Neuroscience Abstracts, Society for Neuroscience 23(1-3), Oct. 25, 1997, p. 22.
Rutherford, R.B., Vascular Surgery, 3rd Ed. (W.B. Saunders Co. 1989).
Sabiston, D., The Textbook of Surgery, 14th Ed. Chapter 56 (W.B. Saunders Co. 1991).
Saez et al. Physiol Rev 83:1359-1400, 2003.
Saison-Behmoaras et al. Embo J. 10, 1111-11118(1991).
Saitongdee, P., Becker, D.L., Milner, P., Knight, G.E., and Burnstock, G. (2004) Levels of gap junction proteins in coronary arterioles and aorta of hamsters exposed to cold and during hibernation and arousal. J. Histochem Cytochem 52), 603-615.
Saitongdee, P., Milner, P., Becker, D.L., Knight, G.E., and Burnstock, G. (2000) Increased connexin43 gap junction protein in hamster cardiomyocytes during cold acclimatization and hibernation. Cardiovascular Res. 47, 108-115.
Sakamoto, T., et al. "Improvement of dermatitis by iontophoretically delivered antisense oligonucleotides for interleukin-10 in NC/Nga mice." Gene Therapy 11.3 (2004): 317-324.
Sambrook, et al. Molecular Cloning: Chapter 11-12 A Laboratory Manual (1989).
Sanghvi, Y.S., Chapter 15, Antisense Research and Applications, pp. 276-278 Crooke, S.T. and Lebleu, B., ed., CRC Press (1993).
Santoro, S.W. and Joyce, G.F. Biochem. 37:13330-13342 (1998).
Santoro, S.W. et. al. "A General Purpose RNA-Cleaving DNA Enzyme." Proc. Natl. Acad. Sci. USA 94, p. 4262-4266 (1997). The National Academy of Sciences of the USA.
Scatchard et al., Ann. N.Y. Acad. Sci. 51(4):660 (1949).
Scherer, L.J. and Rossi, J.J. Nature Biotechnol. 21(12):1457-1465 (2003).
Schmidt, C.E., et al. Ann. Rev. Biomed. Eng. 5:293-347 (2003).
Schubert, S. et al., Nucleic Acids Res. 31, 5982-5992 (2003).
Schuck, P., "Reliable determination of binding affinity and kinetics using surface plasmon resonance biosensor," Current Opinion in Biotechnology, 8(4):498-502 (1997).
Schulz et al. Connexin 43 is an emerging therapeutic target in ischemia/reperfusion injury, cardioprotection and neuroprotection. Pharmacol Therapeut 153: 90-106, 2015.
Schumacher et al. Circulation 97: 645-650, 1998.
Severs NJ, Gourdie RG, Harfst E, Peters NS, Green CR. Intercellular junctions and the application of microscopical techniques: the cardiac gap junction as a case model. J Microsc. Mar. 1993;169 (Pt 3):299-328. Review. PMID: 8478912 [PubMed—indexed for MEDLINE].
Severs NJ, Shovel KS, Slade AM, Powell T, Twist VW, Green CR. Fate of gap junctions in isolated adult mammalian cardiomyocytes. Circ Res. Jul. 1989;65(1):22-42. PMID: 2736737 [PubMed—indexed for MEDLINE].
Severs NJ, Slade AM, Powell T, Twist VW, Green CR. Integrity of the dissociated adult cardiac myocyte: gap junction tearing and the mechanism of plasma membrane resealing. J Muscle Res Cell Motil. Apr. 1990;11(2):154-66. PMID: 2351753 [PubMed—indexed for MEDLINE].
Shah, et al. Am. J. Pathol. 154:1115-24 (1999).
Shah, Ronil S., et al. "A mouse model for laser-induced choroidal neovascularization." JoVE (Journal of Visualized Experiments) 106 (2015): e53502, 7 pages; doi:10.3791/53502.
Shea et al., Nucl. Acids Res. 18, 3777-3783 (1990).
Shevde, et. al "Osteopontin knockdown suppresses tumorigenicity of human metastatic breast carcinoma, MDA-MB-435." Clin Exp Metastasis (2006) 23: p. 123-133. Springer Science + Business Media B.V.
Sica, D. Heart Failure Clin 4: 511-518, 2008.
Simo et al. Angiogenic and Antiangiogenic factors in proliferative diabetic retinopathy. Current Diabetes Rev 2: 71-98, 2006.
Simons, et. al. "Anti-sense c-myb oligonucleotides inhibit intimal arterial smooth muscle cell accumulation in vivo." (Sep. 3, 1992): Nature, 359: p. 67-70. Nature Publishing Group.
Singh, et. al. "Inhibition of connexin 43 synthesis by antisense RNA in rat glioma cells." (1997) Cytobios 91: p. 103-123. The Faculty Press. Great Britain.
Skolnick et al. From genes to protein structure and function: novel applications of computational approaches in the genomic era. Trends in Biotech 18(1): 34-39, 2000.
Smith et al. The challenges of genome sequence annotation or "The devil is in the details". Nature Biotech 15: 1222-1223, 1997.
Smith JH, Green CR, Peters NS, Rothery S, Severs NJ. Altered patterns of gap junction distribution in ischemic heart disease. An immunohistochemical study of human myocardium using laser scanning confocal microscopy. Am J Pathol. Oct. 1991;139(4):801-21. PMID: 1656760 [PubMed—indexed for MEDLINE].

(56) References Cited

OTHER PUBLICATIONS

Som, I., Bhatia, K., Yasir, M., "Status of surfactants as penetration enhancers in transdermal drug delivery" J. Pharm. Bioallied Sci. (2012) 4, 2-9.
Spanos, S., Rice, S., Karagiannis, P., Taylor, D., Becker, D.L., Winston, R.M.L. and Hardy, K. (2002) Caspase activity and expression of cell death genes during human preimplantation embryo development. J. Reprod. 124, 353-363.
Spencer, W.H., "The cornea: Ophthalmic Patholgy: an atlas and textbook" 4th Ed. Philadelphia: W.B. Saunders Co., 1996, 157-165.
Stein C.A. and Krieg A.M. (eds), Chapters 7, 10, 22. Applied Antisense Oligonucleotide Technology, 1998 (Wiley-Liss).
Stein, C.A.. "Anti-sense oligodeoxynucleotides—promises and pitfalls." Leukemia 6:967-974, 1992.
Stewart, et al., "Solid Phase Peptide Synthesis," Chapter 2 Part B, Chapter 3. W.H. Freeman Co., San Francisco (1984).
Stilinovic A., Green, C.R., Klette R., Franke S., Klette G and Becker D.L. (2004) Texture analysis of collagen fibers in scar tissue. In Proc. Image Vision Computing New Zealand Nov. 21, pp. 185-190.
STN Biosis Caesar accession No. 1231, Grazul-Bilska, "Transfection of bovine luteal cells with gap junctional protein connexin 43 (Cx43) antisense oligonucleotide affects progesterone secretion." AN (1998):379610.
STN Biosis Caesar accession No. 1233. Moore, Lisa. "Selective block of gap junction channel expression with connexin-specific antisense oligodeoxynucleotides." AN (1995):31398.
Stout, Charles E., et al. "Intercellular calcium signaling in astrocytes via ATP release through connexin hemichannels" Journal of Biological Chemistry 277.12 (2002): 10482-10488.
Strobel et al., Science 254:1639 (1991).
Sui., G., et al., Proc Natl Acad Sci 99(8):5515-5520 (2002).
Sulaiman, Rania S., et al. "A simple optical coherence tomography quantification method for choroidal neovascularization." Journal of Ocular Pharmacology and Therapeutics 31.8 (2015): 447-454.
Sundstrom, Drug Discovery Today 10:993-1000 (2005).
Suzuki, et. al. Protective effects of recombinant osteopontin on early brain injury after subarachnoid hemorrhage in rats. (2010) Crit Care Med 38(2): p. 612-618.
Svinarchuk et al., Biochimie 75, 49-54 (1993).
Takahashi, et al. J. Pharm. Pharmacol. 40:252-257 (1988).
Tan, et al., Ann Neurol 32(5):677-682 (1992).
Tanaka, T., et al. Jpn. J. Ophthalmol. 43:348-54 (1999).
Tarnow, et al. Scand J. Plast Reconstr Hand Surg. 28:255-259 (1994).
The Immunoassay Handbook (D. Wild, ed., Stockton Press NY 1994).
Tokuriki et al. Stability effects of mutations and protein evolvability. Curr Opinion Structural Biol 19: 596-604, 2009.
Topol, E.J. (ed.) The Textbook of Interventional Cardiology, 2nd Ed. (W.B. Saunders Co. 1994).
Tunnemann, G., and M. Cristina Cardoso. "Cell-Penetrating Peptides—Uptake, Toxicity, and Applications." Membrane Active Peptides: Methods and Results on Structure and Function 9 (2009), Chapter 14, 36 pages.
Uhlmann, et al., Chem. Reviews 90:543-584 (1990).
UniProtKB—P17302 (CXA1_HUMAN), Definition: Gap junction alpha-1 protein (Gene GJA1) Entry version 238 (Dec. 11, 2019) URL at https://www.uniprot.org/uniprot/P17302, downloaded Jan. 16, 2020, 28 pages.
Veber and Freidinger, TINS, 392 (1985).
Vikis, H.G. and Guan, K.L. Glutathione-S-Transferase-Fusion Based Assays for Studying Protein-Protein Interactions in Protein-Protein Interactions, Methods and Applications, Methods in Molecular Biology, 261, Fu, H.Ed. Humana Press, Totowa, N.J., pp. 175-186 (2004).
Vis JC, Nicholson LF, Faull RL, Evans WH, Severs NJ, Green CR. Connexin expression in Huntington's diseased human brain. Cell Biol Int. Nov. 1998;22(11-12):837-47. PMID: 10873295 [PubMed—indexed for MEDLINE].

Vives, Eric, Priscille Brodin, and Bernard Lebleu. "A truncated HIV-1 Tat protein basic domain rapidly translocates through the plasma membrane and accumulates in the cell nucleus" Journal of Biological Chemistry 272.25 (1997): 16010-16017.
Wadia, Jehangir S., Radu V. Stan, and Steven F. Dowdy. "Transducible TAT-HA fusogenic peptide enhances escape of TAT-fusion proteins after lipid raft macropinocytosis." Nature Medicine 10.3 (2004): 310-315.
Waggett A.D., et al. Connexin 32 and 43 gap junctions differentially modulate tenocyte esonse to cyclic mechanical load. Eur. J. Cell. Biol. 085:1145-1154 (2006).
Wagner, R.W., et al. "Gene inhibition using anti-sense oligodeoxynucleotides." Nature 372:333-335 (1994).
Wai, et. al. "Osteopontin silencing by small interfering RNA suppresses in vitro and in vivo CT26 murine colon adenocarcinoma metastasis." (2005) Carcinogenesis 26(4): p. 741-751. Oxford University Press.
Walker, et al. Dev Biol 284:479-98 (2005).
Waring, et al., Amer. J. Ophthalmol. 111:133 (1991).
Welcome to the lab of David Becker and Jeremy Cook. Becker/Cook Lab. May 26, 2006 http://www.anat.ucl.ac.uk/research/becker/people.htm.
Wells. J.A. Additivity of mutational effects in proteins. Biochemistry 29 (37): 8509-8517, 1990.
Wier, D.M. & C.C. Blackwell, eds. Handbook of Experimental Immunology, Ch. 85 and 86, 1986.
Willebrords, Joost, et al. "Connexins and their channels in inflammation." Critical Reviews in Biochemistry and Molecular Biology 51.6 (2016): 413-439.
Willecke, et. al. "Mouse connexin 37: Cloning and functional expression of a gap function gene highly expressed in lung." (Sep. 1991) The Journal of Cell Biology 114(5): p. 1049-1057. The Rockefeller University Press.
Willecke, K., et al. "Structural and functional diversity of connexin genes in the mouse and human genome." Biol. Chem., 383:725-37 (2002).
Wilson, et al. "Accellular Matrix" Trans Am Soc Artif Intern 36:340-343 (1990).
Wound-healing technology shortlisted for award. UCL News. University College London. Sep. 27, 2006 http://www.ucl.ac.uk/news-archive/archive/2003/october-2003/latest/newsitem.shtml?0309 . . .

Wright, C.S., Becker, D.L., Lin, S.J., Warner, A.E. and Hardy, K. (2001) Stage-specific and differential expression of gap junctions in the mouse ovary: connexin-specific roles in follicular regulation. J. Reprod. Fert. 121, 77-88.
Wright, et. al. "Connexin mimetic peptides improve cell migration rates of human epidermal keratinocytes and dermal fibroblasts in vitro." (2009) Wound Rep Reg 17: p. 240-249. The Wound Healing Society.
Written Opinion of the International Searching Authority, PCT Application No. PCT/IB04/004431, dated Jan. 3, 2006, 6 pages.
Written Opinion of the International Searching Authority, PCT Application No. PCT/IB06/001961, dated May 13, 2008, in 6 pages.
Wyngaarden J.B., et al. (eds.), The Cecil Textbook of Medicine, 19th Ed. (W.B. Saunders, 1992).
Xu, X.M., et al. J. Comp. Neurol. 351:145-160 (1995).
Xu, X.M.,et al. Eur. J. Neuroscience. 11:1723-1740(1999).
Yamashita, et al. J. Pharm. Pharmacol. 39:621-626 (1987).
Yang, Lihu, et al. Proc. Natl. Acad. Sci. 1;95(18):10836-10841 (Sep. 1, 1998).
Yick, L.W., et al. Exp. Neurol. 159:131-138 (1999).
Zhang, Jie, et al. "Connexin hemichannel induced vascular leak suggests a new paradigm for cancer therapy." FEBS Letters 588.8 (2014): 1365-1371.
Zhang, X., Oglesbee, M., "Use of surface plasmon resonance for the measurement of low affinity binding interactions between HSP72 and measles virus nucleocapsid protein." Biological Procedures Onlin 5(1):170-181 (2003).
Zhang, Y. et al., "Myocyte-Dependent Regulation of Endothelial Cell Syndecan-4 Expression", The Journal of Biological Chemistry. 1999, vol. 274(21), pp. 14786-14790.

(56) References Cited

OTHER PUBLICATIONS

Zhou, et. al. "Blockade of Osteopontin Inhibits Glomerular Fibrosis in a Model of Anti-Glomerular Basement Membrane Glomerulonephritis." (Aug. 19, 2010) Am J Nephrol 32: p. 324-331. Karger AG, Basel. (Published Online.).

Zimmer DB, Green CR, Evans WH, Gilula NB. Topological analysis of the major protein in isolated intact rat liver gap junctions and gap junction-derived single membrane structures. J Biol Chem. Jun. 5, 1987;262(16):7751-63. PMID: 3034905 [PubMed—indexed for MEDLINE].

Zlotnik, A., and Rossi Annu rev Immunol 18:217-42 (2000).

Zon, G., Ann. N.Y. Acad. Sci., 616, 161-172 (1990).

METHODS OF TREATMENT AND NOVEL CONSTRUCTS

CROSS-REFERENCE TO RELATED APPLICATIONS

This application is a § 371 national stage entry of International Application No. PCT/NZ2018/050059, filed Apr. 30, 2018, which claims the benefit of priority to New Zealand applications NZ731353 filed Apr. 28, 2017 and NZ731364 filed Apr. 28, 2017, the entire contents of each of which are incorporated herein by reference in their entirety.

SEQUENCE LISTING

The instant application contains a Sequence Listing which has been filed electronically in ASCII format and is hereby incorporated by reference in its entirety. Said ASCII copy, created on Apr. 3, 2020, is named E3697-00540_SL.txt and is 23,152 bytes in size.

FIELD

The present invention relates to novel methods for targeting compounds to hypoxic cells, including methods of treatment involving same, and constructs for such use. The present invention further relates to novel methods for use in treatment of disorders and/or diseases of the eye and constructs for such use.

BACKGROUND

Many diseases and disorders are associated with hypoxic cells and/or tissues. For example, age-related macular degeneration (AMD) and diabetic retinopathy are both associated with ischemia of the retina, causing the death of retinal pigment epithelium cells. By way of further example, tumours (such as in cancer) have poor vascular supply and are hypoxic and/or have portions or zones that are hypoxic, resulting in tissue with reduced oxygen levels. In the case of tumours, continued ischemia can promote the survival of hypoxia-resistant tumour cells over normal cells. Structural abnormalities in tumour blood vessels may influence therapeutic responses to treatments.

By way of further example, there are a number of diseases and disorders associated with hypoperfusion leading to hypoxia, including stroke and transient ischemic attacks, cardiac ischemia, ischemic colitis (ischemia of the large intestine), sepsis, acute limb ischemia, cutaneous ischemia, multiple sclerosis, vascular dementia, and Alzheimer's disease.

While there are some treatments available for certain diseases associated with hypoxia, these are not without problem.

For example, current treatment options for acute ischemia most commonly target the cause of the ischemia (for example thrombosis), and include injection of an anticoagulant, thrombolysis, embolectomy, surgical revascularisation, or amputation. Another option is lowering body or organ temperature in an attempt to reduce the aerobic metabolic rate of the affected cells, reducing the immediate effects of hypoxia. However, ischemic tissue continues to degenerate after such treatments. For example, sepsis is associated with the development of hypoperfusion. Treatment approaches then move to attempting to limit the subsequent effects of the ischemic insult. However, these approaches are frequently associated with off-target effects and side effects.

Similarly, current approaches for treatment of diseases and disorders associated with chronic ischemia are associated with off-target effects and side effects. For example, both AMD and diabetic retinopathy are currently treated primarily with intravitreal injections of anti-VEGF agents, including for example VEGF-Trap. It has recently been acknowledged that long-term treatment may result in anti-VEGF resistance with best-corrected visual acuity after five years of treatment being below baseline in a number of cases (1-3). In addition, overuse of anti-VEGF agents may contribute to loss of good vessels, increasing tissue ischemia (24).

In the case of tumours, the side effects of chemotherapy are well documented. These side effects are frequently attributable to the fact that therapeutic agents of use in the treatment of cancer are taken up by cells in a non-specific manner and have toxic effects on normal cells.

Connexin channel blockers have previously been shown to reduce chronic inflammation and promote blood vessel integrity (18, 29, 30). Certain connexin channel blockers, for example Gap19, need to enter the cell in order to bind cytoplasmic domains of connexins. For example Gap19 binds to the cytoplasmic tail of the connexin Cx43. The plasma membrane of eukaryotic cells has poor permeability to many chemical compounds, significantly reducing their efficacy, for example as therapeutics or experimental reagents, particularly when they need to reach the cytoplasm to be efficacious. Due to poor permeability of connexin channel blockers such as Gap19, high concentrations have previously been used in order to achieve efficacy (6, 7). However, administration of Gap19 at high concentrations may have undesirable side effects such as off-target effects or an unsolicited immune response.

Technologies have been developed to improve the cell permeability of chemical compounds, including the use of lipid-, polycationic-, nanoparticle- and peptide-based methods. However, these technologies are not without problem. For example, cell permeable carrier peptides may be large and expensive to manufacture, making them commercially non-viable. Carrier peptides may also interfere with the conformation of the molecule which they carry, reducing efficacy of those compounds. Carrier peptides may also lack specificity for target tissues or cells resulting in off-target effects which may be undesirable. Many carrier peptides are highly cationic. For example, they may contain high concentrations of the amino acid arginine. Such carrier peptides may show toxicity at higher concentrations owing to induced membrane leakage (31).

The above examples demonstrate the need for alternative treatment options for delivery to hypoxic cells, and for alternative options for delivery of intracellularly acting connexion channel blockers.

Bibliographic details of the publications referred to herein are collected at the end of the description.

OBJECT

It is an object of the present invention to provide methods of targeting delivery of a compound to hypoxic cells, methods of treating a disease or disorder associated with hypoxia, methods of treating a disease or disorder of the eye, uses of a construct, uses of a nucleic acid, uses of a nucleic acid vector comprising a nucleic acid encoding a construct, methods of increasing uptake of a compound, methods of preparing medicaments for increasing uptake of a compound, methods of reducing off-target effects of a therapeutic agent, constructs, nucleic acids encoding constructs, and/or nucleic acid vectors encoding a construct that overcomes or ameliorates a disadvantage of the prior art. It is a further alternate object of the invention to provide the public with a useful choice.

STATEMENT OF INVENTION

The invention provides a novel method of targeting delivery of a compound to hypoxic cells, for example treatment of diseases and disorders associated with hypoxia, comprising administration of a construct comprising a targeting carrier peptide and a compound for delivery to a hypoxic cell.

The invention also provides a novel method for the treatment of diseases or disorders of the eye by administration of a novel construct, a nucleic acid encoding a novel construct, and/or a nucleic acid vector comprising a nucleic acid encoding a novel construct.

The invention further provides novel constructs, nucleic acids encoding such constructs, and/or nucleic acid vectors comprising nucleic acids encoding such constructs.

Accordingly, in a first broad aspect, the invention provides a method of targeting delivery of a compound to hypoxic cells in a subject comprising: administering to the subject a construct comprising (a) a targeting carrier peptide derived from the X-protein of the Hepatitis B virus and (b) the compound.

In a second broad aspect, the invention provides a method of targeting delivery of a peptide compound to hypoxic cells in a subject comprising: administering to the subject a nucleic acid encoding a construct comprising (a) a targeting carrier peptide derived from the X-protein of the Hepatitis B virus and (b) the peptide compound.

In a third broad aspect, the invention provides a method of targeting delivery of a peptide compound to hypoxic cells in a subject comprising: administering to the subject a nucleic acid vector comprising a nucleic acid encoding a construct comprising (a) a targeting carrier peptide derived from the X-protein of the Hepatitis B virus and (b) the peptide compound.

In a fourth broad aspect, the invention provides a method of treating a disease or disorder associated with hypoxia comprising: administering to a subject a construct comprising (a) a targeting carrier peptide derived from the X-protein of the Hepatitis B virus and (b) a therapeutic agent of use in treating the disease or disorder.

In a fifth broad aspect, the invention provides a method of treating a disease or disorder of the eye comprising: administering to a subject a construct comprising (a) a targeting carrier peptide derived from the X-protein of the Hepatitis B virus and (b) a peptide capable of interacting with an intracellular domain of connexin43 (Cx43).

In a sixth broad aspect, the invention provides a method of treating a disease or disorder associated with hypoxia comprising: administering to a subject a nucleic acid encoding a construct comprising (a) a targeting carrier peptide derived from the X-protein of the Hepatitis B virus and (b) a peptide therapeutic agent of use in treating the disease or disorder.

In a seventh broad aspect, the invention provides a method of treating a disease or disorder of the eye comprising: administering to a subject a nucleic acid encoding a construct comprising (a) a targeting carrier peptide derived from the X-protein of the Hepatitis B virus and (b) a peptide capable of interacting with an intracellular domain of connexin43 (Cx43).

In an eighth broad aspect, the invention provides a method of treating a disease or disorder associated with hypoxia comprising: administering to a subject a nucleic acid vector comprising a nucleic acid encoding a construct comprising (a) a targeting carrier peptide derived from the X-protein of the Hepatitis B virus and (b) a peptide therapeutic agent of use in treating the disease or disorder.

In a ninth broad aspect, the invention provides a method of treating a disease or disorder of the eye comprising: administering to a subject a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43).

In a tenth broad aspect, the invention provides a method of treating a disease or disorder associated with hypoxia comprising: administering to a subject a composition comprising a construct comprising (a) a targeting carrier peptide derived from the X-protein of the Hepatitis B virus and (b) a therapeutic agent of use in treating the disease or disorder, in combination with one or more carrier, excipient, and/or diluent.

In an eleventh broad aspect, the invention provides a method of treating a disease or disorder of the eye comprising: administering to a subject a composition comprising a construct comprising (a) a targeting carrier peptide derived from the X-protein of the Hepatitis B virus and (b) a peptide capable of interacting with an intracellular domain of connexin43 (Cx43) in combination with one or more carrier, excipient, and/or diluent.

In a twelfth broad aspect, the invention provides a method of treating a disease or disorder associated with hypoxia comprising: administering to a subject a composition comprising a nucleic acid encoding a construct comprising (a) a targeting carrier peptide derived from the X-protein of the Hepatitis B virus and (b) a peptide therapeutic agent of use in treating the disease or disorder, in combination with one or more carrier, excipient, and/or diluent.

In a thirteenth broad aspect, the invention provides a method of treating a disease or disorder of the eye comprising: administering to a subject a composition comprising a nucleic acid encoding a construct comprising (a) a targeting carrier peptide derived from the X-protein of the Hepatitis B virus and (b) a peptide capable of interacting with an intracellular domain of connexin43 (Cx43) in combination with one or more carrier, excipient, and/or diluent.

In a fourteenth broad aspect, the invention provides a method of treating a disease or disorder associated with hypoxia comprising: administering to a subject a composition comprising a nucleic acid vector comprising a nucleic acid encoding a construct comprising (a) a targeting carrier peptide derived from the X-protein of the Hepatitis B virus and (b) a peptide therapeutic agent of use in treating the disease or disorder, in combination with one or more carrier, excipient, and/or diluent.

In a fifteenth broad aspect, the invention provides a method of treating a disease or disorder of the eye comprising: administering to a subject a composition comprising a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) in combination with one or more carrier, excipient, and/or diluent.

In an sixteenth broad aspect, the invention provides the use of a construct comprising (a) a targeting carrier peptide derived from the X-protein of the Hepatitis B virus and (b)

a therapeutic agent, in the manufacture of a medicament for treating a disease or disorder associated with hypoxia.

In a seventeenth broad aspect, the invention provides the use of a construct comprising (a) a targeting carrier peptide derived from the X-protein of the Hepatitis B virus and (b) a peptide capable of interacting with an intracellular domain of connexin43 (Cx43) in the manufacture of a medicament for treating a disease or disorder of the eye.

In a eighteenth broad aspect, the invention provides the use of a nucleic acid encoding a construct comprising (a) a targeting carrier peptide derived from the X-protein of the Hepatitis B virus and (b) a peptide therapeutic agent, in the manufacture of a medicament for treating a disease or disorder associated with hypoxia.

In a nineteenth broad aspect, the invention provides the use of a nucleic acid encoding a construct comprising (a) a targeting carrier peptide derived from the X-protein of the Hepatitis B virus and (b) a peptide capable of interacting with an intracellular domain of connexin43 (Cx43) in the manufacture of a medicament for treating a disease or disorder of the eye.

In a twentieth broad aspect, the invention provides the use of a nucleic acid vector comprising a nucleic acid encoding a construct comprising (a) a targeting carrier peptide derived from the X-protein of the Hepatitis B virus and (b) a peptide therapeutic agent, in the manufacture of a medicament for treating a disease or disorder associated with hypoxia.

In a twenty-first broad aspect, the invention provides the use of a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) in the manufacture of a medicament for treating a disease or disorder of the eye.

In a twenty-second broad aspect, the invention provides the use of a construct comprising (a) a targeting carrier peptide derived from the X-protein of the Hepatitis B virus and (b) a therapeutic agent, for the treatment of a disease or disorder associated with hypoxia.

In a twenty-third broad aspect, the invention provides the use of a construct comprising (a) a targeting carrier peptide derived from the X-protein of the Hepatitis B virus and (b) a peptide capable of interacting with an intracellular domain of connexin43 (Cx43) for treating a disease or disorder of the eye.

In a twenty-fourth broad aspect, the invention provides the use of a nucleic acid encoding a construct comprising (a) a targeting carrier peptide derived from the X-protein of the Hepatitis B virus and (b) a peptide therapeutic agent, for the treatment of a disease or disorder associated with hypoxia.

In a twenty-fifth broad aspect, the invention provides the use of a nucleic acid encoding a construct comprising (a) a targeting carrier peptide derived from the X-protein of the Hepatitis B virus and (b) a peptide capable of interacting with an intracellular domain of connexin43 (Cx43) for treating a disease or disorder of the eye.

In a twenty-sixth broad aspect, the invention provides the use of a nucleic acid vector comprising a nucleic acid encoding a construct comprising (a) a targeting carrier peptide derived from the X-protein of the Hepatitis B virus and (b) a peptide therapeutic agent, for the treatment of a disease or disorder associated with hypoxia.

In a twenty-seventh broad aspect, the invention provides the use of a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) for treating a disease or disorder of the eye.

In a twenty-eighth broad aspect, the invention provides a method of targeting delivery of a compound to hypoxic cells, the method comprising: contacting a construct comprising (a) a targeting carrier peptide derived from the X-protein of the Hepatitis B virus and (b) the compound with a population of hypoxic cells.

In a twenty-ninth broad aspect, the invention provides a method of targeting delivery of a compound to hypoxic cells in a mixed population of hypoxic and non-hypoxic cells, the method comprising: contacting a construct comprising (a) a targeting carrier peptide derived from the X-protein of the Hepatitis B virus and (b) the compound with a mixed population of cells or a composition comprising a mixed population of cells.

In an thirtieth broad aspect, the invention provides a method of targeting delivery of a peptide compound to hypoxic cells, the method comprising: contacting a nucleic acid encoding a construct comprising (a) a targeting carrier peptide derived from the X-protein of the Hepatitis B virus and (b) the peptide compound with a population of hypoxic cells.

In a thirty-first broad aspect, the invention provides a method of targeting delivery of a peptide compound to hypoxic cells in a mixed population of hypoxic and non-hypoxic cells, the method comprising: contacting a nucleic acid encoding a construct comprising (a) a targeting carrier peptide derived from the X-protein of the Hepatitis B virus and (b) the compound with a mixed population of cells or a composition comprising a mixed population of cells.

In a thirty-second broad aspect, the invention provides a method of targeting delivery of a peptide compound to hypoxic cells, the method comprising: contacting a nucleic acid vector comprising a nucleic acid encoding a construct comprising (a) a targeting carrier peptide derived from the X-protein of the Hepatitis B virus and (b) the peptide compound with a population of hypoxic cells.

In a thirty-third broad aspect, the invention provides a method of targeting delivery of a peptide compound to hypoxic cells in a mixed population of hypoxic and non-hypoxic cells, the method comprising: contacting a nucleic acid vector comprising a nucleic acid encoding a construct comprising (a) a targeting carrier peptide derived from the X-protein of the Hepatitis B virus and (b) the compound with a mixed population of cells or a composition comprising a mixed population of cells.

In a thirty-fourth broad aspect, the invention provides a method of increasing uptake of a compound (including a therapeutic agent) by a hypoxic cell or cells, the method comprising connecting the compound to a targeting carrier peptide derived from the X-protein of the Hepatitis B virus.

In a thirty-fifth broad aspect, the invention provides a method of increasing uptake of a peptide compound (including a therapeutic agent) by a hypoxic cell or cells, the method comprising connecting a nucleic acid encoding the peptide compound to a nucleic acid encoding a targeting carrier peptide derived from the X-protein of the Hepatitis B virus.

In a thirty-sixth broad aspect, the invention provides a method of preparing a medicament for increased uptake of a compound (including a therapeutic agent) by a hypoxic cell or cells, the method comprising connecting the compound to a targeting carrier peptide derived from the X-protein of the Hepatitis B virus.

In a thirty-seventh broad aspect, the invention provides a method of preparing a medicament for increased uptake of a peptide compound (including a therapeutic agent) by a hypoxic cell or cells, the method comprising connecting a nucleic acid encoding the peptide compound to a nucleic acid encoding a targeting carrier peptide derived from the X-protein of the Hepatitis B virus.

In a thirty-eighth broad aspect, the invention provides a method of reducing off-target effects of a therapeutic agent, the method comprising connecting the therapeutic agent to a targeting carrier peptide derived from the X-protein of the Hepatitis B virus, wherein the therapeutic agent is for delivery to a hypoxic cell or cells.

In a thirty-ninth broad aspect, the invention provides the invention provides a method of reducing off-target effects of a peptide therapeutic agent, the method comprising connecting a nucleic acid encoding the peptide therapeutic agent to a nucleic acid encoding a targeting carrier peptide derived from the X-protein of the Hepatitis B virus.

In a fortieth broad aspect, the invention provides a construct comprising (a) a targeting carrier peptide derived from the X-protein of the Hepatitis B virus and (b) a peptide capable of interacting with an intracellular domain of connexin43 (Cx43).

In a forty-first broad aspect, the invention provides a composition comprising a construct comprising (a) a targeting carrier peptide derived from the X-protein of the Hepatitis B virus and (b) a peptide capable of interacting with an intracellular domain of connexin43 (Cx43) in combination with one or more carrier, excipient, and/or diluent.

In a forty-second broad aspect, the invention provides a nucleic acid encoding a construct comprising (a) a targeting carrier peptide derived from the X-protein of the Hepatitis B virus and (b) a peptide capable of interacting with an intracellular domain of connexin43 (Cx43).

In a forty-third broad aspect, the invention provides a composition comprising a nucleic acid encoding a construct comprising (a) a targeting carrier peptide derived from the X-protein of the Hepatitis B virus and (b) a peptide capable of interacting with an intracellular domain of connexin43 (Cx43) in combination with one or more carrier, excipient, and/or diluent.

In a forty-fourth broad aspect, the invention provides a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43).

In a forty-fifth broad aspect, the invention provides a composition comprising a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) in combination with one or more carrier, excipient, and/or diluent.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying figures.

A number of the figures illustrate cells or nuclei which have been labelled or stained in different colours. When reproduced in black and white, all the spots visible in these Figures represent cells or nuclei, in accordance with the label or stain used, unless otherwise stated. In some cases, colours became very dim or invisible when the figures were reproduced in black and white, hence contrast and brightness were increased. The changes were made to faithfully reproduce the colour photographs.

FIG. 1. hRMEC uptake of Gap19 and XG19. hRMEC cells were treated with XG19 (10, 20 or 50 µM) or Gap19 (10, 20, 50 or 100 µM) or left untreated (no peptide) as a control. Peptides were FITC labelled and therefore uptake was observed by visualising FITC levels in the cytoplasm (white areas in the FITC panel) and nuclei were visualised by DAPI stain (white areas in the DAPI panel). The merge panel shows the overlap of the DAPI and FITC panels for each treatment. This figure shows effective XG19 uptake into endothelial cells at concentrations as low as 10 µM, whereas Gap19 alone is undetectable inside the cells even at 50 µM.

Figure 2:
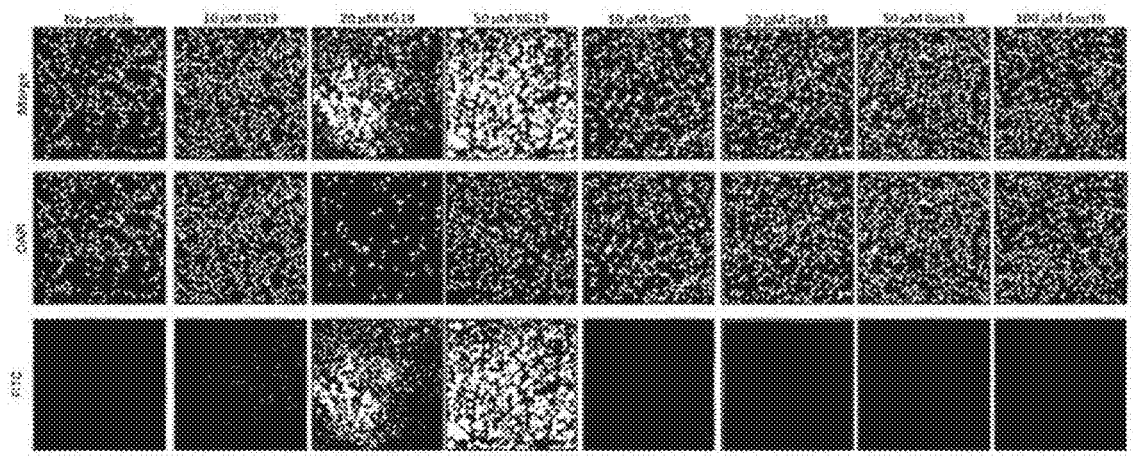

FIG. 2. ARPE-19 uptake of Gap19 and XG19. ARPE-19 cells were treated with XG19 (10, 20 or 50 µM), Gap19 (10, 20, 50 or 100 µM) or left untreated (no peptide) as a control. Peptides were FITC labelled and therefore uptake was observed by visualising FITC levels in the cytoplasm (white areas in the FITC panel) and nuclei were visualised by DAPI stain (white areas in the DAPI panel). The merge panel shows the overlap of the DAPI and FITC panels for each treatment. This figure shows effective XG19 uptake into ARPE-19 cells at concentrations as low as 10 µM, whereas Gap19 alone is undetectable inside the cell even at 100 µM.

Figure 3:
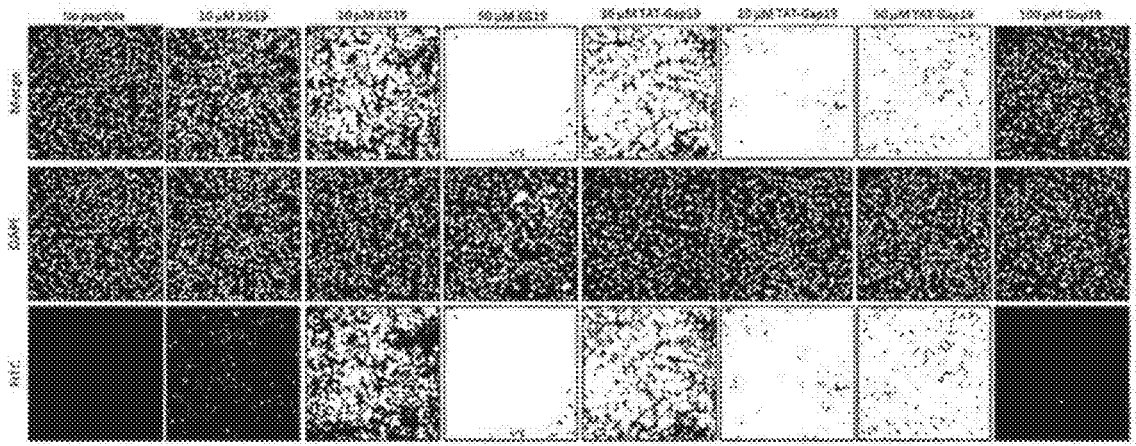

FIG. 3. TAT-Gap19 and XG19 uptake into ARPE-19 cells. ARPE-19 cells were treated with XG19 (10, 20 or 50 µM) or TAT-Gap19 (10, 20, 50 µM), Gap19 (100 µM) or left untreated (no peptide) as a control. Peptides were FITC labelled and therefore uptake was observed by visualising FITC levels in the cytoplasm (white areas in the FITC panel) and nuclei were visualised by DAPI stain (white areas in the DAPI panel). The merge panel shows the overlap of the DAPI and FITC panels for each treatment. Whilst TAT-Gap19 appears to have higher cell uptake than XG19 at this magnification TAT-Gap19 is mainly accumulated into the nucleus (see FIGS. 4 and 4A).

Figure 4:
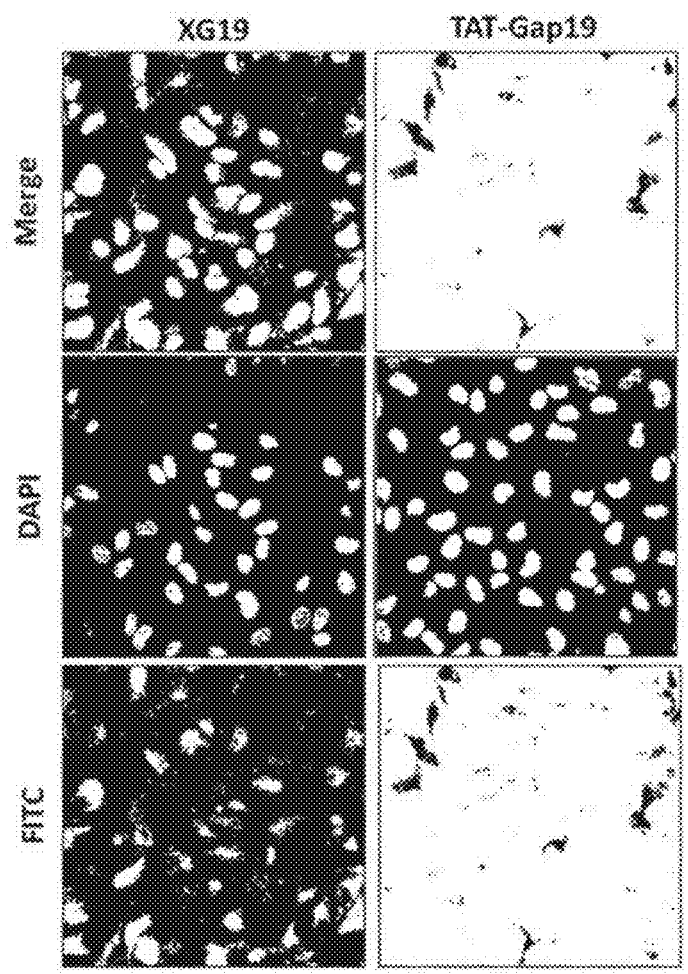

FIG. 4. Nuclear uptake of TAT-Gap19 into ARPE-19 cells. Observation and comparison of TAT-GAP19 (right) and XG19 (left) nuclear uptake in ARPE19 cells. Peptides were FITC labelled and therefore uptake was observed by visualising FITC levels (white areas in the FITC panel) and nuclei were visualised by DAPI stain (white areas in the DAPI panel). The merge panel shows the overlap of the DAPI and FITC panels for each treatment. Whilst TAT-Gap19 appears to have higher uptake, it is accumulated into the nucleus. This could be detrimental to nuclear function and means that the attached Gap19 is not available for block of hemichannel opening.

Figure 4A:
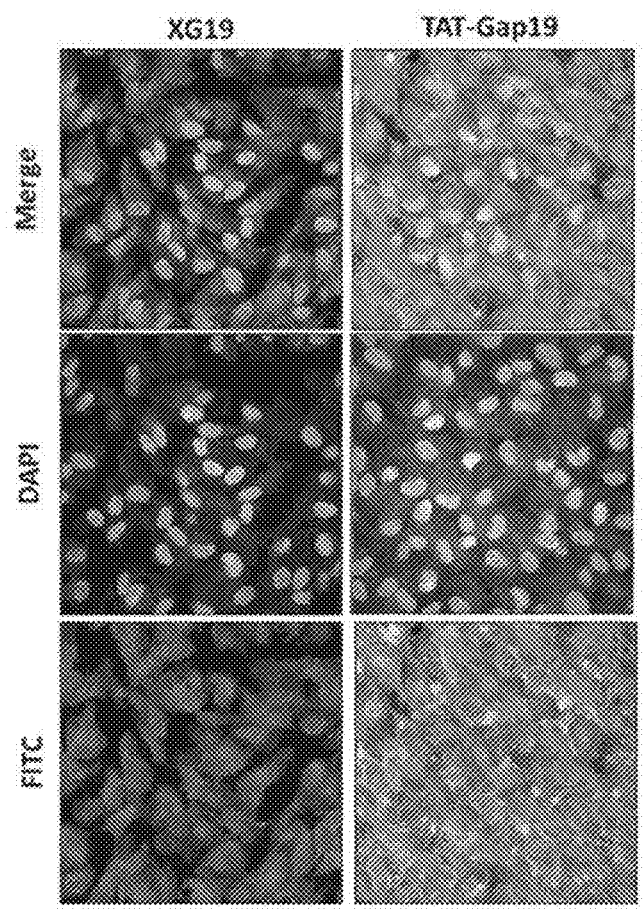

FIG. 4A. Nuclear uptake of TAT-Gap19 into ARPE-19 cells. This is the same as FIG. 4 but reproduced in greyscale rather than black and white. Observation and comparison of TAT-GAP19 (right) and XG19 (left) nuclear uptake in ARPE19 cells. Peptides were FITC labelled and therefore uptake was observed by visualising FITC levels (white spots and grey areas in the FITC panel) and nuclei were visualised by DAPI stain (grey areas in the DAPI panel). The merge panel shows the overlap of the DAPI and FITC panels for each treatment. Whilst TAT-Gap19 appears to have higher uptake, it is accumulated into the nucleus as indicated by the presence of white spots in the nuclear area seen in the FITC channel, which is not seen with XG19 uptake. This could be detrimental to nuclear function and means the Gap19 is not available for block of hemichannel opening.

Figure 5:
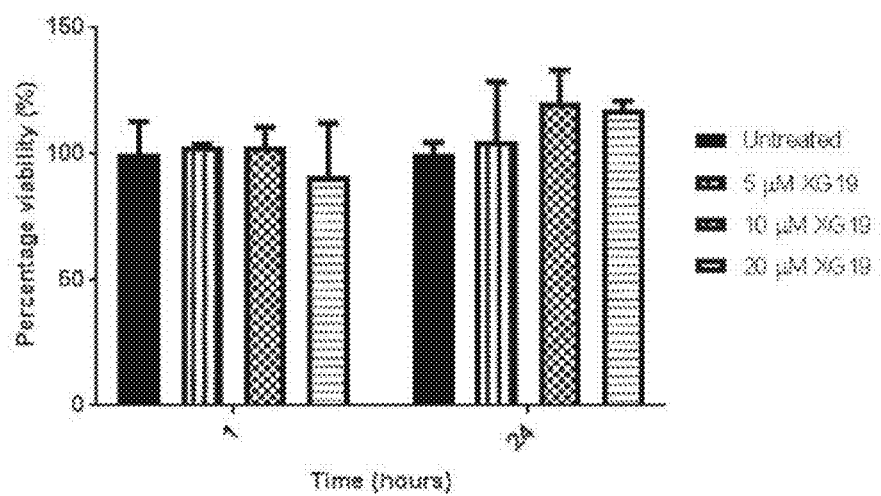

FIG. 5. XG19 does not show cytotoxicity. MTT cytotoxicity assay of ARPE-19 cells exposed to increasing concentrations of XG19 (5 μM (vertical stripes), 10 μM (check pattern) or 20 μM (horizontal stripes)) for 1 or 24 h and compared to untreated cells as a control (black). There was no significant difference in cell viability in untreated cells compared to XG19 treated cells at any of the concentrations or time points tested. This showed that XG19 was not toxic to cells at both short and long time intervals. Statistical analysis was carried out by two-way ANOVA and post hoc comparisons using Dunnett's multiple comparisons test.

Figure 6:
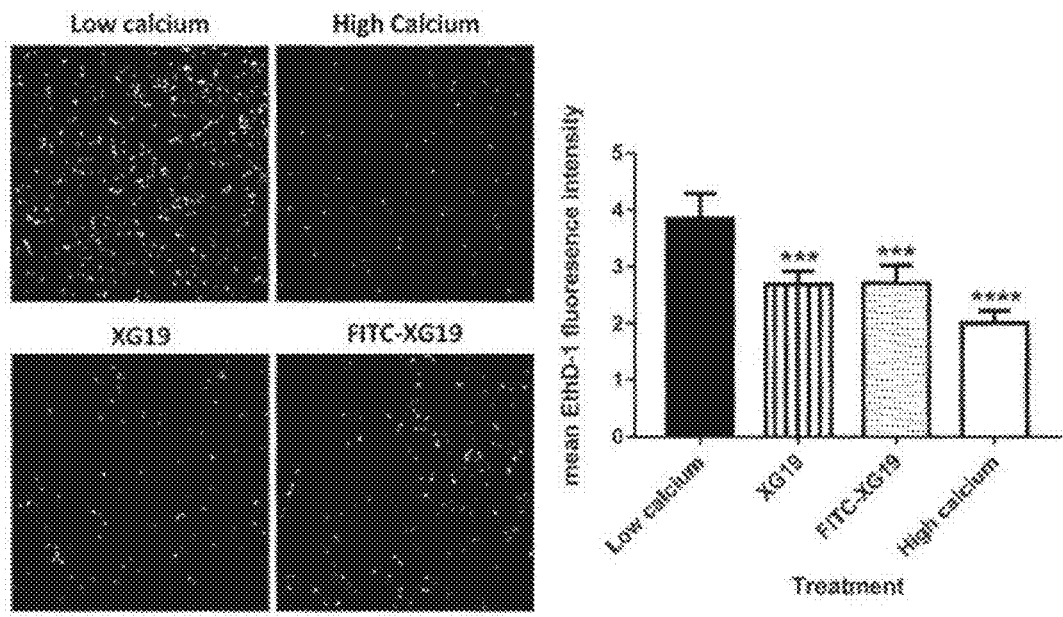

FIG. 6. Hemichannel mediated uptake of EthD-1. ARPE-19 cells were treated with low calcium solution alone to allow hemichannel opening (top left), high calcium solution to block hemichannel opening (top right), 5 μM XG19 (bottom left) or 5 μM FITC-XG19 (bottom right) in low calcium solution and EthD-1 (white area) uptake was observed by confocal microscopy. Cells treated with 5 μM XG19 (or FITC coupled XG19) show reduced EthD-1 uptake indicating inhibition of hemichannel opening by Gap19 (indicating that the FITC label has not affected function). The images were quantified by measuring the mean EthD-1 fluorescence intensity in four areas per treatment and a graph was plotted (right) (n=4; mean+SD). One-way ANOVA was carried out with post hoc Dunett's test and significance was represented as a difference from the low calcium control (*p<0.001, **p<0.0001).

Figure 7:
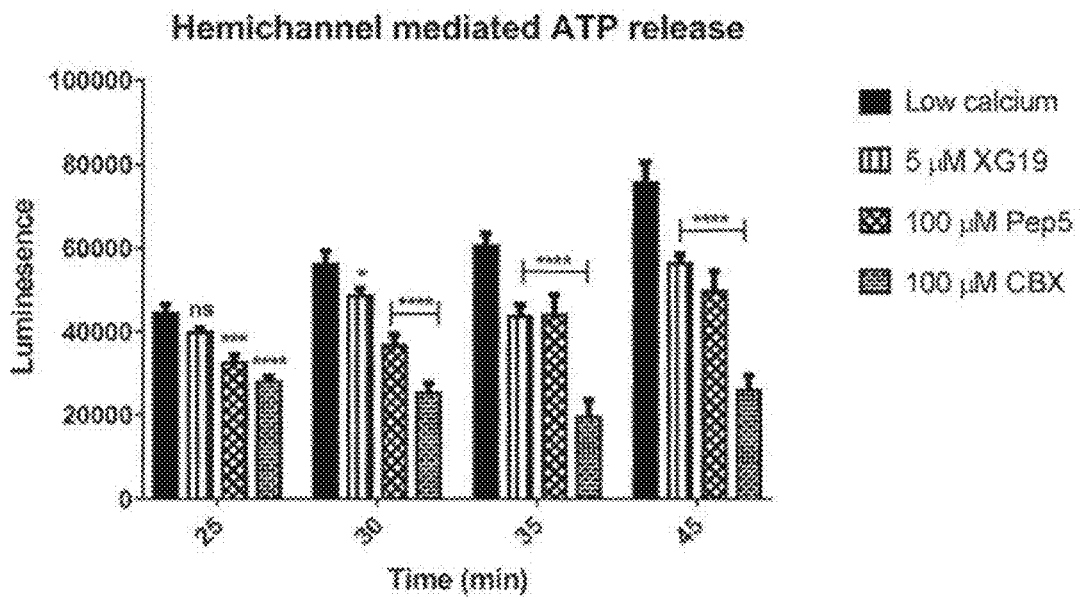

FIG. 7. Hemichannel mediated ATP release. 5 μM XG19 (stripe), 100 μM Peptide5 (Pep5) (diamond) and 100 μM carbenoxolone (CBX) (brick) were applied to ARPE-19 cells for 1 h before treating cells with low calcium solution (to open hemichannels) (solid black) for 25-45 min. The solutions were collected and ATP was measured by a luminescence assay (n=3; mean+SD). Low concentrations of XG19 (even as low as 5 μM) were as effective at reducing ATP release as much higher concentrations of the extracellular acting PepS. Statistical analysis was carried out by two-way ANOVA and post hoc comparisons using Dunnett's multiple comparisons test. Significance is in comparison to the low calcium control at each time point (p*<0.05, p*<0.001, p**<0.0001).

Figure 8:
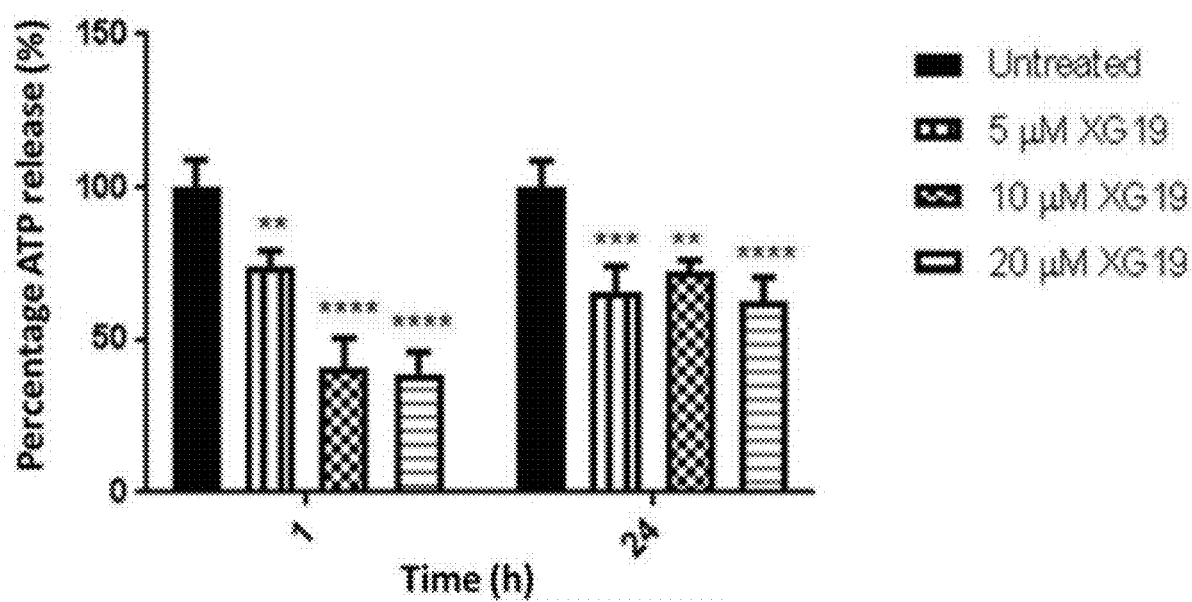

FIG. 8. XG19 inhibits Cx43 hemichannel mediated ATP release at 1 and 2 h post uptake. Hemichannel function was assessed via ATP release assay in ARPE-19 cells either 1 h or 24 h post cellular uptake of increasing concentrations of XG19 (5 μM (vertical stripes), 10 μM (check pattern) or 20 μM (horizontal stripes)) and compared to untreated cells (black). XG19 treated cells showed significantly less ATP release compared to untreated cells at both 1 and 24 h time points. This showed that XG19 function can be maintained 24 h post cellular uptake. Therefore XG19 is in a bioavailable and functional form 24 h post uptake. Statistical analysis was carried out by two-way ANOVA and post hoc comparisons using Sidak's multiple comparisons test. Significance is in comparison to the untreated control at each time point (p<0.01, p*<0.001, p****<0.0001).

Figure 9:
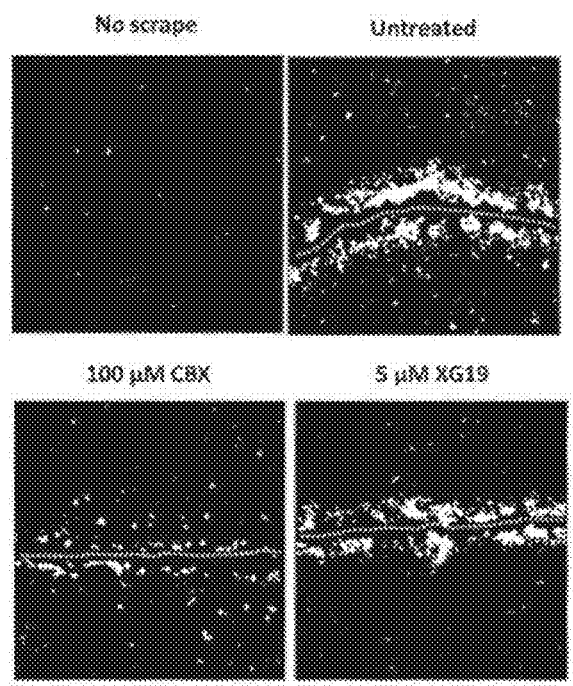

FIG. 9. Dye scrape/load gap junction assay in ARPE-19 cells. ARPE-19 cells that were not scraped (top left) did not take up the Lucifer yellow dye (white area in all panels). Cells that were scraped (white dotted line) took up dye at the site of injury which was passed onto neighbouring cells via open gap junctions (top right). Carbenoxolone (CBX), a known gap junction blocker, inhibited gap junction communication and thus dye spread (bottom left). Dye spread was seen in cells treated with XG19 showing functional gap junctions (bottom right). XG19 at the dose previously shown to block hemichannel opening has no effect on gap junction coupling.

Figure 10:
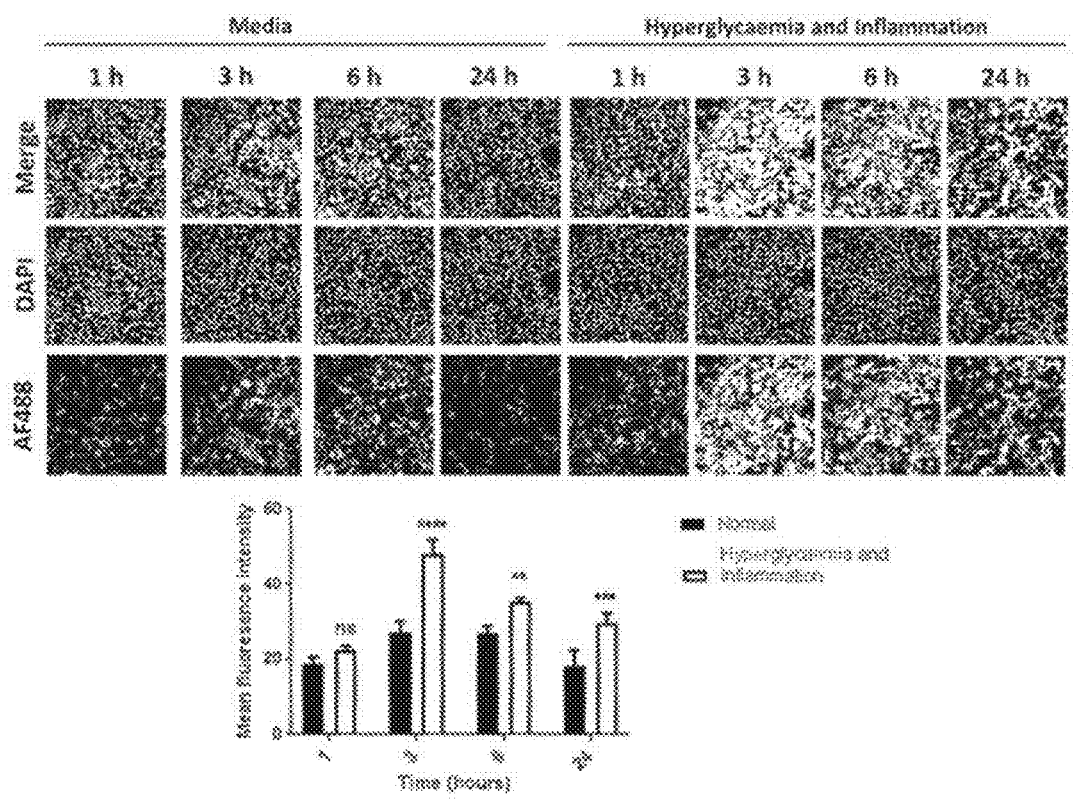

FIG. 10. Syndecan-4 expression in normal vs hyperglycaemic and inflamed ARPE-19 cells. ARPE-19 cells were exposed to either normal media or hyperglycaemia and inflammation solution for 1, 3, 6 or 24 h. The cells were labelled for Syndecan-4 and detected with Alexa Fluor 488 (AF488) (white area in AF488 panel) and nuclei were visualised by DAPI stain (white area in DAPI panel). The merge panel shows the overlap of the AF488 and DAPI panels for each treatment. Syndecan-4 expression was quantified by taking three area measurements of mean fluorescence intensity of AF488 for each treatment and plotted on a graph (bottom) (n=3; mean+SD). Two-way ANOVA was carried out with post hoc Sidak's test and significance is represented as a difference in expression from normal cells for each time point (p<0.01, *p<0.001, ****p<0.0001). Syndecan-4 levels were increased in hyperglycaemic and inflamed cells.

Figure 11:
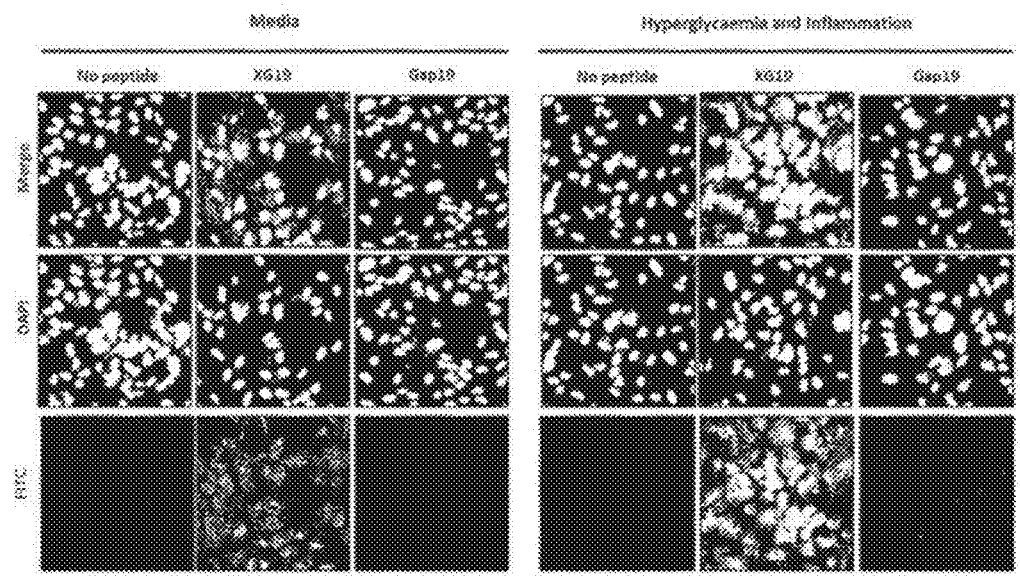

FIG. 11. Uptake of XG19 and Gap19 in normal vs hyperglycaemic and inflamed ARPE-19 cells. The uptake of XG19 and Gap19 was investigated in normal (media) and hyperglycaemic and inflamed ARPE-19 cells and was compared to the no peptide control. Peptides were FITC labelled and therefore uptake was observed by visualising FITC levels in the cytoplasm (white areas in the FITC panel) and nuclei were visualised by DAPI stain (white areas in DAPI panel). The merge panel shows the overlap of the DAPI and FITC panels for each treatment. XG19 uptake has been increased in hyperglycaemic and inflamed cells whereas there is no change in uptake of Gap19 alone.

Figure 12:
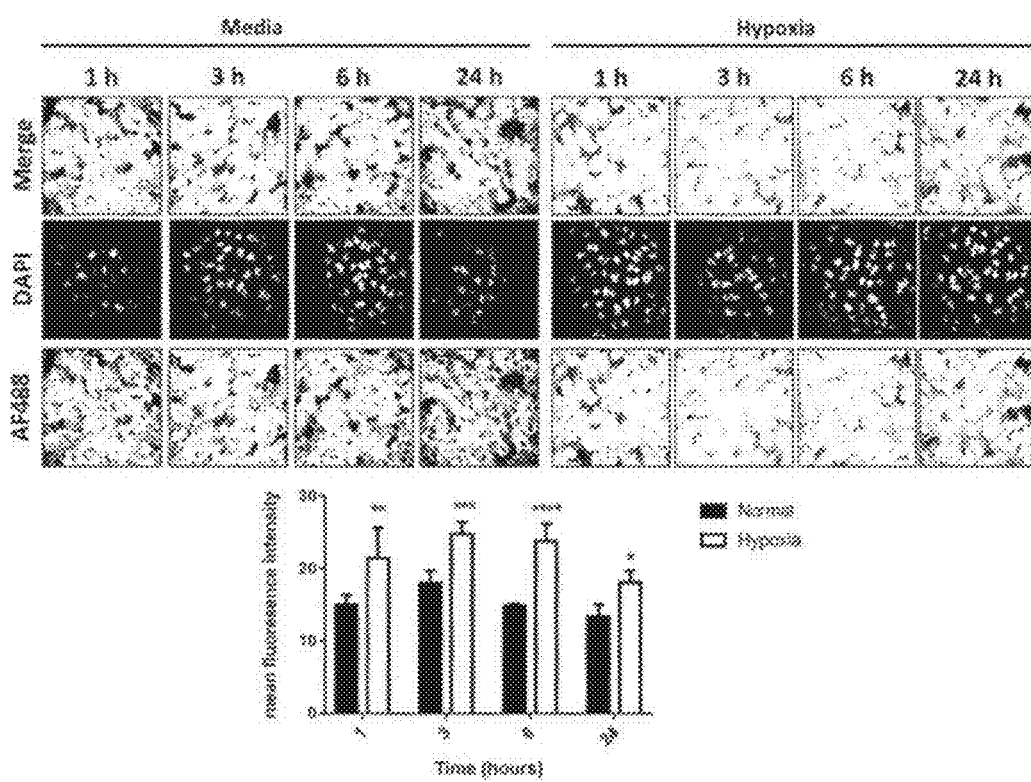

FIG. 12. Syndecan-4 expression in normal vs hypoxic ARPE-19 cells. ARPE-19 cells were exposed to either media or hypoxic solution to induce hypoxia for 1, 3, 6 or 24 h. The cells were labelled for syndecan-4 and detected with Alexa Fluor 488 (AF488) (white area in AF488 panel) and nuclei were visualised by DAPI stain (white area in DAPI panel). The merge panel shows the overlap of the AF488 and DAPI panels for each treatment. Syndecan-4 expression was quantified by taking four area measurements of mean fluorescence intensity of AF488 for each treatment and plotted on a graph (bottom) (n=4; mean+SD). Two-way ANOVA was carried out with post hoc Sidak's test and significance is represented as a difference in expression from normal cells for each time point (*p<0.05, p<0.01, *p<0.001, ****p<0.0001). Syndecan-4 levels were increased in hypoxic cells at each time point compared to normal conditions.

Figure 13:
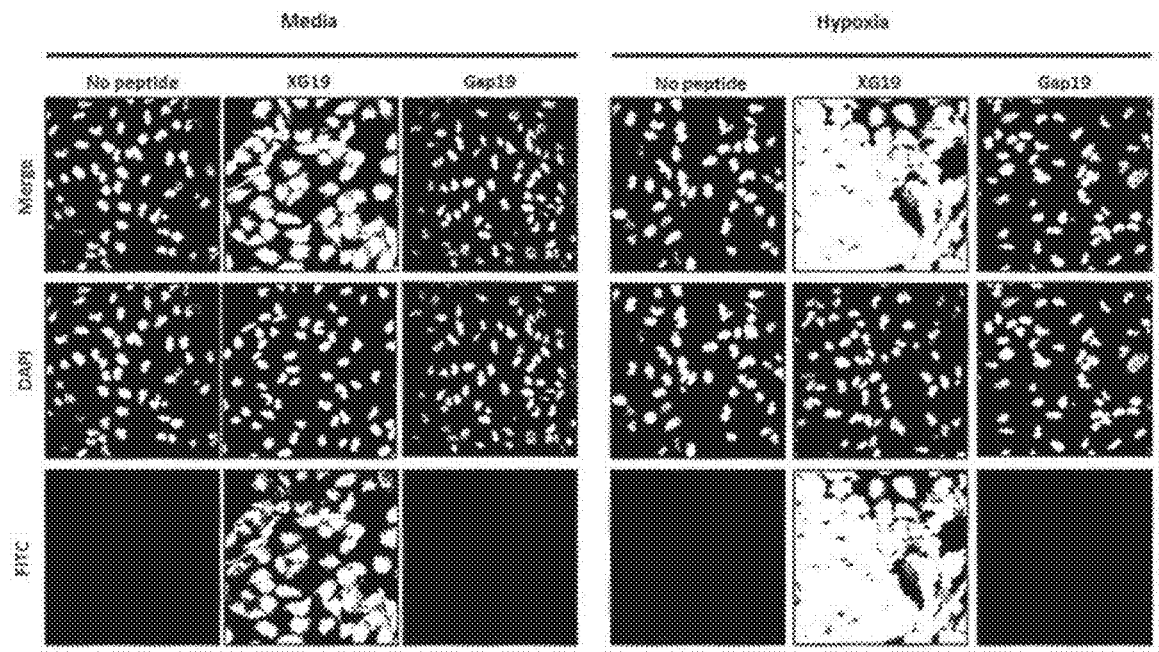

FIG. 13. Uptake of XG19 and Gap19 in hypoxic vs normal ARPE-19 cells. The uptake of XG19 and Gap19 was investigated in normal (media) and hypoxic ARPE-19 cells and was compared to the no peptide control. Peptides were FITC labelled and therefore uptake was observed by visualising FITC levels in the cytoplasm (white areas in the FITC panel) and nuclei were visualised by DAPI stain (white areas in DAPI panel). The merge panel shows the overlap of the DAPI and FITC panels for each treatment. XG19 uptake was increased significantly in hypoxic cells whereas there was no change in uptake of Gap19 alone. Therefore the increased uptake of Gap19 by hypoxic cells was dependent on the inclusion of the targeted carrier peptide.

Figure 14:
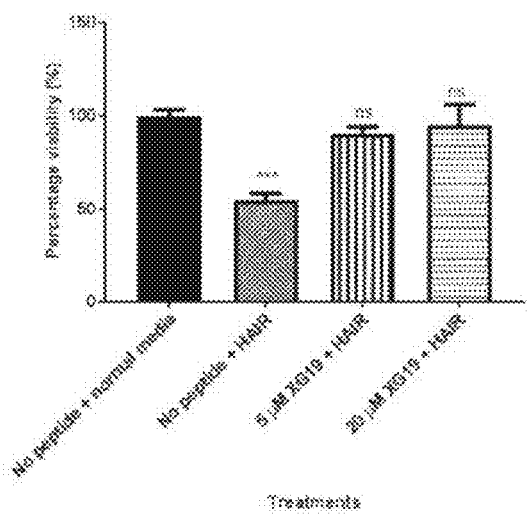

FIG. 14. XG19 maintains cell viability during hypoxia. Cells were treated with either 5 µM (vertical stripe) or 20 µM (horizontal stripes) of XG19 or were untreated (crosshatch) before making the cells hypoxic by applying HAIR solution. Cell viability was assessed by MTT assay and compared to cells in normal media as a control (black). The cell viability of XG19 treated cells was not significantly different to the untreated cells in normal media. The untreated cells in HAIR showed significantly less viability compared to the untreated cells in normal media. This showed that XG19 was able to maintain cell viability during hypoxia. One-way ANOVA was carried out with post hoc Dunnett's test and significance was represented as a difference from the untreated cells in normal media control (***$p<0.001$).

Figure 15:
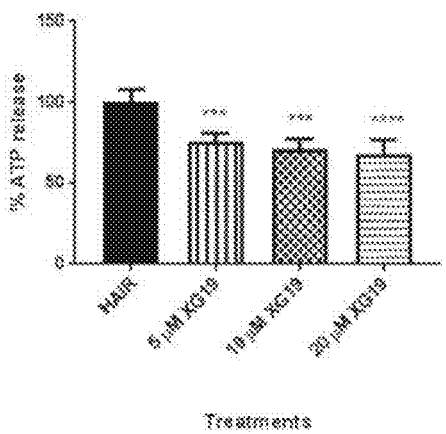

FIG. 15. XG19 inhibits Cx43 hemichannel mediated ATP release in HAIR solution. Cells were treated with 5 µM (vertical stripe), 10 µM (check pattern) or 20 µM (horizontal stripes) of XG19 or left untreated (black) before applying HAIR solution to induce hypoxia before assessing hemichannel function via the ATP release assay. All XG19 treated cells resulted in significantly less ATP release compared to untreated cells. Therefore XG19 significantly reduced ATP release during hypoxic injury by specifically inhibiting Cx43 hemichannels. One-way ANOVA was carried out with post hoc Dunett's test and significance was represented as a difference from the untreated cells in HAIR solution (*$p<0.001$, **$p<0.0001$).

Figure 16:
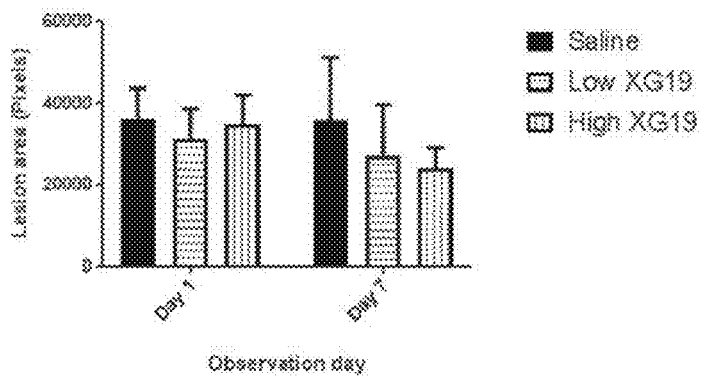

FIG. 16. Laser induced choroidal neovascularisation (CNV) mouse model fundus measurements. The lesion area was measured from fundus images acquired one day and seven days post laser induction and averaged per eye. On day 1 there were no differences between the saline (n=8 eyes), low dose (n=8 eyes) or high dose XG19 (n=7 eyes) groups. On day 7 the saline treated groups resulted in largest lesion areas while the high dose XG19 group resulted in the smallest lesion areas. This showed that XG19 was able to reduce lesion area in a dose dependent manner.

Figure 17:
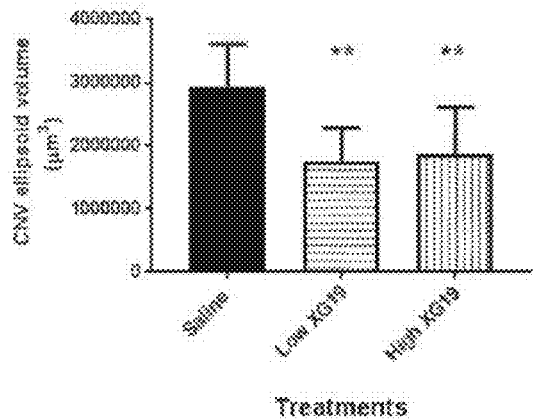

FIG. 17. Laser induced choroidal neovascularisation (CNV) mouse model Ellipsoid volume measurements. Optical coherence tomography (OCT) images acquired seven days post laser induction were measured and quantified to produce ellipsoid volume measurements of the CNV areas, and were averaged per eye. Mice treated with low dose XG19 (n=8 eyes) or high dose XG19 (n=7 eyes) resulted in significantly smaller ellipsoid volumes compared to mice treated with saline alone (n=8 eyes). One-way ANOVA was carried out with post hoc Dunnett's test and significance was represented as a difference from the saline group (**$p<0.01$, mean+SD). This figure shows that XG19 treatment reduced the CNV lesion volume.

Figure 18:
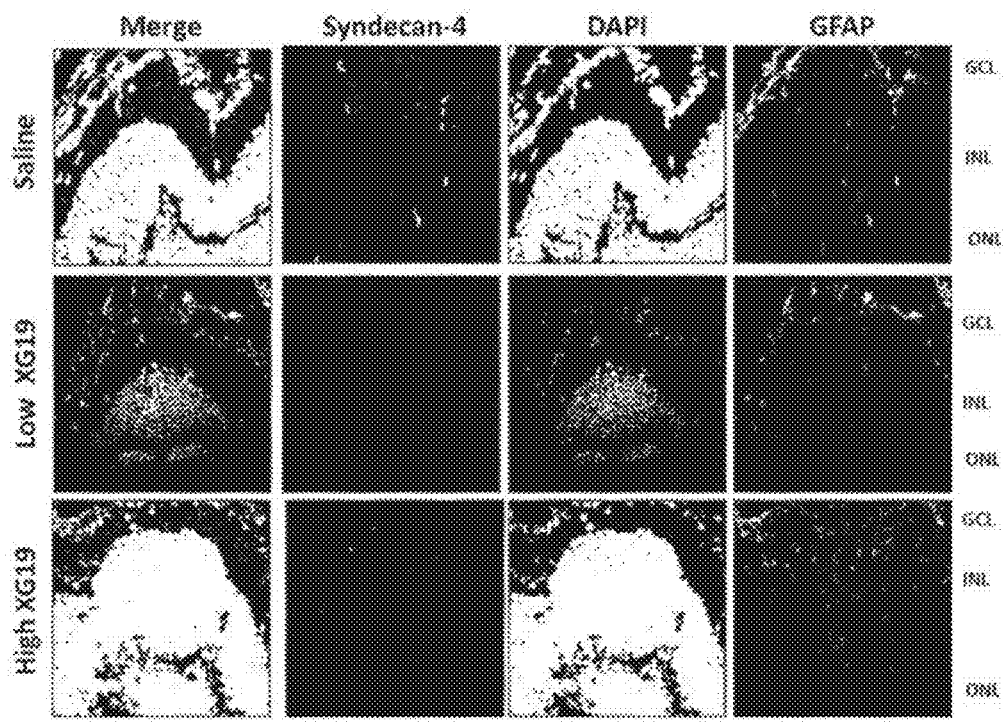

FIG. 18. Syndecan-4 and glial fibrillary acidic protein (GFAP) expression in CNV laser induced choroidal neovascularisation (CNV) mouse model tissues. Ocular tissue from mice injected with saline, low dose XG19 or high dose XG19 were labelled for Syndecan-4, GFAP and nuclei were stained with DAPI. The merged panels show labelling of GFAP, Syndecan-4 and DAPI staining of nuclei in the mouse retina orientated with the ganglion cell layer (GCL) on top inner nuclear layer in the middle (INL) and the outer nuclear layer (ONL) at the bottom of each image. The Syndecan-4 panels show the greatest amount of Syndecan-4 labelling was seen in the saline injected group extending from the GCL layer down to the ONL. GFAP labelling was seen in all groups as shown in the GFAP panels, however the labelling of GFAP in the saline injected group was more intense than in the XG19 injected groups. The elevated Syndecan-4 and GFAP expression seen in the saline injected mice suggested that these mice were experiencing retinal inflammation and ischaemia. XG19 injected mice had reduced retinal inflammation and ischaemia as indicated by the reduction of Syndecan-4 and GFAP expression and therefore showed XG19 promoted healing in a mouse model of CNV.

Figure 19:
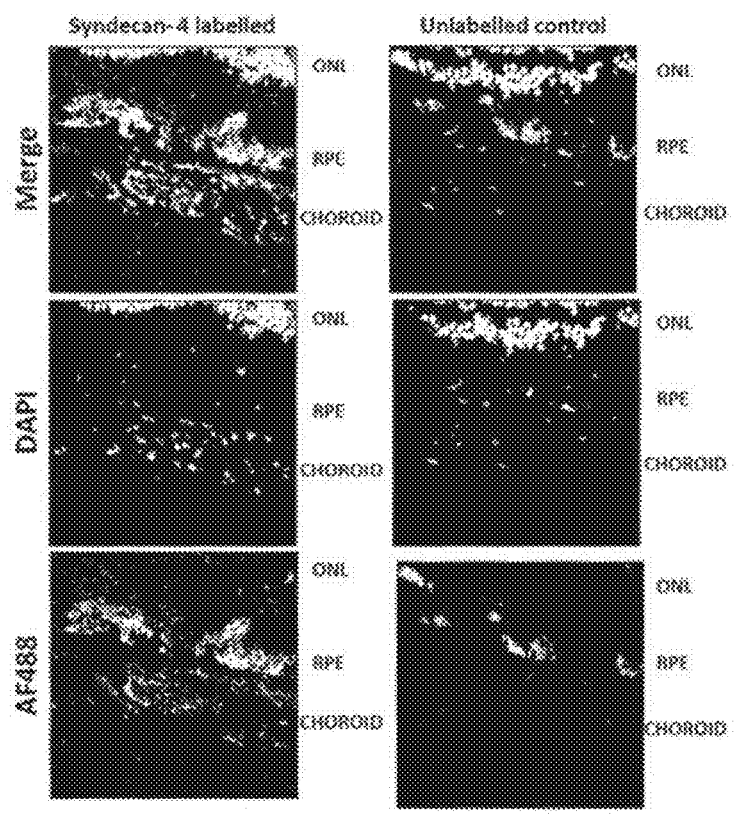

FIG. 19. Syndecan-4 expression in human retinal sections. Retinal sections from human donor tissues were either labelled for Syndecan-4 expression (left) or were unlabelled (right) as an antibody control. Syndecan-4 was detected with Alexa Fluor 488 (AF488) (white area in AF488 panel) and nuclei were visualised by DAPI stain (white area in DAPI panel). The image focusses on the outer retinal layers; outer nuclear layer (ONL), retinal pigment epithelium (RPE) and choroid. This figure shows that Syndecan-4 is present in the ocular tissues that XG19 targets, in particular around blood vessels.

Figure 20:
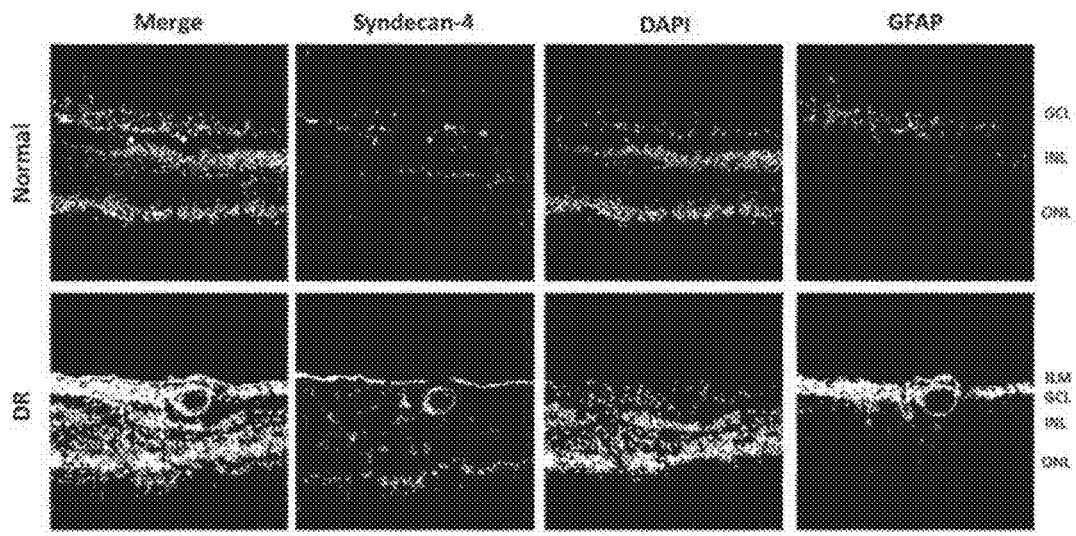

FIG. 20. Syndecan-4 and GFAP expression in the macular region of human donor tissues. The merged panel shows labelling of GFAP, Syndecan-4 and DAPI staining of nuclei in normal or diabetic retinopathy (DR) human donor tissue. The Syndecan-4 panel shows increased labelling in the DR tissue compared to normal tissue. There was elevated Syndecan-4 labelling in the ganglion cell layer (GCL), especially Müller cell endfeet, and around the blood vessel seen in the upper part of the section. The DR tissues also had a well preserved inner limiting membrane (ILM) which showed strong Syndecan-4 labelling. The GFAP panel also showed increased labelling in the DR tissue compared to the normal as seen in the GCL in the upper portion of the tissue. This was indicative of tissue injury and retinal inflammation as GFAP labels activated astrocytes and Müller cells. Syndecan-4 and GFAP expression was upregulated in DR and is an indication of tissue injury. Therefore XG19 can be used to target Syndecan-4 in these tissues to reduce retinal inflammation and ischemia.

Figure 21:
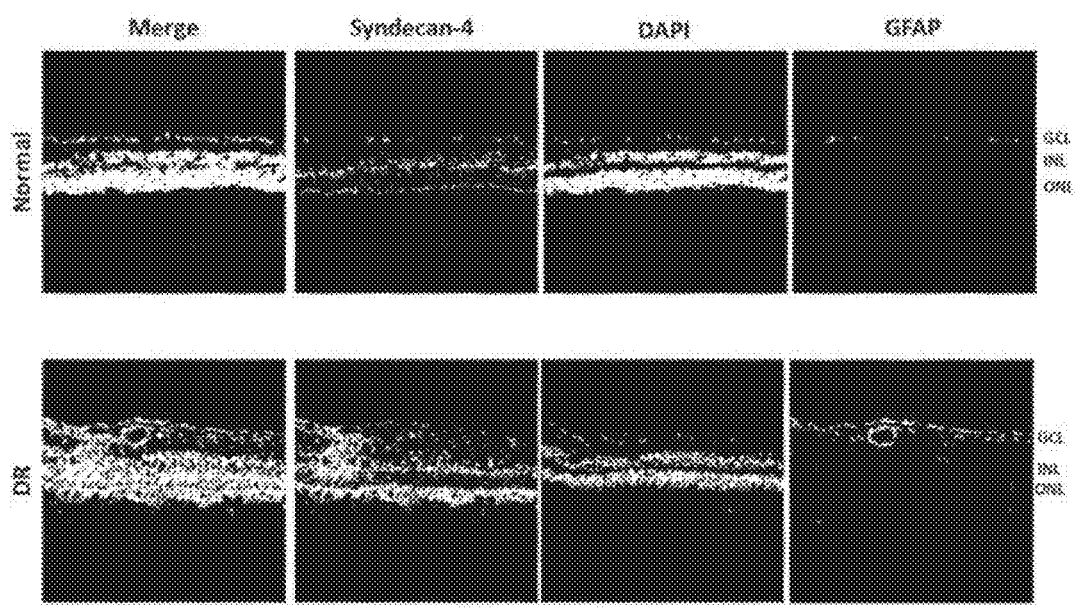

FIG. 21. Syndecan-4 and GFAP expression in the paramacular region of human donor tissues. The merged panel show labelling of GFAP, Syndecan-4 and DAPI staining of nuclei in normal or diabetic retinopathy (DR) human donor tissue. The Syndecan-4 panel showed increased labelling in the DR tissue compared to normal tissue. There was elevated Syndecan-4 labelling in the upper portion of the tissue between the GCL and INL, resulting in a dysregulation of the lower retinal layers which suggested leaky blood vessel growth in this area. The GFAP panel also showed increased labelling in the DR tissue compared to the normal as seen in the GCL in the upper portion of the tissue. This was indicative of tissue injury and retinal inflammation. Syndecan-4 and GFAP expression was upregulated in DR and was an indication of tissue injury. Therefore XG19 can be used to target Syndecan-4 in these tissues to reduce retinal inflammation and ischemia.

Figure 22:
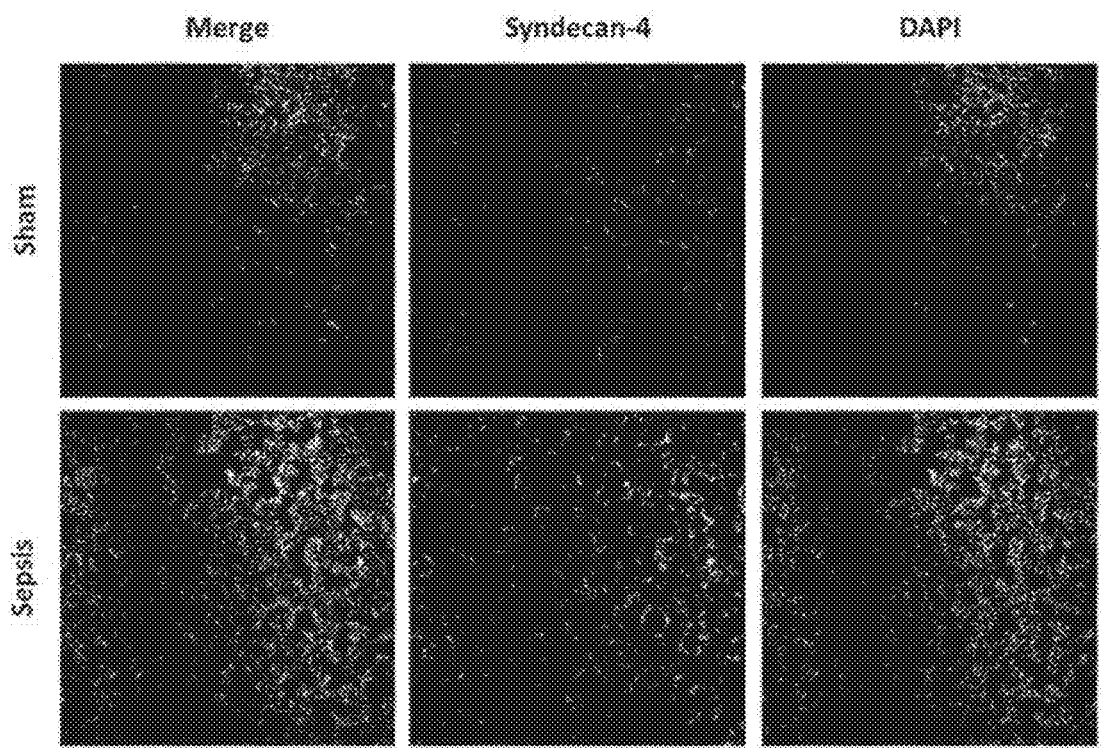

FIG. 22. Syndecan-4 expression in lung tissue of rat sepsis model. The merged panel shows labelling of Syndecan-4 and DAPI staining of nuclei in rat lung tissue from a sepsis model and compared to a sham tissue. Syndecan-4 expression as seen in the Syndecan-4 panel was lower in the sham tissue than in the sepsis tissue. The sham tissue has distinct Syndecan-4 expression around bronchioles and alveoli with weak Syndecan-4 labelling in the rest of the tissue. The sepsis tissue has strong Syndecan-4 expression throughout the section with elevated expression around the bronchioles and alveoli. This shows that the global inflammation caused by sepsis has resulted in injury in the lung tissue which is indicated by increased Syndecan-4 expression.

Figure 23:
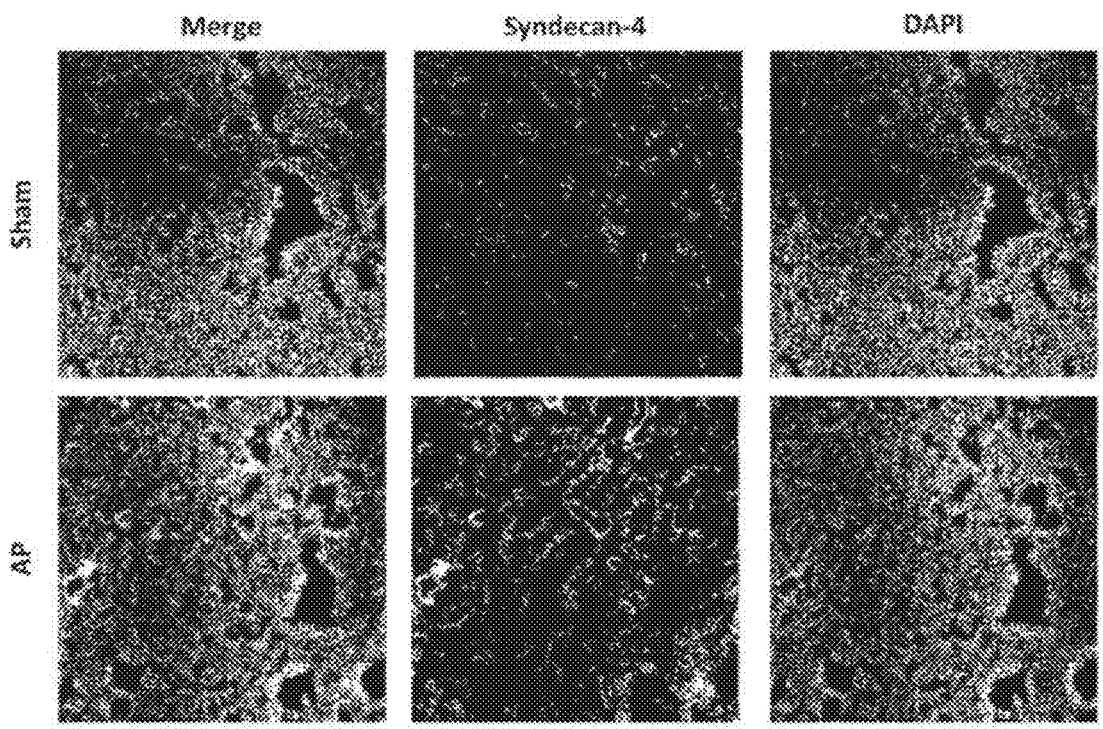

FIG. 23. Syndecan-4 expression in lung tissue of rat acute pancreatitis model. The merged panel shows labelling of Syndecan-4 and DAPI staining of nuclei in rat lung tissue from an acute pancreatitis (AP) model and compared to a sham control. Syndecan-4 expression as seen in the Syndecan-4 panel was lower in the sham tissue than in the AP tissue. The sham tissue had distinct Syndecan-4 expression around bronchioles and alveoli with weak Syndecan-4 labelling in the rest of the tissue. The AP tissue has strong Syndecan-4 expression throughout the section with elevated expression around the bronchioles and alveoli. This shows that AP results in an upregulation of Syndecan-4 in the lung.

Figure 24:
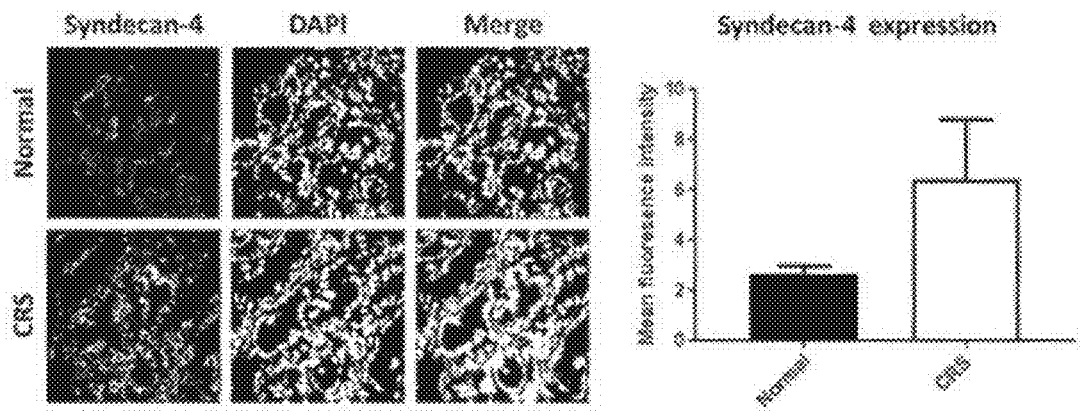

FIG. 24. Syndecan-4 labelling of normal sinus and chronic rhinosinusitis (CRS) human tissue. Confocal images of human tissue sections of normal sinus (upper panel) and chronic rhinosinusitis (lower panel), labelled for Syndecan-4 (left panel) and cell nuclei stained with DAPI (middle panel). The merged image is shown in the right panel. Images are representative of three individual tissues analysed in each group. Syndecan-4 expression of these tissues was quantified by measuring mean fluorescence intensity of each image (n=3 for each of CRS samples and 3 normals; mean+SD). This figure shows that Syndecan-4 expression is elevated in CRS tissue compared to normal.

Figure 25:
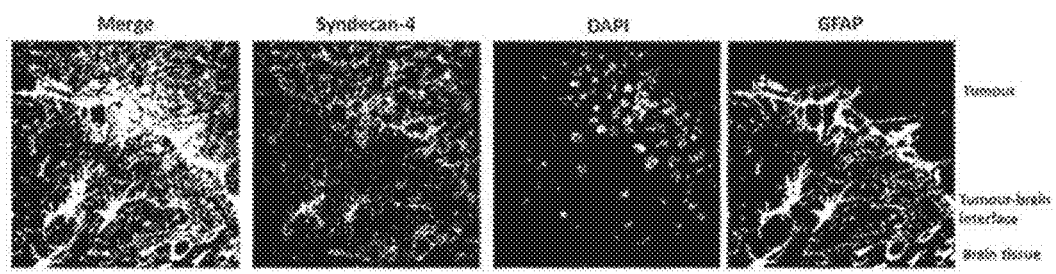

FIG. 25. Syndecan-4 and GFAP expression in mouse glioma model. The merged panel shows labelling of GFAP, Syndecan-4 and DAPI staining of nuclei at a site at which mouse brain tissue meets the tumour. The Syndecan-4 panel shows elevated Syndecan-4 labelling in the tumour tissue (upper third) relative to normal adjacent brain tissue (lower two thirds). There are also distinct areas of elevated Syndecan-4 in the brain tissue due to the tumour cells infiltrating the brain and causing inflammation in the surrounding tissue. The GFAP panel shows labelling of activated astrocytes only in the brain tissue (lower two thirds) and at the interface with the tumour. The tumour (upper one third) does not express GFAP as it does not contain astrocytes. The infiltrating tumour cells in the brain tissue is surrounded by elevated GFAP expression similar to what is seen at the interface of the brain and the tumour tissue suggesting there is inflammation and ischemia at these sites.

Figure 25A:
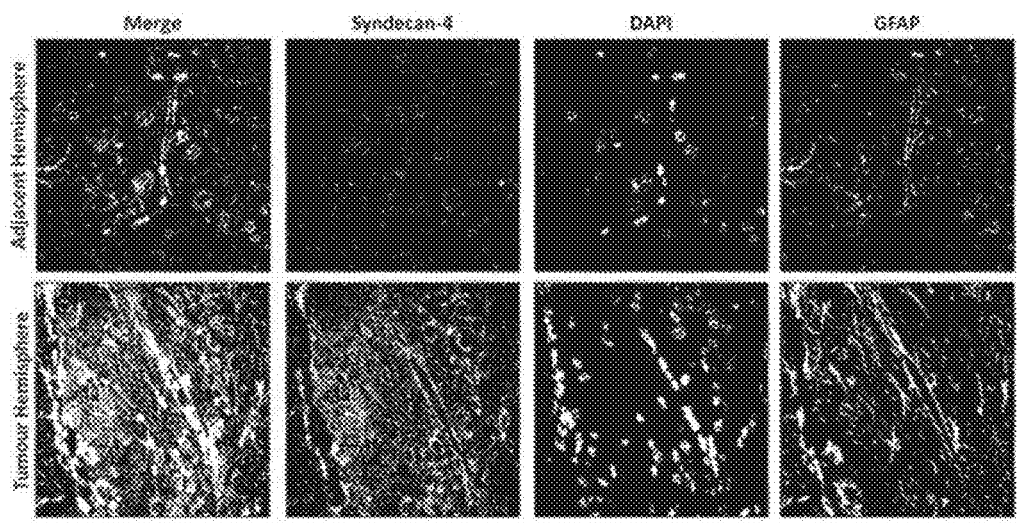

FIG. 25A. Syndecan-4 and GFAP expression in blood vessels in mouse glioma model. The merged panel shows labelling of GFAP, Syndecan-4 and DAPI staining of nuclei in the tumour hemisphere and the adjacent hemisphere. The adjacent hemisphere shows labelling of GFAP and single elongated nuclei along the blood vessel. There is weak Syndecan-4 labelling along the blood vessel and the surrounding tissue. In the tumour hemisphere there is strong Syndecan-4 labelling along the blood vessel and in the surrounding tissue. GFAP labelling was also increased in the tissue and along the blood vessels which showed this tissue was highly inflamed. Furthermore the blood vessel contains multiple nuclei in close proximity suggested the blood vessel contained proliferating cells within the blood vessel. This showed that Syndecan-4 is upregulated around blood vessels in inflamed hypoxic tissues and furthermore is expressed highly in the blood brain barrier (BBB). This suggests that constructs of the invention can be used for targeted delivery of therapeutics for brain injury.

Figure 26:
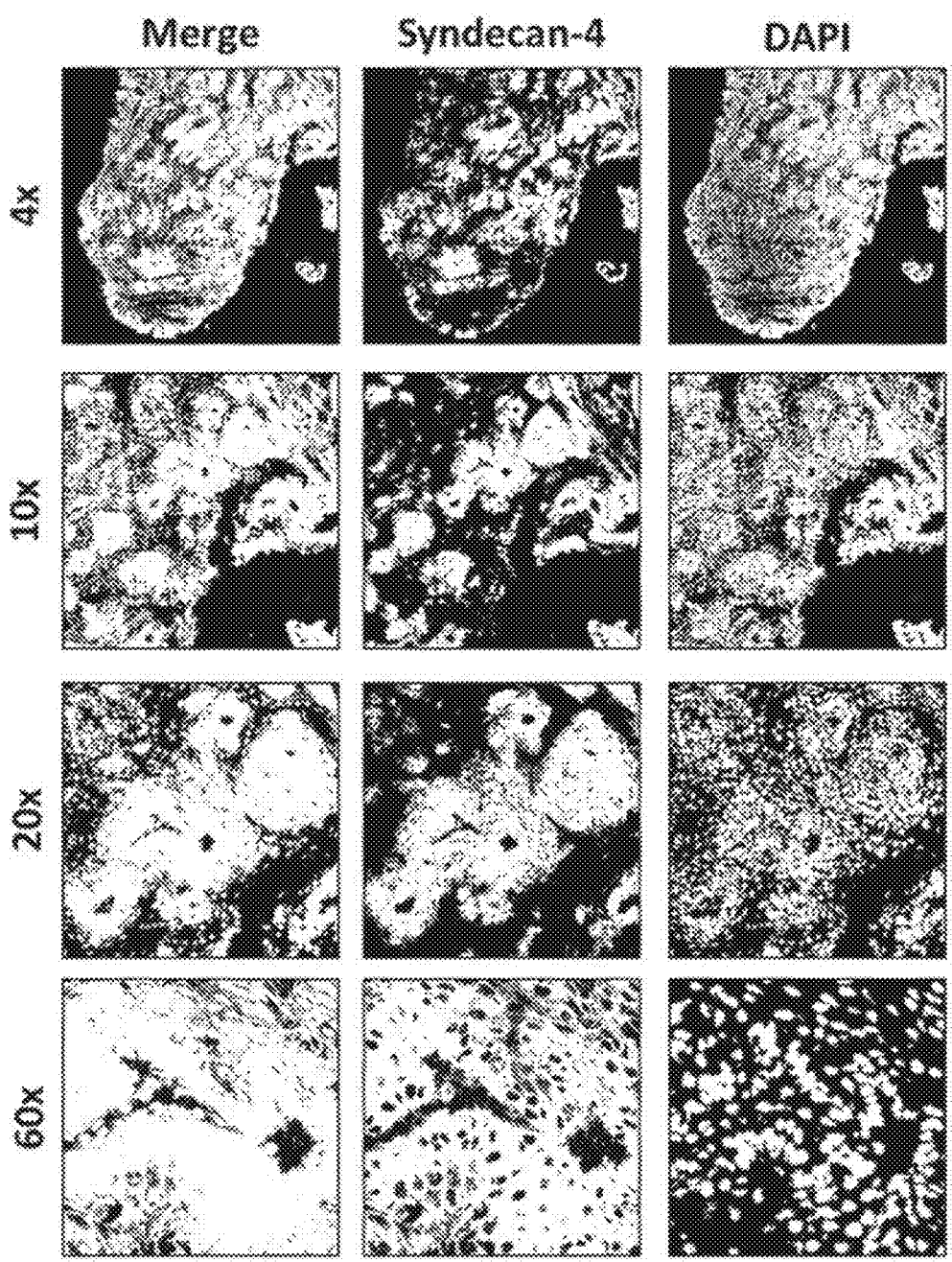

FIG. 26. Syndecan-4 expression of subcutaneous human A431 tumour in mouse flank. Sections of human A431 (epidermal carcinoma) tumour tissue grown subcutaneously in mouse flank were labelled for Syndecan-4 and nuclei were stained for DAPI. Images were taken at 4×, 10×, 20× and 60× showing that central regions of the tumour expressed very high levels of Syndecan-4. The high Syndecan-4 labelling was seen in clusters of nucleated cells.

Figure 27:
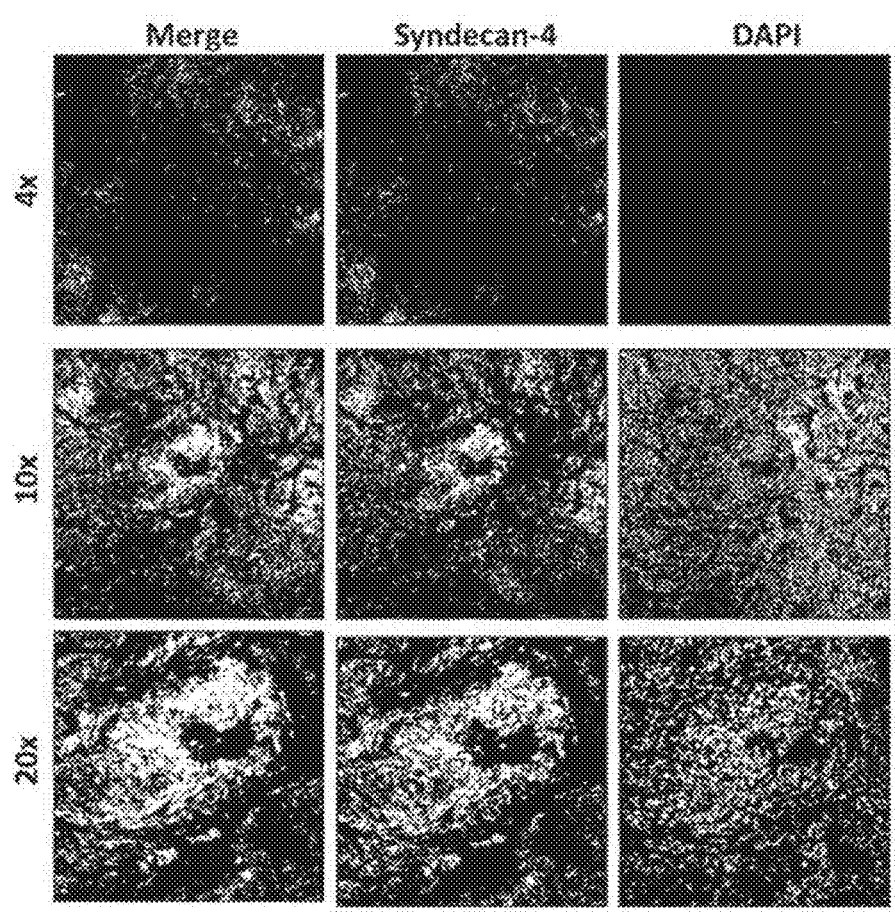

FIG. 27. Syndecan-4 expression of SKOV3 tumours. Sections of human SKOV3 tumour tissue grown subcutaneously in mouse flank were labelled for Syndecan-4 and nuclei were stained for DAPI. Images were taken at 4×, 10× and 20× showing areas of high Syndecan-4 labelling. Syndecan-4 labelling was seen in cell clusters as well as in the surrounding tissue.

PREFERRED EMBODIMENT(S)

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors have surprisingly found that a construct comprising a carrier peptide derived from the Hepatitis B virus (HBV) X-protein can be used for effective delivery of a compound to the cytoplasm of cells.

The inventors have also surprisingly found that the construct has higher uptake in hypoxic cells than non-hypoxic cells. Accordingly, the use of carrier peptides derived from the X-protein of the Hepatitis B virus will beneficially enable preferential uptake of compounds (including therapeutic agents) by hypoxic cells and tissues, i.e. targeting to hypoxic cells. This would reduce the effective drug dose required while minimising any potential off-target effects, improving efficacy and safety.

The inventors have identified that, unexpectedly, carrier peptides derived from the X-protein of the Hepatitis B virus (HBV) can be used as a targeting carrier peptides to target compounds, for example therapeutic agents, to hypoxic cells by way of constructs comprising the targeting carrier peptide and the compound. Such constructs have use in a number of applications, for both research applications and therapy, as outlined herein. In one example, such constructs have use in the treatment of diseases and disorders of the eye, and in particular, diseases and disorders of the eye associated with inflammation, hypoxia, ischemia, haemorrhage, and/or neovascularisation. Such diseases and disorders include: inflammatory ocular conditions where there is subsequent vessel die back and/or leak, including retinal vein and/or branch vein occlusion, retinal artery occlusion or retinal stroke, diabetic macular oedema, uveitis, blepharitis, severe dry eye syndrome, and optic neuritis.

Further, the inventors have found there is increased syndecan-4 expression around blood vessel endothelium in inflamed and hypoxic brain tissue, with high levels of expression in the blood brain barrier (BBB). The BBB is often a barrier to drug delivery to the central nervous system. Accordingly, constructs of the invention can be used to advantageously target delivery of therapeutic agents requiring transfer across the blood brain barrier to treat diseases and disorders of the central nervous system.

As will be appreciated, the blood retina barrier is analogous to the blood brain barrier.

In addition to the increased expression of syndecan-4 in the BBB in hypoxic and inflammatory conditions, the inventors have also found increased syndecan-4 expression in the inner limiting membrane (ILM) of the retina, which forms a barrier between the retina and the vitreous humour, in hypoxic and inflammatory conditions. The ILM often acts as a barrier for drug delivery to the retina from the vitreous humour. However, activated Müller cells at the ILM have the potential to improve drug delivery to the outer retina as the cells span the entire retina (32). For example, drug delivery systems such as nanoparticles may be endocytosed into Midler cells at the inner limiting membrane, diffuse within their intracellular space, and are then exocytosed from the Müller cells at the external limiting membrane and into the interphotoreceptor matrix (33). Accordingly, the upregulation of syndecan-4 in the ILM means constructs of the invention can be effectively delivered to the retina. Furthermore, syndencan-4 is upregulated in endothelial cells of the choroid and retina which means that constructs of the invention will be taken up by these tissues favouring transfer across the blood retina barrier.

It will be apparent to those skilled in the art that reference to a "construct" herein includes a construct in accordance with the fortieth to forty-fifth aspects of the invention as well as a construct of use in the in the first to thirty-third aspects of the invention, unless the context clearly requires otherwise.

The use of constructs comprising a targeting carrier peptide derived from the X-protein of the HBV virus is applicable to diseases and disorders that are associated with hypoxia, both in the eye and in other organs. In particular, by way of non-limiting example, use of such constructs is applicable to diseases and disorders having similar aetiology to AMD and/or diabetic retinopathy. That is, for example, disease or disorders contributed by inflammation, vascular leak resulting haemorrhaging and/or ischemia. By way of non-limiting example, the use of the construct is applicable in disorders and diseases such as heart attack, stroke, cancer, transient ischemic attacks, Alzheimer's disease, Parkinson's disease, multiple sclerosis, vascular dementia, cardiac ischemia, ischemic colitis, acute limb ischemia, cutaneous ischemia, AMD, diabetic retinopathy, retinal vein and/or branch occlusion, retinal artery occlusion, retinal stroke, macular oedema, uveitis, blepharitis, severe dry eye syndrome, or optic neuritis. Other diseases and disorders to which the invention applies will be apparent from the description herein.

In one particular example, the inventors have identified that a construct comprising Gap19, a peptide capable of interacting with an intracellular domain of connexin43, and a carrier peptide derived from the Hepatitis B virus (HBV) X-protein, can be used for effective delivery of Gap19 to the cytoplasm of human retinal pigment epithelium cells (ARPE-19) and primary human Retinal Microvascular Endothelial Cells (hMREC). The inventors have found that the construct maintains the function of Gap19 in inhibiting connexin43 (Cx43) hemichannel opening, and has an unexpectedly high uptake into cells, high efficacy, and low toxicity. Furthermore, uptake is increased in hypoxic human retinal pigment epithelium cells (ARPE-19) and hypoxic primary human Retinal Microvascular Endothelial Cells (hMREC). Without wishing to be bound by theory, this targeted carrier function appears to be facilitated by the inventors' surprising discovery that syndecan-4 is upregulated in hypoxic tissues.

Many disorders or diseases of the eye are the result of, or contributed to by, inflammation, vascular leak resulting in haemorrhaging, ischemia and/or hypoxia. In particular, many disorders or diseases of the posterior cavity of the eye are the result of, or contributed to by, inflammation, vascular leak resulting in haemorrhaging, ischemia, and/or hypoxia. Constructs of the invention have use in therapy for AMD, diabetic neuropathy, and other disease and disorders of the eye with similar aetiology (including, for example, retinal vein and/or branch vein occlusion, retinal artery occlusion or retinal stroke, diabetic macular oedema, uveitis, blepharitis, severe dry eye syndrome or optic neuritis).

Furthermore, many disorders or diseases of other organs and organ systems, in particular chronic disorders or diseases, are the result of, or contributed to by, inflammation, vascular leak resulting in haemorrhaging, ischemia and/or hypoxia. In particular, these diseases or disorders include many cancers (including for example brain glioma, ovarian cancer, hypoxic tumours in general), brain stroke, cardiovascular disease (including cardiac ischemia, pericarditis, myocardial infarction, ischemic valve disease), sepsis (including acute pancreatitis, colitis, autoimmune diseases, coeliac disease, glomerulonephritis, hepatitis, inflammatory bowel disease, pre-perfusion injury and transplant rejection)

The particular construct produced by the inventors and used in their studies has the amino acid sequence lchpv GG KQIEIKKFK (SEQ ID NO: 1), in which lowercase letters represent a D-isomer. This construct comprises the targeting carrier peptide LCLRPV (SEQ ID NO: 2) and a peptide capable of interacting with an intracellular domain of Cx43 hemichannels KQIEIKKFK (SEQ ID NO: 3), aka Gap19, connected via a GG linker. For ease of reference, the peptide of SEQ ID NO: 1 will be termed XG19.

Constructs comprising variants of the targeting carrier peptide derived from the X-protein of the Hepatitis B virus are also of use in methods of the invention, as outlined above and elsewhere herein. Constructs comprising alternative compounds for delivery to hypoxic cells are also of use in methods of the invention, as outlined above and elsewhere herein. For example, constructs comprising variant and alternative peptides capable of interacting with an intracellular domain of Cx43 are of use in the treatment of diseases and disorders of the eye as outlined above and elsewhere herein.

Accordingly, the invention comprises the use of such targeting carrier peptides derived from the X-protein of the Hepatitis B virus for targeting delivery of compounds (including therapeutic agents) to hypoxic cells. For example, peptides for targeting delivery of therapeutic agents to hypoxic cells (tissues) in subjects as well as for targeting delivery of compounds to hypoxic cells for research purposes.

Use of constructs comprising targeting carrier peptides derived from the X-protein of the Hepatitis B virus and compounds (including therapeutic agents) will mean that the compound will be able to be administered at lower doses than, for example, the native compound, reducing side effects. Furthermore, targeting a compound to hypoxic cells will reduce off-target effects and mean that more of the compound is available to the target cells.

Furthermore, nucleic acids encoding such constructs and nucleic acid vectors comprising nucleic acids encoding such constructs are of use in methods of the invention as outlined above and elsewhere herein.

Skilled persons will readily appreciate that reference to delivery of a compound to a cell, as used herein, includes delivery to the surface of a cell or delivery within a cell.

As will be appreciated, a "carrier peptide" or "cell penetrating peptide" is a peptide that facilitates cellular intake or uptake of various "cargo" by translocating the membrane, acting as a molecular delivery vehicle and functioning to deliver cargo to a cell.

As used herein the phrases "move across a cell membrane", "carry a cargo across a cell membrane", "cell membrane translocation" and like phrases, should be taken broadly to encompass transport of the carrier peptide, a compound for delivery to a cell, and/or a construct comprising a carrier peptide and compound from the outside of a cell to the inside of the cell. These phrases, and the like, should not be taken to imply a particular mode or mechanism of transport across or through the cell membrane.

As used herein, the phrase "targeting carrier peptide" and the like should be taken broadly to encompass a carrier peptide that is capable of targeting a cell or cells in a particular physiological or pathophysiological state. In this context, the term "targeting" should not be taken to mean targeting a particular cell type or cell line. In one preferred embodiment of the invention, the targeted cells are in a state of hypoxia and the carrier peptide may be termed a "hypoxia-targeting carrier peptide" or a "hypoxic cell targeting peptide".

Furthermore, it will be appreciated that a targeting peptide that is capable of being used as a carrier peptide may also be used to deliver a cargo to the surface of a cell.

As used herein, the terms "target" and "targeting" and the like should be taken to mean a preferential interaction with, binding to, or uptake by, the specified cell(s), and should not be taken to require 100% specificity.

As detailed herein, the invention provides methods of targeting delivery of a compound to hypoxic cells. In certain embodiments, the invention provides methods of targeting delivery of a compound to hypoxic cells in a mixed population of hypoxic and non-hypoxic cells.

As used herein, "hypoxic cells" refers to cells that have been exposed to a concentration of oxygen delivery that is insufficient to meet the oxygen demand of the cell. For example, a concentration of oxygen that is significantly lower than the normal physiological concentration of oxygen in a healthy well-perfused tissue. The phrase should be interpreted broadly to include circumstances where there is a reduction in oxygen delivery as well as circumstances where there is a complete lack of oxygen delivery. Preferably, the hypoxic cell exhibits upregulation of syndecan-4 as a result of the hypoxia. Hypoxia which triggers syndecan-4 upregulation may be transient, and does not need to be a sustained or particular level of hypoxia. The phrase "hypoxic cells" should be taken to include the singular, i.e. "a hypoxic cell", unless the context clearly requires otherwise.

It will be understood by those skilled in the art that "hypoxic cells" may constitute a tissue, or a part or zone of a tissue. For example, hypoxic cells may constitute a tissue with differing degrees or zones of oxygen perfusion. It should be appreciated that a tissue may be constituted of normal tissue, diseased tissue (for example tumour tissue or an inflamed tissue), or a mixture of the two. It should be appreciated that a tissue may have differing degrees or zones of oxygen perfusion due to a disease process, but this is not necessarily the case.

Delivery of constructs, nucleic acids, and/or vectors comprising nucleic acids may occur in vivo or in vitro, depending on the purposes for which delivery is required. Such methods may be used for research purposes or in the treatment of disease.

As used herein, the terms "treatment", "treating", "treated" and the like are to be considered in their broadest context. These terms do not necessarily imply that a subject is treated until total recovery. Accordingly, "treatment" broadly includes, for example, the prevention, amelioration or management of one or more symptoms of a disease or disorder, the severity of one or more symptoms, and preventing or otherwise reducing the risk of developing secondary complications.

It should be appreciated that methods of the invention may comprise administering a nucleic acid encoding a construct of the invention to a subject and/or administering a vector comprising a nucleic acid encoding a construct of the invention to a subject. Likewise, it should be appreciated that methods of the invention may comprise contacting a nucleic acid encoding a construct of the invention with a population of cells and/or contacting a vector comprising a nucleic acid encoding a construct of the invention with a population of cells.

The constructs (or nucleic acids or vectors encoding same) may be delivered to a cell by a number of different means, as will be readily appreciated by persons skilled in the art.

However, by way of example, an in vitro method may comprise bringing the construct (or nucleic acids or vectors encoding same) into contact with one or more cells or a composition comprising one or more cells, for example, contacting the construct or peptide (or nucleic acids or vectors encoding same) with a sample, composition or media in which the one or more cells are contained (such as mixing a composition of the invention with a liquid sample containing one or more cells). In another embodiment, a method of the invention comprises administering a construct (or nucleic acids or vectors encoding same) to a subject.

In one embodiment of any aspect of the invention described herein, the targeting carrier peptide comprises the amino acid sequence LCL (SEQ ID NO: 4).

In certain embodiments any aspect of the invention described herein, the targeting carrier peptide comprises an amino acid sequence selected from the group consisting of: LCLRP (SEQ ID NO: 5), LCLRPV (SEQ ID NO: 2), LCLRPVG (SEQ ID NO: 6), LCLRPVGAE (SEQ ID NO: 7), LCLRPVGAESR (SEQ ID NO: 8), LCLRPVGAESRGRPV (SEQ ID NO: 9), or LCLRPVGAESRGRPVSGPFG (SEQ ID NO:10), and functionally equivalent variants thereof.

Targeting carrier peptides of these embodiments of the invention may further comprise one or more amino acids at the C-terminus, at the N-terminus, or both. The further amino acids at the C-terminus may comprise one or more amino acid corresponding to amino acids 1 to 15 of a native HBV X-protein, such that the peptide sequence corresponds to a region of consecutive amino acids from the native HBV X-protein. The further amino acids at the N-terminus may comprise one or more amino acid corresponding to amino acids 21 to 35 of a native HBV X-protein, such that the peptide sequence corresponds to a region of consecutive amino acids from the native HBV X-protein. The further amino acids at the C- and/or N-terminus may also comprise heterologous amino acids, such that the peptide sequence of the further amino acids does not correspond to a region of consecutive amino acids from the native HBV X-protein.

In one embodiment of any aspect of the invention described herein, the targeting carrier peptide consists of the amino acid sequence LCL (SEQ ID NO: 4).

In certain embodiments of any aspect of the invention described herein, the targeting carrier peptide consists of an amino acid sequence selected from the group consisting of: LCLRP (SEQ ID NO: 5), LCLRPV (SEQ ID NO: 2), LCLRPVG (SEQ ID NO: 6), LCLRPVGAE (SEQ ID NO: 7), LCLRPVGAESR (SEQ ID NO: 8), LCLRPVGAESRGRPV (SEQ ID NO: 9), or LCLRPVGAESRGRPVSGPFG (SEQ ID NO: 10), and functionally equivalent variants thereof.

In certain embodiments of any aspect of the invention described herein, the targeting carrier peptide consists of the amino acid sequence LCLX (SEQ ID NO: 11), XLCL (SEQ ID NO: 12), or XLCLX (SEQ ID NO: 13), wherein X is any amino acid.

As mentioned above, in certain embodiments X can be any amino acid, including naturally and non-naturally occurring amino acids. In the sequence listing, X is noted to be any naturally occurring amino acid, but the invention should not be construed to be limited in this way. By way of example only, X may be chosen from G, A, V, L, I, S, C, T, M, F, Y, W, P, H, K, R, D, E, N, Q, taurine, ornithine, 5-hydroxylysine, e-N-methyllysine, and 3-methylhistidine. X may also comprise a modified amino acid, including selenocysteine, hydroxyproline, selenomethionine, hypusine, carboxylated glutamate. The primary amine group and primary carboxyl group may be modified to include nucleophilic addition, amide bond formation and imine formation for the amine group, and esterification, amide bond formation and decarboxylation for the carboxylic acid group. Certain amino acid residues may have added hydrophobic groups for membrane localization or endosome release, or have undergone myristoylation, palmitoylation, isoprenylation or prenylation, farnesylation, geranylgeranylation, glypiation, lipoylation, attachment of a flavin moiety (FMN or FAD), phosphopantetheinylation, ethanolamine phosphoglycerol attachment, acylation, N-acylation (amides), S-acylation (thioesters), acetylation, alkylation (methyl, ethyl), methylation, amidation, polyglutamylation, butyrylation, glycosylation, glycation, polysialylation, malonylation, hydroxylation, iodination, nucleotide addition (eg ADP-ribosylation), oxidation, phosphate ester (O-linked) or phosphoramidate (N-linked) formation, phosphorylation, histidine (N-linked) adenylylation, propionylation, pyroglutamate formation, S-glutathionylation, S-nitrosylation, succinylation addition, stearylation, sulfation, selenoylation, biotinylation, pegylation, citrullination, deimination, or carbamylation.

In certain embodiments of any aspect of the invention described herein, the targeting carrier peptide comprises an amino acid sequence LCLK (SEQ ID NO: 14), LCLH (SEQ ID NO: 15), LCLR (SEQ ID NO: 16), LCLE (SEQ ID NO: 17), LCLN (SEQ ID NO: 18), LCLQ (SEQ ID NO: 19), VLCLR (SEQ ID NO: 20), or LCLD (SEQ ID NO: 21). In one particular embodiment, the targeting carrier peptide comprises an L-isomer of LCLK (SEQ ID NO: 14), LCLH (SEQ ID NO: 15), LCLR (SEQ ID NO: 16), LCLE (SEQ ID NO: 17), LCLN (SEQ ID NO: 18), LCLQ (SEQ ID NO: 19), or LCLD (SEQ ID NO: 21). In one particular embodiment, the targeting carrier peptide comprises a D-isomer of VLCLR (SEQ ID NO: 20).

Targeting carrier peptides of these embodiments of the invention may further comprise one or more amino acids at the C-terminus, at the N-terminus, or both. The further amino acids at the C-terminus may comprise one or more amino acid corresponding to amino acids 1 to 15 of a native HBV X-protein, such that the peptide sequence of the further amino acids corresponds to a region of consecutive amino acids from the native HBV X-protein. The further amino acids at the N-terminus may comprise one or more amino acid corresponding to amino acids 21 to 35 of a native HBV X-protein, such that the peptide sequence of the further amino acids corresponds to a region of consecutive amino acids from the native HBV X-protein. The further amino acids at the C- and/or N-terminus may also comprise heterologous amino acids, such that the peptide sequence of the further amino acids does not correspond to a region of consecutive amino acids from the native HBV X-protein.

In certain embodiments of any aspect of the invention described herein, the targeting carrier peptide consists of the amino acid sequence LCLK (SEQ ID NO: 14), LCLH (SEQ ID NO: 15), LCLR (SEQ ID NO: 16), LCLE (SEQ ID NO: 17), LCLN (SEQ ID NO: 18), LCLQ (SEQ ID NO: 19), VLCLR (SEQ ID NO: 20), or LCLD (SEQ ID NO: 21). In one particular embodiment, the targeting carrier peptide consists of an L-isomer of LCLK (SEQ ID NO: 14), LCLH (SEQ ID NO: 15), LCLR (SEQ ID NO: 16), LCLE (SEQ ID NO: 17), LCLN (SEQ ID NO: 18), LCLQ (SEQ ID NO: 19), or LCLD (SEQ ID NO: 21). In one particular embodiment, the targeting carrier peptide consists of a D-isomer of VLCLR (SEQ ID NO: 20).

In certain embodiments of any aspect of the invention described herein, the targeting carrier peptide comprises an amino acid sequence XCXR (SEQ ID NO: 22), wherein X is any hydrophobic amino acid. In one embodiment, the targeting carrier peptide comprises the sequence ICIR (SEQ ID NO: 23) or VCVR (SEQ ID NO: 24).

Targeting carrier peptides of these embodiments of the invention may further comprise one or more amino acids at the C-terminus, at the N-terminus, or both. The further amino acids at the C-terminus may comprise one or more amino acid corresponding to amino acids 1 to 15 of a native HBV X-protein, such that the peptide sequence corresponds to a region of consecutive amino acids from the native HBV X-protein. The further amino acids at the N-terminus may comprise one or more amino acid corresponding to amino acids 21 to 35 of a native HBV X-protein, such that the peptide sequence corresponds to a region of consecutive amino acids from the native HBV X-protein. The further amino acids at the C- and/or N-terminus may also comprise heterologous amino acids, such that the peptide sequence of the further amino acids does not correspond to a region of consecutive amino acids from the native HBV X-protein.

In certain embodiments of any aspect of the invention described herein, the targeting carrier peptide consists of the amino acid sequence XCXR (SEQ ID NO: 22), wherein X is any hydrophobic amino acid. In one embodiment, the targeting carrier peptide consists of the amino acid sequence ICIR (SEQ ID NO: 23) or VCVR (SEQ ID NO: 24).

The hydrophobic amino acid of this embodiment of the invention may be naturally or non-naturally occurring or may comprise a modified amino acid (for example modified as described above). By way of example only, the hydrophobic amino acid may be chosen from L, V, I, M, F and W.

Unless otherwise specified herein, peptides of use in the invention and constructs of the invention may be composed of L-amino acids, D-amino acids or a mixture thereof, and may include non-naturally occurring amino acids.

Skilled persons will readily appreciate amino acids at positions 1 to 35 of a native X-protein, having regard to the information herein and other published sequence information. By way of example, see GenBank accession number Y18857 also provides exemplary sequence information, and the reader is specifically directed to this database by way of reference and the entry is included in the general description of the invention herein. In addition Gunther S, Fischer L, Pult I, Sterneck M, Will H. Naturally occurring variants of hepatitis B virus. Adv Virus Res. 1999; 52:25-137 provides sequence information for a number of X-proteins. Further, examples of useful sequence information is provided in Table 1, below.

Table 1

| Protein Accession No. | Locus | Sequence | SEQ ID NO |
|---|---|---|---|
| Q8I163 | HBVC8 | MAARVCCQLDPARDVLCLRPVGAESRGRPVSGPFG | 25 |
| P0C689 | HBVC5 | As above | 25 |
| P12936 | HBVC3 | As above | 25 |
| P0C686 | HBVC1 | As above | 25 |
| Q9YZR6 | HBVC2 | MAARMCCQLDPARDVLCLRPVGAESRGRPVSGPFG | 26 |
| O93195 | HBVD7 | MAARLCCQLDPARDVLCLRPVGAESRGRPFSGPFG | 27 |
| Q67863 | HBVC4 | MAARVCCQLDPARDVLCLRPVGAESRGRPVSRPFG | 28 |
| Q67877 | HBVD6 | MAARLCCQLDPARDVLCLRPVGAESRGRPFSGPLG | 29 |
| P24026 | HBVD2 | MAARLCCQLDPARDVLCLRPVGAESRGRPFSGPLG | 30 |
| P0C687 | HBVC9 | MAARLCCQLDPTRDVLCLRPVGAESRGRPVSGPLG | 31 |
| P0C681 | HBVD5 | MAARLCCQLDPARDVLCLRPVGAESRGRPFSGPLG | 32 |
| Q913A9 | HBVC7 | MAARLCCQLDPARDVLCLRPVGAESRGRPFSGPLG | 33 |
| O91531 | HBVA7 | MAARLCCQLDPSRDVLCLRPVGAESRGRPLSGPLG | 34 |
| Q9E6S8 | HBVC0 | MAARLCCQLDPARDVLCLRPVGAESRGRPVSGSLG | 35 |
| Q9PX75 | HBVB7 | MAARLCCQLDPARDVLCLRPVGAESRGRPLPGPLG | 36 |
| P20975 | HBVB2 | MAARLCCQLDPARDVLCLRPVGAESRGRPLPGPLG | 37 |
| P0C685 | HBVB3 | MAARLCCQLDPARDVLCLRPVGAESRGRPLPGPLG | 38 |
| P20976 | HBVB1 | MAARLCCQLDPARDVLCLRPVGAESRGRPLPGPLG | 39 |
| P17102 | HBVA4 | MATRLCCQLDPSRDVLCLRPVGAESRGRPLSGPLG | 40 |
| Q9PXA2 | HBVB5 | MAARLCCQLDPARDVLCLRPVGAESRGRPLPGPLG | 41 |
| P03165 | HBVD3 | MAARLCCQLDPARDVLCLRPVGAESRGRPFSGSLG | 42 |
| P20977 | HBVB4 | MAARLCCQLDPARDVLCLRPVGAESRGRPFPGPLG | 43 |
| Q99HR6 | HBVF4 | MAARMCCQLDPARDVLCLRPVGAESRGRPLPGPLG | 44 |
| Q67923 | HBVB6 | MAARVCCQLDPARDVLCLRPVGAESRGRPLPGPLG | 45 |
| P69714 | HBVA2 | MAARLYCQLDPSRDVLCLRPVGAESRGRPLSGPLG | 46 |
| P69713 | HBVA3 | MAARLYCQLDPSRDVLCLRPVGAESRGRPLSGPLG | 47 |
| Q9IBI5 | HBVG3 | MAARLCCQLDPSRDVLCLRPVSAESSGRPLPGPFG | 48 |
| P0C678 | HBVB8 | MAARLCCQLDTARDVLCLRPVGAESRGRPLPGPLG | 49 |
| Q05499 | HBVF1 | MAARMCCKLDPARDVLCLRPIGAESRGRPLPGPLG | 50 |
| Q80IU5 | HBVE4 | MAARLCCQLDPARDVLCLRPVGAESCGRPVSGSLG | 51 |
| Q8JMY3 | HBVF2 | MAARLCCQLDPARDVLCLRPVGAESRGRSLSGSLG | 52 |
| Q9J5S3 | HBVOR | MAARLCCQLDTARDVLCLRPVGAESRGRPFSGSVG | 53 |
| Q9QAX0 | HBVE3 | MAARLCCQLDPARDVLCLRPVSAESCGRPVSGSLG | 54 |
| Q69604 | HBVE1 | MAARLCCQLDPARDVLCLRPVSAESCGRPVSGSLG | 55 |
| Q4R1S9 | HBVA8 | MAARLYCQLDSSRDVLCLRPVGAESRGRPFSGPLG | 56 |
| Q91C38 | HBVA6 | MAARLYCQLDSSRDVLCLRPVGAESRGRPLAGPLG | 57 |
| Q8JMY5 | HBVH1 | MAARLCCQLDPARDVLCLRPVGAESCGRPLSWSLG | 58 |
| Q80IU8 | HBVE2 | MAARLCCQLDPARDVLCLRPVSAESCGRSVSGSLG | 59 |

Table 1-continued

| Protein Accession No. | Locus | Sequence | SEQ ID NO |
|---|---|---|---|
| P12912 | HBVCP | MAARLCCQLDTSRDVLCLRPVGAESCGRPFSGPL | 60 |
| Q69607 | HBVF6 | MAARLCCQLDPARDVLCLRPVGAESSGRTLPGSLG | 61 |
| Q8JMZ5 | HBVH3 | MAARLCCQLDPARDVLCLRPVGAESCGRPLS | 62 |
| Q8JN06 | HBVH2 | MAARLCCQLDPARDVLCLRPVGAESCGRPLS | 63 |
| P87743 | HBVGB | MAARMCCQLDPSQDVLCLRPVGAESRGRP | 64 |
| Q9YJT2 | HBVGO | MAARLCCQLDPARDVLCLRPVGAEPCRRPVSG | 65 |
| Q4R1S1 | HBVA9 | MAARLYCQLDSSRNVLCLRPVGAESCGRPLSGPVG | 66 |

Additional information regarding targeting carrier peptides of use in the present invention can be found in WO 2011/155853 and WO 2013/165262, the disclosures of which are incorporated herein by reference. The skilled reader will understand that reference in these publications to peptides for non-carrier uses are not relevant.

As outlined above, the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention provide constructs comprising a peptide capable of interacting with an intracellular domain of connexin43 (Cx43), nucleic acids encoding such constructs, nucleic acid vectors comprising nucleic acids encoding such constructs, compositions comprising same, use of same in methods of treatment, use of same methods of manufacturing medicaments, and/or use of same for treatment of diseases or disorders.

In one embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the peptide capable of interacting with an intracellular domain of Cx43 is capable of interacting with the intracellular C-terminal tail of Cx43. In one embodiment, the peptide capable of interacting with an intracellular domain of Cx43 is capable of interacting with the intracellular loop of Cx43. In one embodiment, the peptide capable of interacting with an intracellular domain of Cx43 is capable of interacting with the intracellular N-terminal tail of Cx43.

In one embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the peptide capable of interacting with an intracellular domain of Cx43 is capable of inhibiting interaction of the intracellular C-terminal tail of Cx43 with the intracellular loop of Cx43.

In one embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the peptide capable of interacting with an intracellular domain of Cx43 is capable of inhibiting Cx43 hemichannel opening, preferably without blocking gap junctions.

In one embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the peptide capable of interacting with an intracellular domain of Cx43 comprises an amino acid sequence selected from the group consisting of:

```
                                    (SEQ ID NO: 3; Gap-19)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID NO: 69)
RPSSRASSRASSRPRPDDLEI;

(SEQ ID NO: 70)
RQPICIWFPNRRKPWKKRPRPDDLEI;

(SEQ ID NO: 71)
RPRPDDLEI;

(SEQ ID NO: 72)
SRPRPDDLEI;
``` and functionally equivalent variants thereof.

Peptides capable of interacting with an intracellular domain of Cx43 of such embodiments of the invention may further comprise one or more amino acids at the C-terminus, at the N-terminus, or both. The further amino acids at the C- and/or N-terminus may comprise one or more amino acid corresponding to amino acids of a native Cx43 protein, such that the peptide sequence corresponds to a region of consecutive amino acids from a native Cx43 protein. The further amino acids at the C- and/or N-terminus may also comprise heterologous amino acids, such that the peptide sequence of the further amino acids does not correspond to a region of consecutive amino acids from the native Cx43 protein.

In one embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the peptide capable of interacting with an intracellular domain of Cx43 consists of an amino acid sequence selected from the group consisting of:

```
                                    (SEQ ID NO: 3)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;
```

RPSSRASSRASSRPRPDDLEI; (SEQ ID NO: 69)

RQPICIWFPNRRKPWKKRPRPDDLEI; (SEQ ID NO: 70)

RPRPDDLEI; (SEQ ID NO: 71)

SRPRPDDLEI; (SEQ ID NO: 72)

and functionally equivalent variants thereof.

Skilled persons will readily appreciate amino acids of a native Cx43 protein, having regard to the information herein and other published sequence information. By way of example, www.uniprot.org/uniprot/P17302 also provides exemplary sequence information, and the reader is specifically directed to this database by way of reference and the entry is included in the general description of the invention herein.

In one embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the peptide capable of interacting with an intracellular domain of Cx43 is a peptide capable of promoting gap junction coupling and/or increasing gap junctional conductance. Persons skilled in the art will readily be able to identify such peptides. By way of non-limiting example, peptides capable of interacting with an intracellular domain of Cx43 and capable of promoting gap junction coupling and/or increasing gap junctional conductance include Rotigaptide (ZP-123; N-Acetyl-D-tyrosyl-D-prolyl-(4S)-4-hydroxy-D-prolylglycyl-D-alanylglycinamide; Ac-D-Tyr-D-Pro-D-Hyp-Gly-D-Ala-Gly-NH2) and its dipeptide analogue Danegaptide (ZP-1609; (2S,4R)-1-(2-aminoacetyl)-4-benzamidopyrrolidine-2-carboxylic acid; aka GAP-134).

In one particular embodiment of the fifth, seventh, ninth, eleventh, thirteenth, fifteenth, seventeenth, nineteenth, twenty-first, twenty-third, twenty-fifth, twenty-seventh, fortieth, forty-first, forty-second, forty-third, forty-fourth and/or forty-fifth aspects of the invention, the targeting carrier peptide is LCLRPV (SEQ ID NO: 2) and the peptide capable of interacting with an intracellular domain of Cx43 is KQIEIKKFK (SEQ ID NO: 3).

However, it will be appreciated that the targeting carrier peptides described herein and the peptides capable of interacting with an intracellular domain of Cx43 described herein may be used in a construct of the invention in any suitable combination.

As used herein "inhibit", "inhibiting", "inhibition", "inhibitor", "block", "blocking", "blocker", and like terms should be taken broadly to refer to a reduction in function or activity. They should not be taken to imply complete inhibition or block of function or activity. Persons skilled in the art will readily appreciate methods that may be used to assess function and activity. However, by way of example, the methodology described in the "Examples" section may be used.

In other aspects of the invention, a targeting carrier peptide derived from the X-protein of the Hepatitis B virus is used to deliver therapeutic agents that reduce vascular haemorrhage, inflammation, and injury spread and/or promote revascularization. Such treatments can include, for example, therapeutic agents for reducing gap junction hemichannel opening (4). Therapeutic agents targeting connexin43 such as Gap19, as used in the inventors' studies, are an appropriate therapeutic agent for such a strategy. Strategies of this nature are suitable for use in tumours, where it is proposed that poor integrity rather than neovascularisation per se is an underlying cause of tumour hypoxia (5).

Accordingly, in certain embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth and/or thirty-ninth broad aspects of the invention the compound or therapeutic agent is a peptide capable of interacting with an intracellular domain of connexin43 (Cx43).

In accordance with the foregoing, it will be apparent to those skilled in the art that references to a "compound(s)" and a "therapeutic agent(s)" herein will encompass a peptide capable of interacting with an intracellular domain of connexin43 (Cx43) unless the context clearly requires otherwise.

As described above, the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention provide methods of targeting delivery of a compound to hypoxic cells in a subject, methods of treating a disease or disorder associated with hypoxia, use of constructs, nucleic acids, and nucleic acid vectors in the manufacture of a medicament, use of constructs, nucleic acids, and nucleic acid vectors for the treatment of a disease or disorder associated with hypoxia, methods of targeting delivery of a compound to hypoxic cells, methods of increasing uptake of a compound, methods of preparing a medicament for increased uptake of a compound by a hypoxic cell or cells, and methods of reducing off-target effects of a therapeutic agent involving a compound or therapeutic agent.

The compound may be any compound to be targeted for delivery to a hypoxic cell in accordance with the invention. It will be appreciated that reference herein to a "hypoxic cell" should be taken to include reference to the plural "hypoxic cells". It will be appreciated that this should also be taken to include reference to a hypoxic tissue or tissues.

In certain embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention, the compound may be a therapeutic agent of use in treating a disease or disorder associated with hypoxia or an agent of therapeutic benefit for a disease or disorder associated with hypoxia. In certain embodiments, the compound may provide a diagnostic benefit for a disease or disorder associated with hypoxia. In certain embodiments, the compound may be a compound for use in research purposes.

In certain embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention, the compound may be a nucleic acid, peptide nucleic acid, polypeptide (including for example, fusion proteins), carbohydrate, peptidomimetic, small molecule inhibitor, chemotherapeutic drug, anti-inflammatory drug, antibody, single chain Fv fragment (SCFV), lipid, proteoglycan, glycolipid, lipoprotein, glycomimetic, natural product, or fusion protein. Where the compound is a nucleic acid it may be DNA, RNA, cDNA, double-stranded, single-stranded, sense, antisense, or circular, including DNAzymes, iRNA, siRNA, miRNA, piRNA, lcRNA, and ribozymes, phagemid, aptamer for example.

It will be apparent to those skilled in the art that certain compounds (including therapeutic agents and diagnostic agents) will be desired to be delivered to hypoxic cells in certain situations. For example, for methods involving treatment of disorders or diseases associated with hypoxia the compound may be a therapeutic agent for treatment of that disease where targeting of the agent to hypoxic cells would be desirable. By way of further example, for methods involving treatment of disorders or disease associated with hypoxia the compound may be a therapeutic agent for treatment of the hypoxia per se.

For example, a targeting carrier peptide derived from the X-protein of the Hepatitis B virus can be used to deliver therapeutic agents that reduce vascular haemorrhage, inflammation, and injury spread and/or promote revascularization. Such treatments can include, for example, therapeutic agents for reducing gap junction hemichannel opening (4). Therapeutic agents targeting connexin43 such as Gap19, as used in the inventors' studies, would be an appropriate therapeutic agent for such a strategy. Strategies of this nature may be suitable for use in tumours, where it is proposed that poor integrity rather than neovascularisation per se is an underlying cause of tumour hypoxia (5).

As outlined above, in certain embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention, the compound or therapeutic agent may be a peptide capable of interacting with an intracellular domain of connexin43 (Cx43) as described elsewhere herein. In particular, in embodiments where the compound or therapeutic agent is a peptide capable of interacting with an intracellular domain of connexion43 (Cx43), it may be capable of:
  interacting with the intracellular C-terminal tail of Cx43;
  interacting with the intracellular loop of Cx43;
  interacting with the intracellular N-terminal tail of Cx43;
  inhibiting interaction of the intracellular C-terminal tail of Cx43 with the intracellular loop of Cx43; and/or
  inhibiting Cx43 hemichannel opening, preferably without blocking gap junctions.

In certain embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention the compound or therapeutic agent may be a peptide capable of interacting with an intracellular domain of Cx43 comprising an amino acid sequence selected from the group consisting of:

```
                              (SEQ ID NO: 3; Gap-19)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID NO: 69)
RPSSRASSRASSRPRPDDLEI;

(SEQ ID NO: 70)
RQPICIWFPNRRKPWKKRPRPDDLEI;

(SEQ ID NO: 71)
RPRPDDLEI;
and (SEQ ID NO: 72)
SRPRPDDLEI;
``` and functionally equivalent variants thereof.

Peptides capable of interacting with an intracellular domain of Cx43 of embodiments of the invention may further comprise one or more amino acids at the C-terminus, at the N-terminus, or both. The further amino acids at the C- and/or N-terminus may comprise one or more amino acid corresponding to amino acids of a native Cx43 protein, such that the peptide sequence corresponds to a region of consecutive amino acids from a native Cx43 protein. The further amino acids at the C- and/or N-terminus may also comprise heterologous amino acids, such that the peptide sequence of the further amino acids does not correspond to a region of consecutive amino acids from the native Cx43 protein.

In certain embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention the compound or therapeutic agent may be a peptide capable of interacting with an intracellular domain of Cx43 consisting of an amino acid sequence selected from the group consisting of:

```
                              (SEQ ID NO: 3; Gap-19)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID NO: 69)
RPSSRASSRASSRPRPDDLEI;

(SEQ ID NO: 70)
RQPICIWFPNRRKPWKKRPRPDDLEI;

(SEQ ID NO: 71)
RPRPDDLEI;
and (SEQ ID NO: 72)
SRPRPDDLEI;
``` and functionally equivalent variants thereof.

In other embodiments of the first, second, third, fourth, sixth, eighth, tenth, twelfth, fourteenth, sixteenth, eighteenth, twentieth, twenty-second, twenty-fourth, twenty-sixth, twenty-eighth, twenty-ninth, thirtieth, thirty-first, thirty-second, thirty-third, thirty-fourth, thirty-sixth, thirty-seventh, thirty-eighth, and/or thirty-ninth aspects of the invention the compound is a peptide capable of promoting gap junction coupling and/or increasing gap junctional conductance. By way of non-limiting example, peptides capable of promoting gap junction coupling and/or increasing gap junctional conductance include Rotigaptide (ZP-123; N-Acetyl-D-tyrosyl-D-prolyl-(4S)-4-hydroxy-D-prolylglycyl-D-alanylglycinamide; Ac-D-Tyr-D-Pro-D-Hyp-Gly-D-Ala-Gly-NH2) and its dipeptide analogue Danegaptide (ZP-1609; (2S,4R)-1-(2-aminoacetyl)-4-benzamidopyrrolidine-2-carboxylic acid; aka GAP-134).

By way of further example, in accordance with the first, second, third, fourth, twenty-eighth, or twenty-ninth aspects of the invention a targeting carrier peptide derived from the X-protein of the Hepatitis B virus is used to preferentially deliver cytotoxins, for example for the treatment of tumours, to hypoxic (cancerous) cells thus reducing normal, non-cancer cell exposure and therefore side effects. As a result, more potent therapeutic agents or higher doses would be able to be administered without encountering side effects. Alternatively, lower doses would be more efficiently delivered to the target tissue, reducing side effects and off-target effects.

For example, for methods involving treatment of cancer the compound (or therapeutic agent) may be surface acting or cytoplasmic acting toxins for targeting to hypoxic tumour cells. For example, surface acting toxins include the fish toxin pardoxin (or active portions thereof), enzymes of lipid metabolism (PLA2, PLC), those acting membrane ion channel function (such as α-scorpion toxin or dendrotoxins or active portions thereof), or those acting on tyrosine kinase receptors (such as α-S. aureus or active portions thereof). For example, cytoplasmic acting toxins may include those targeting the mitochondrial respiratory system (rotenone), nucleic acids (mycotoxins or active portions thereof), the ribosome (diphtheria or active portions thereof) of vesicular release (botulinum tetanus or active portions thereof).

Specific examples of compounds of use in methods involving treatment of cancer include:
Temozolomide, an alkylating agent, for treatment of brain cancers; as a second-line treatment for astrocytoma and a first-line treatment for glioblastoma multiforme (brain glioma);
Docetaxel for breast cancer;
5-fluorouracil for breast cancer, stomach cancer and colorectal cancer;
Doxorubicin for breast cancer, lung cancer, bladder cancer or Hodgkin's and non-Hodgkin's lymphoma.

Skilled persons will appreciate that one or more of the foregoing compounds may be used in combination. By way of non-limiting examples, the combinations of compounds identified in Table 2 may be used.

TABLE 2

Combination chemotherapy

| Indication | Compounds | Regimen name |
|---|---|---|
| Breast cancer | Cyclophosphamide, methotrexate, 5-fluorouracil | CMF |
| | Doxorubicin, cyclophosphamide | AC |
| Hodgkin's lymphoma | Docetaxel, doxorubicin, cyclophosphamide | TAC |
| | Doxorubicin, bleomycin, vinblastine, dacarbazine | ABVD |
| | Mustine, vincristine, procarbazine, prednisolone | MOPP |
| Non-Hodgkin's lymphoma | Cyclophosphamide, doxorubicin, vincristine, prednisolone | CHOP |
| Germ cell tumor | Bleomycin, etoposide, cisplatin | BEP |

TABLE 2-continued

Combination chemotherapy

| Indication | Compounds | Regimen name |
|---|---|---|
| Stomach cancer | Epirubicin, cisplatin, 5-fluorouracil | ECF |
| | Epirubicin, cisplatin, capecitabine | ECX |
| Bladder cancer | Methotrexate, vincristine, doxorubicin, cisplatin | MVAC |
| Lung cancer | Cyclophosphamide, doxorubicin, vincristine | CAV |
| Colorectal cancer | 5-fluorouracil, folinic acid, oxaliplatin | FOLFOX |

Those skilled in the art will readily be able to identify further compounds or therapeutic agents suitable for use in methods involving treatment of cancer.

In addition to delivery of active compounds, for which constructs of the invention would be particular useful, it will be appreciated that compounds (or therapeutic agents) of the invention could be prodrugs or activatable drugs. For example, a targeting carrier peptide derived from the X-protein of the Hepatitis B virus can be used to target a hypoxia-activated prodrug for treatment of a tumour, concentrating the prodrug to a hypoxia tissue to allow for lower dosing. Such prodrugs include aromatic nitro hypoxia activated prodrugs, such as evofosfamide, tarloxotinib, PR-104 or nitroCBI, and N-oxide hypoxia activated prodrugs such as tirapazamine, or SN30000. These drugs are "activated in tumours by a process that is initiated by enzymatic one-electron reduction to yield a prodrug radical anion" (25).

In another example, in accordance with the fourth, sixth, and/or eighth aspects of the invention constructs comprising (a) a targeting carrier peptide derived from the X-protein of the Hepatitis B virus and (b) a peptide capable of interacting with an intracellular domain of connexin43 (Cx43) are used in the treatment of cancer, and in particular for blocking tumour growth. Tumours (such as in cancer) have poor vascular supply and are hypoxic and/or have portions or zones that are hypoxic, resulting in tissue with reduced oxygen levels. In the case of tumours, continued ischemia can promote the survival of hypoxia-resistant tumour cells over normal cells. Structural abnormalities in tumour blood vessels may influence therapeutic responses to treatments.

Without wishing to be bound by theory, it is believed that transient block of connexin43 hemichannels using constructs of the invention reduces vessel leak, promote normal vascularisation, protect, maintain, and/or restore vasculature, and block tumour growth and promote tissue recovery. Further, these outcomes will lead to improved outcomes from treatment with cytotoxic chemotherapeutic agents and/or radiation therapy.

Accordingly, in one embodiment the invention provides a method of treating cancer comprising: administering to a subject a construct comprising (a) a targeting carrier peptide derived from the X-protein of the Hepatitis B virus and (b) a peptide capable of interacting with an intracellular domain of connexin43 (Cx43). In a further embodiment, the invention provides a method of treating cancer comprising: administering to a subject a nucleic acid encoding a construct comprising (a) a targeting carrier peptide derived from the X-protein of the Hepatitis B virus and (b) a peptide capable of interacting with an intracellular domain of connexin43 (Cx43). In a further embodiment, the invention provides a method of treating cancer comprising: administering to a subject a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43). In other embodiments the invention also provides methods of treating cancer comprising administering a composition comprising a construct, nucleic acid, or nucleic acid vector as described in combination with one or more carrier, excipient, and/or diluent.

Accordingly, in another embodiment the invention provides the use of a construct comprising (a) a targeting carrier peptide derived from the X-protein of the Hepatitis B virus and (b) a peptide capable of interacting with an intracellular domain of connexin43 (Cx43) in the manufacture of a medicament for treating cancer. In a further embodiment the invention provides the use of a nucleic acid encoding a construct comprising (a) a targeting carrier peptide derived from the X-protein of the Hepatitis B virus and (b) a peptide capable of interacting with an intracellular domain of connexin43 (Cx43) in the manufacture of a medicament for treating cancer. In a further embodiment the invention provides the use of a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) in the manufacture of a medicament for treating cancer.

Accordingly, in another embodiment the invention provides the use of a construct comprising (a) a targeting carrier peptide derived from the X-protein of the Hepatitis B virus and (b) a peptide capable of interacting with an intracellular domain of connexin43 (Cx43) for treating cancer. In a further embodiment, the invention provides the use of a nucleic acid encoding a construct comprising (a) a targeting carrier peptide derived from the X-protein of the Hepatitis B virus and (b) a peptide capable of interacting with an intracellular domain of connexin43 (Cx43) for treating cancer. In a further embodiment, the invention provides the use of a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) for treating cancer.

In certain embodiments the cancer is a brain glioma (glioblastoma), astrocytoma, ovarian carcinoma, epidermal carcinoma, breast cancer, stomach cancer, germ cell tumour, colorectal cancer, lung cancer, bladder cancer, Hodgkin's lymphoma, non-Hodgkin's lymphoma.

In certain embodiments the treatment of cancer involves reducing tumour growth. In other embodiments the treatment of cancer involves reduction of vascular leak. In other embodiments the treatment of cancer involves promotion of normal vascularisation. In other embodiments the treatment of cancer involves protection, maintenance and/or restoration of vasculature.

In another example, in accordance with the fourth, sixth, and/or eighth aspects of the invention a targeting carrier peptide derived from the X-protein of the Hepatitis B virus can be used to treat "secondary" disease processes stemming from conditions of hypoxia. For example, protective agents would be preferentially delivered to hypoxic cells to prevent or ameliorate further cell injury. Use of a peptide compound capable of interacting with an intracellular domain of Cx43 is one example of such a strategy.

By way of non-limiting example, in accordance with the fourth, sixth, and/or eighth aspects of the invention neuroprotective agents could be used in the case of stroke. Examples of neuroprotective agents of use in the invention include compounds targeting excitotoxicity (such as NMDA antagonists), antioxidants, free radical scavengers, agents that reduce proinflammatory response of neuroglia, and agents that enhance anti-inflammatory response of neuroglia.

By way of further non-limiting example, neurorepair agents could be used in the case of stroke, muscular dystrophy, multiple sclerosis, amyloid lateral sclerosis.

In another example, for methods involving treatment of stroke in accordance with the fourth, sixth, and/or eighth aspects of the invention the compound (or therapeutic agent) may be a tissue plasminogen activator (tPA) or recombinant tissue plasminogen activator (rtPA). For example, the rtPA may be alteplase (Activase, Actilyse), reteplase (Retavase, Rapilysin), tenecteplase (TNKase), or desmoteplase.

By way of further non-limiting example, for methods involving treatment of myocardial infarction stroke in accordance with the fourth, sixth, and/or eighth aspects of the invention the compound (or therapeutic agent) may be a tissue plasminogen activator (tPA) or recombinant tissue plasminogen activator (rtPA). For example, the rtPA may be alteplase (Activase, Actilyse), reteplase (Retavase, Rapilysin), tenecteplase (TNKase), or desmoteplase.

Targeting to hypoxic cells in accordance with the invention would reduce side effects and off-target effects to normal (non-hypoxic) cells and tissues. As a result, more potent therapeutic agents or higher doses can be administered without encountering side effects. Alternatively, lower doses would be more efficiently delivered to the target tissue, reducing side effects and off-target effects.

In another example, constructs comprising (a) a targeting carrier peptide derived from the X-protein of the Hepatitis B virus and (b) a peptide capable of interacting with an intracellular domain of connexin43 (Cx43) are of use in the treatment of stroke, in particular ischemic stroke, and more particularly to promote neuronal survival after stroke.

Without wishing to be bound by theory, it is understood that transient block of connexin43 hemichannels reduces vessel leak and promote neuronal survival after ischaemic stroke through prevention of lesion spread and vascular disruption minimising reperfusion damage and enhancing functional recovery. As described herein the inventors have surprisingly found that constructs of the invention are preferentially delivered to hypoxic cells and are not sequestered by circulating blood cells. This will result in rapid targeted delivery to hypoxic cells, which is advantageous as treatment of stroke is time-critical. This is in addition to the beneficial reduction of off-target effects as described elsewhere herein. The inventors observe successful retinal administration. This will translate to efficient delivery across the blood-brain-barrier. Furthermore, as outlined above, the inventors observe increased syndecan-4 expression around blood vessel endothelium in inflamed and hypoxic brain tissue, with high levels of expression in the blood brain barrier. Therefore, constructs of the invention can be used to target drug delivery to the central nervous system.

Accordingly, in one embodiment the invention provides a method of treating stroke comprising: administering to a subject a construct comprising (a) a targeting carrier peptide derived from the X-protein of the Hepatitis B virus and (b) a peptide capable of interacting with an intracellular domain of connexin43 (Cx43). In a further embodiment, the invention provides a method of treating stroke comprising: administering to a subject a nucleic acid encoding a construct comprising (a) a targeting carrier peptide derived from the X-protein of the Hepatitis B virus and (b) a peptide capable of interacting with an intracellular domain of connexin43 (Cx43). In a further embodiment, the invention provides a method of treating stroke comprising: administering to a subject a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43). In other embodiments the invention also provides methods of treating stroke comprising administering a composition comprising a construct, nucleic acid, or nucleic acid vector as described in combination with one or more carrier, excipient, and/or diluent.

Accordingly, in another embodiment the invention provides the use of a construct comprising (a) a targeting carrier peptide derived from the X-protein of the Hepatitis B virus and (b) a peptide capable of interacting with an intracellular domain of connexin43 (Cx43) in the manufacture of a medicament for treating stroke. In a further embodiment the invention provides the use of a nucleic acid encoding a construct comprising (a) a targeting carrier peptide derived from the X-protein of the Hepatitis B virus and (b) a peptide capable of interacting with an intracellular domain of connexin43 (Cx43) in the manufacture of a medicament for treating stroke. In a further embodiment the invention provides the use of a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) in the manufacture of a medicament for treating stroke.

Accordingly, in another embodiment the invention provides the use of a construct comprising (a) a targeting carrier peptide derived from the X-protein of the Hepatitis B virus and (b) a peptide capable of interacting with an intracellular domain of connexin43 (Cx43) for treating stroke. In a further embodiment, the invention provides the use of a nucleic acid encoding a construct comprising (a) a targeting carrier peptide derived from the X-protein of the Hepatitis B virus and (b) a peptide capable of interacting with an intracellular domain of connexin43 (Cx43) for treating stroke. In a further embodiment, the invention provides the use of a nucleic acid vector comprising a nucleic acid encoding a construct comprising (a) a targeting carrier peptide derived from the X-protein of the Hepatitis B virus and (b) a peptide capable of interacting with an intracellular domain of connexin43 (Cx43) for treating stroke.

In certain examples the stroke is ischemic stroke. In other examples, the treatment of stroke is the promotion neuronal survival after stroke, in particular ischemic stroke.

In another example, tPA is co-administered with a construct comprising (a) a targeting carrier peptide derived from the X-protein of the Hepatitis B virus and (b) a peptide capable of interacting with an intracellular domain of connexin43 (Cx43) in accordance with the fourth aspect of the invention. Administration of a construct comprising (a) a targeting carrier peptide derived from the X-protein of the Hepatitis B virus and (b) a peptide capable of interacting with an intracellular domain of connexin43 (Cx43) can extend the therapeutic window of tPA through reduced vessel leak preventing of lesion spread and vascular disruption.

By way of further non-limiting example, sepsis is associated with hypoperfusion and the invention provides that a targeting carrier peptide derived from the X-protein can be used to deliver an antibacterial or antifungal agent to hypoxic (hypoperfused) cells at sites of infection.

Targeting to hypoxic cells in accordance with the invention will reduce side effects and off-target effects to normal (non-hypoxic) cells and tissues. As a result, more potent therapeutic agents or higher doses would be able to be administered without encountering side effects. Alternatively, lower doses would be more efficiently delivered to the target tissue, reducing side effects and off-target effects.

Skilled persons may readily appreciate further examples of compounds (including therapeutic agents) of use in accordance with the invention.

As noted above, the invention includes functionally equivalent variants of peptides of use in the invention, for example functionally equivalent variants of the targeting carrier peptide and/or a peptide capable of interacting with an intracellular domain of connexin43.

The phrase "functionally equivalent variants" as used herein, includes those peptides in which one or more conservative amino acid substitutions have been made, while substantially retaining the desired function of the peptide. As used herein, a "functionally equivalent variant" of a peptide is intended to include fragments of the peptide or variants of the peptide in which one or more amino acid has been deleted or added, provided such variants retain at least a level of the desired activity of the protein or peptide of which they are a variant.

By way of example, in the case of targeting carrier peptides, the peptide and a functionally equivalent variant thereof will have the ability to (a) move across a cell membrane to enter a cell, preferably carrying the compound or the therapeutic agent or the peptide capable of interacting with an intracellular domain of connexin43 (Cx43) across a cell membrane and (b) the ability to target a cell or cells in a particular physiological or pathophysiological state, preferably cells in a state of hypoxia.

Furthermore, it will be appreciated that a targeting peptide that is capable of being used as a carrier peptide may also be used to deliver a cargo to the surface of a cell.

A peptide(s) of use in the invention and its functionally equivalent variant(s) may be referred to herein collectively as "peptide(s)". Accordingly, where not specifically mentioned, references to a "peptide" or "peptides" of use in the invention herein should be taken to include reference to functionally equivalent variants thereof.

It should be appreciated that a "functionally equivalent variant" may have a level of activity higher or lower than the peptide of which it is a variant. In various embodiments of the invention a functionally equivalent variant has at least 50%, at least 60%, at least 70%, at least 80%, at least 90%, at least 95% or at least 99% of the level of activity of the peptide of which it is a variant.

Skilled persons will readily appreciate the desired function and be able to assess function and determine the level of activity of a peptide or functionally equivalent variant thereof, based on the information contained herein and using techniques known in the art.

By way of example, in the case of a targeting carrier peptide, the peptide or variant will have (a) the ability to move across a cell membrane to enter a cell, preferably carrying the compound across a cell membrane and (b) the ability to target a cell or cells in a particular physiological or pathophysiological state, preferably cells in a state of hypoxia. This function and the level of activity may be assessed based on uptake of the variant (preferably, constructs comprising the variant) into the cell, for example, using the techniques described in the "Examples" section.

By way of example, in the case of peptides capable of interacting with an intracellular domain of connexin43

(Cx43), the peptide and a functionally equivalent variant thereof will have the ability to interact with an intracellular domain of connexin43. In the case of peptides capable of inhibiting interaction of the intracellular C-terminal tail of Cx43 with the intracellular loop of Cx43, the peptide and a functionally equivalent variant thereof will have the ability to inhibit interaction of the intracellular C-terminal tail of Cx43 with the intracellular loop of Cx43. In the case of peptides capable of inhibiting Cx43 hemichannel opening, the peptide and a functionally equivalent variant thereof will have the ability to inhibit Cx43 hemichannel opening. This function and the level of activity may be assessed, for example, using the techniques described in the "Examples" section.

As used herein "conservative amino acid substitution(s)" should be taken broadly to mean substitution of amino acids that have similar biochemical properties. Persons skilled in the art will appreciate appropriate conservative amino acid substitutions based on the relative similarity between different amino acids, including the similarity of the amino-acid side chain substituents (for example, their size, charge, hydrophilicity, hydrophobicity and the like). By way of example, a conservative substitution includes: substitution of one aliphatic amino acid for another aliphatic amino acid, substitution of an amino acid with a hydroxyl- or sulphur-containing side chain with another amino acid with a hydroxyl- or sulphur-containing side chain, substitution of an aromatic amino acid with another aromatic amino acid, substitution of a basic amino acid with another basic amino acid, or substitution of an acidic amino acid with another acid amino acid. By way of further example, "conservative amino acid substitution(s)" include:

substitution of Glycine, Alanine, Valine, Leucine, or Isoleucine, one for another;
   substitution of Serine, Cysteine, Threonine, or Methionine, one for another;
   substitution of Phenylalanine, Tyrosine, or Tryptophan, one or another;
   substitution of Histidine, Lysine, or Arginine, one for another; and
   substitution of Aspartic acid, Glutamic acid, Asparagine or Glutamine, one for another.

Functionally equivalent variants containing amino acid substitutions in accordance with the invention will preferably retain at least 70%, 80%, 90%, 95% or 99% amino acid sequence similarity to the original peptide. In one embodiment, the functionally equivalent variant has at least 70%, 80% 90%, 95% or 99% sequence identity with the original peptide.

Peptides of use in the invention (including functionally equivalent variants) and constructs of the invention may be composed of L-amino acids, D-amino acids, or a mixture thereof, and may include non-naturally occurring amino acids. In particular, D-isomeric forms of peptides of use according to the invention can be produced by chemical peptide synthesis. In certain embodiments of the invention, D-isomeric forms of the targeting carrier peptide and/or the peptide capable of interacting with an intracellular domain of Cx43 may be preferred. For example, D-isomers may be preferred as they are more resistant to proteases. In other embodiments of the invention, L-isomeric forms of the targeting carrier peptide and/or the peptide capable of interacting with an intracellular domain of Cx43 may be preferred. For example, L-isomers may be preferred as they more closely mimic naturally occurring peptides. Persons skilled in the art will readily recognise appropriate use of D- and L-isomers.

It should be understood that peptides of use in the invention, or a construct of the invention being a fusion peptide, (including functionally equivalent variants), are "isolated" or "purified" peptides. An "isolated" or "purified" peptide is one which has been identified and separated from the environment in which it naturally resides, or artificially synthesized. It should be appreciated that these terms do not reflect the extent to which the peptide has been purified or separated from an environment in which it naturally resides.

A peptide of use in the invention, or a construct of the invention being a fusion peptide, may be isolated from natural sources, or preferably derived by chemical synthesis (for example, fmoc solid phase peptide synthesis as described in Fields G B, Lauer-Fields J L, Liu R Q and Barany G (2002) Principles and Practice of Solid-Phase peptide Synthesis; Grant G (2002) Evaluation of the Synthetic Product. Synthetic Peptides, A User's Guide, Grant G A, Second Edition, 93-219; 220-291, Oxford University Press, New York) or genetic expression techniques, methods for which are readily known in the art to which the invention relates. Standard recombinant DNA and molecular cloning techniques are described for example in: Sambrook, and Maniatis, Molecular Cloning: A Laboratory Manual, Second Edition, Cold Spring Harbor Laboratory Press, Cold Spring Harbor, N.Y. (1989); Silhavy et al., Experiments with Gene Fusions, Cold Spring Harbor Laboratory Press, Cold Spring Harbor, N.Y. (1984); and, Ausubel et al., Current Protocols in Molecular Biology, published by Greene Publishing Assoc. and Wiley-Interscience (1987). Production of a peptide of the invention may also be achieved by an appropriate transgenic animal, microbe, or plant.

The targeting carrier peptide and the compound (including a therapeutic agent and including a peptide capable of interacting with an intracellular domain of Cx43) may be "connected" to each other by any means that allows the targeting carrier peptide to carry the compound (or therapeutic agent) across a cell membrane into a cell while retaining at least a level of the function and structure of the compound (or therapeutic agent). The word "connected" or like terms should be taken broadly to encompass any form of attachment, bonding, fusion or association between the targeting carrier peptide and the compound or therapeutic agent (for example, but not limited to, covalent bonding, ionic bonding, hydrogen bonding, aromatic stacking interactions, amide bonds, disulfide bonding, chelation) and should not be taken to imply a particular strength of connection. The targeting carrier peptide and the compound (or therapeutic agent) may be connected in an irreversible or a reversible manner, such that upon entry into a cell the compound is released from the targeting carrier peptide.

The compound (or therapeutic agent) may be connected to the targeting carrier peptide at its N-terminus, its C-terminus, or any other location. In one particular embodiment, the compound (or therapeutic agent) is connected to the targeting carrier peptide at its N-terminus. In another particular embodiment, the compound (or therapeutic agent) is connected to the targeting carrier peptide at its C-terminus. The compound (or therapeutic agent) may be connected to the targeting carrier peptide as described above. As described herein, the compound (or therapeutic agent) may be connected to the targeting carrier peptide directly or indirectly.

It should be appreciated that while the targeting carrier peptide and the compound (including a therapeutic agent and including a peptide capable of interacting with an intracellular domain of Cx43) may be connected directly to one another, constructs of use in the invention may also utilise linker molecules that connect the targeting carrier peptide and the compound (including a therapeutic agent and including a peptide capable of interacting with an intracellular domain of Cx43). Skilled persons will appreciate appropriate linker molecules of use in the invention. However, by way of example, the linker molecule may be a peptide, for example a flexible peptide linker, a rigid peptide linker, or a cleavable peptide linker. Examples of appropriate linker molecules are also provided in WO 91/09958, WO 03/064459, WO 00/29427, and WO 01/13957. Examples of linkers include glycine linkers and polyglutamine linkers. Examples of linker designing tools that may be of use include the Linker Database of the Centre for Integrative Bioinformatics VU at Vrije University of Amsterdam (www.ibi.vu.nl/programs/linkerdbwww/).

In one embodiment, the construct further comprises a linker to connect the targeting carrier peptide and the compound (or therapeutic agent).

In one embodiment, the compound (or therapeutic agent) is a peptide. In one embodiment, the compound (or therapeutic agent) is a peptide and the construct is a fusion peptide.

By way of example, where the compound (or therapeutic agent) is a peptide the construct may be produced using known recombinant expression or chemical synthesis techniques (as described herein); for example where the construct comprises a peptide capable of interacting with an intracellular domain of Cx43. The targeting carrier peptide and the peptide compound (or therapeutic agent) may also be manufactured separately and later connected to one another. For example, the targeting carrier peptide may be produced using known recombinant expression or chemical synthesis techniques (as described herein) and then later connected to a recombinantly expressed or chemically synthesised peptide compound (for example, a peptide capable of interacting with an intracellular domain of Cx43).

By way of example only, the methodology described in WO 91/09958, WO 03/064459, WO 00/29427, WO 01/13957 may be used to manufacture various constructs of the invention.

In accordance with the thirty-fourth, thirty-sixth, and/or thirty-eighth aspects of the invention, certain methods of the invention comprise connecting a compound or therapeutic agent to a targeting carrier peptide derived from the X-protein of the Hepatitis B virus. Targeting carrier peptides of use in these aspects of the invention as described elsewhere herein. In certain embodiments, as described herein, the compound or therapeutic agent is a peptide capable of interacting with an intracellular domain of Cx43. However, skilled persons will readily appreciate other compounds of use in these aspects of the invention. The compound/therapeutic agent and targeting carrier peptide can be manufactured and connected as described elsewhere herein.

In accordance with the thirty-fifth, thirty-seventh, and/or thirty-eighth aspects of the invention, certain methods of the invention comprise connecting a nucleic acid encoding a peptide compound or peptide therapeutic agent to a nucleic acid encoding a targeting carrier peptide derived from the X-protein of the Hepatitis B virus. Targeting carrier peptides of use in these aspects of the invention as described elsewhere herein. In certain embodiments, as described herein, the peptide compound or peptide therapeutic agent is a peptide capable of interacting with an intracellular domain of Cx43. However, skilled persons will readily appreciate other peptide compounds of use in these aspects of the invention. The nucleic acid encoding the peptide compound/ therapeutic agent and the nucleic acid encoding the targeting carrier peptide can be manufactured and connected as described elsewhere herein.

In certain embodiments of any aspect of the invention described herein, the construct comprises at least one further compound, for example for delivery to a hypoxic cell, that is, in addition to the first compound/therapeutic agent/ peptide capable of interacting with an intracellular domain of Cx43.

As previously mentioned, it will be apparent to those skilled in the art that reference to a "construct" herein includes a construct in accordance with the fortieth to forty-fifth aspects of the invention as well as a construct of use in the in the first to thirty-third aspects of the invention, unless the context clearly requires otherwise.

The at least one further compound may be any compound, for example a desired to be delivered to a hypoxic cell, including compounds which may provide a therapeutic or diagnostic benefit and compounds for use for research purposes. In certain embodiments, the compounds are chosen from: nucleic acids, peptide nucleic acids, peptides, polypeptides (including for example, fusion proteins), proteins, carbohydrates, peptidomimetics, small molecule inhibitors, chemical compounds, drugs, therapeutic compounds or agents, chemotherapeutic drugs, anti-inflammatory drugs, antibodies, single chain Fv fragments (SCFV), lipids, proteoglycans, glycolipids, lipoprotein, liposomes, glycomimetics, natural products, radioisotopes, dendrimers, micelles, nanoparticles, nanotubes, polymeric particles, imaging agents (for example, paramagnetic ions) and molecules, or fusion proteins. Where the compound is a nucleic acid it may be DNA, RNA, cDNA, double-stranded, single-stranded, sense, antisense, or circular, including DNAzymes, iRNA, siRNA, miRNA, piRNA, lcRNA, and ribozymes, phagemid, aptamer for example. Skilled persons may readily appreciate further examples of compounds in accordance with this embodiment of the invention.

The targeting carrier peptide and at least one further compound for delivery to a hypoxic cell may be "connected" to each other by any means that allows the targeting carrier peptide to carry the at least one further compound across a cell membrane into a cell while retaining at least a level of the function and structure of the compound. The word "connected" or like terms should be taken broadly to encompass any form of attachment, bonding, fusion or association between the targeting carrier peptide and the at least one compound (for example, but not limited to, covalent bonding, ionic bonding, hydrogen bonding, aromatic stacking interactions, amide bonds, disulfide bonding, chelation) and should not be taken to imply a particular strength of connection. The targeting carrier peptide and the at least one further compound may be connected in an irreversible or a reversible manner, such that upon entry into a cell the compound is released from the targeting carrier peptide.

The at least one further compound may be connected to the targeting carrier peptide at its N-terminus, its C-terminus, or at any other location. In one particular embodiment, the compound is connected to the targeting carrier peptide at its N-terminus. In another particular embodiment, the compound is connected to the targeting carrier peptide at its C-terminus. The compound may be connected to the targeting carrier peptide as described above.

It should be appreciated that while the at least one further compound may be connected directly to the targeting carrier peptide, constructs of the invention may also utilise linker molecules which connect the at least one further compound to the targeting carrier peptide. Skilled persons will appreciate appropriate linker molecules of use in the invention, for example as described above.

It should be appreciated that the at least one further compound may be connected to the targeting carrier peptide indirectly via another compound, for example but not necessarily via the compound/therapeutic agent (including for example a peptide capable of interacting with an intracellular domain of Cx43). In one particular embodiment the compound/therapeutic agent is a peptide and the at least one further compound may be connected at its N-terminus. In another particular embodiment the compound/therapeutic agent is a peptide and the at least one further compound may be connected at its C-terminus. The at least one further compound may be connected to the peptide compound as described above.

Persons skilled in the art will readily appreciate methodology for manufacturing constructs of use in the invention, having regard to the nature of the targeting carrier peptide and the compound (including a therapeutic agent and including a peptide capable of interacting with an intracellular domain of Cx43), and optionally further compound(s) to be included in the construct. Such methods include manufacturing the peptide and compound (or therapeutic agent(s)) or compounds separately and then connecting them, chemical synthesis of the construct, recombinant expression of the construct, and the like.

For example, peptides of use according to the invention or constructs of the invention may be produced by chemical peptide synthesis using known techniques such as liquid-phase and solid-phase synthesis, for example Fmoc or Boc solid-phase peptide synthesis. In particular, D-isomeric forms of peptides of use according to the invention can be produced by chemical peptide synthesis. In certain embodiments of the invention, D-isomeric forms of the targeting carrier peptide and/or a peptide compound (including a therapeutic agent and including a peptide capable of interacting with an intracellular domain of Cx43) may be preferred. For example, D-isomers may be preferred as they are more resistant to proteases. In other embodiments of the invention, L-isomeric forms of the targeting carrier peptide and/or a peptide compound (including a therapeutic agent and including a peptide capable of interacting with an intracellular domain of Cx43) may be preferred. For example, L-isomers may be preferred as they more closely mimic naturally occurring peptides. Persons skilled in the art will readily recognise appropriate use of D- and L-isomers.

By way of example, in embodiments of the invention where the compound, or therapeutic agent, or at least one further compound is a peptide, the constructs may be produced in the form of fusion peptides using known recombinant expression or chemical synthesis techniques as described herein. The targeting carrier peptide and the peptide compound(s) may also be manufactured separately and later connected to one another. Alternatively, parts of the construct may be produced in the form of separate fusion peptides using known recombinant expression or chemical synthesis techniques (as described herein) and later connected to one another. By way of example, a fusion peptide comprising a targeting carrier peptide and a peptide compound, for example a peptide capable of interacting with an intracellular domain of Cx43, may be produced, and then later connected to a further peptide compound for delivery to a hypoxic cell. By way of further example, a fusion peptide comprising two or more peptide compounds may be produced, and then later connected to a targeting carrier peptide.

By way of further example, where the compound, or therapeutic agent, or at least one further compound, is a nucleic acid, the targeting carrier peptide and the nucleic acid compound may be made separately (using chemical synthesis or recombinant techniques, for example) and then connected via one of a number of known techniques. For example, in certain embodiments a fusion peptide comprising a targeting carrier peptide and a peptide capable of interacting with an intracellular domain of Cx43 may be produced, and then connected to the nucleic acid compound for delivery to a cell.

By way of further example, in embodiments of the invention where the compound is a carbohydrate, the targeting carrier peptide and the carbohydrate compound may be made separately and then connected via one of a number of known techniques. For example, in certain embodiments a fusion peptide comprising a targeting carrier peptide and a peptide capable of interacting with an intracellular domain of Cx43 may be produced, and then connected to the carbohydrate compound for delivery to a cell.

By way of further example, in embodiments of the invention where the compound is a lipid, the targeting carrier peptide and the lipid compound for delivery to a cell may be made separately and then connected via one of a number of known techniques. For example, in certain embodiments, a fusion peptide comprising a targeting carrier peptide and a peptide capable of interacting with an intracellular domain of Cx43 may be produced, and then connected to the lipid compound for delivery to a cell.

By way of example only, the methodology described in WO 91/09958, WO 03/064459, WO 00/29427, WO 01/13957 may be used to manufacture various constructs of the invention.

While it is not necessary for the performance of the invention, in one embodiment, a construct in accordance with the fortieth to forty-fifth aspects of the invention or of use in the first to thirty-third aspects of the invention may further comprise at least one additional heterologous molecule. By way of example only, the heterologous molecule may be a molecule which may assist the activity of the construct (for example, the activity of the targeting carrier peptide, a compound, or a combination thereof), aid in release of the peptide from endosomes (for example, fusogenic lipids and membrane-disruptive peptides or polymers), enable targeting to a particular intracellular compartment or organelle, protect the construct from degradation or otherwise increase the half-life of the construct, aid in isolation and purification of the construct during manufacture, or aid in the binding of a cargo.

In one embodiment, the additional heterologous molecule may be a his-tag, a c-myc tag, a GST tag, or biotin, which may aid in isolation of a construct expressed recombinantly.

In another embodiment, the additional heterologous molecule may be a molecule that may assist in targeting the construct to a specific cell type. When used herein "targeting the construct to a specific cell type", "specifically target a desired cell" and like phrases should not be taken to require 100% specificity, although this may be preferred. When used herein "targeting the construct to a specific molecular target", "specifically target a desired molecule" and like phrases should not be taken to require 100% specificity, although this may be preferred. For example, in certain embodiments relating to diseases or disorders of the eye the additional heterologous molecule may assist in targeting to an endothelial cell or a retinal pigment epithelial cell. Those skilled in the art will readily be able to identify appropriate heterologous molecules that may assist in targeting the construct to a specific cell type.

Those skilled in the art will readily be able to identify cell types of interest for targeting having regard, for example, to the disease or disorder being treated. However, by way of example, constructs of use in certain aspects and embodiments of the invention could be targeted to blood vessel endothelial cells, tumour cells, neuronal cells, astrocytes, inflammatory cells, retinal pigment epithelial cells, or cardiomyocytes. For example, it may be desirable to target astrocytes to maintain a functional astrocytic syncytium for neuronal protection. Those skilled in the art will readily be able to identify appropriate heterologous molecules that may assist in targeting the construct to a specific cell type.

In another embodiment, the molecule is a nucleic-acid binding peptide which may assist in the delivery of RNA/DNA/nucleic acids to a cell.

It should be appreciated that a combination of two or more different heterologous molecules may be used in a construct of the invention.

The heterologous molecules may be connected to the targeting carrier peptide or compound, or synthesised as a part of the construct, using any appropriate means (as described above), having regard to the chemical nature of the heterologous molecule. In one embodiment, the heterologous molecules are peptide-based. However, those of skill in the art to which the invention relates will readily recognise molecules of an alternative nature that may be connected to or incorporated in the constructs of the invention. Examples of alternative molecules are provided, for example, in WO 91/09958, WO 03/064459, WO 00/29427, and WO 01/13957.

As described above, in accordance with the tenth to fifteenth aspects the invention also provides methods of treatment comprising administration of compositions comprising (a) constructs of the invention, (b) nucleic acids encoding constructs of the invention, and (c) nucleic acid vectors comprising nucleic acids encoding constructs of the invention in association with one or more diluents, carriers and/or excipients and/or additional ingredients. Persons skilled in the art will appreciate carriers, excipients, diluents and/or additional therapeutic agents of use in the invention with reference to the description provided herein.

As described above, in accordance with the forty-first, forty-third, and forty-fifth aspects, the invention also provides compositions comprising (a) constructs of the invention, (b) nucleic acids encoding constructs of the invention, and/or (c) nucleic acid vectors comprising nucleic acids encoding constructs of the invention in association with one or more diluents, carriers and/or excipients and/or additional ingredients. Persons skilled in the art will appreciate carriers, excipients, diluents and/or additional therapeutic agents of use in the invention with reference to the description provided herein.

To this extent, it should be appreciated that reference herein to administration of a construct, a nucleic acid, and/or a nucleic acid vector of the invention is to include reference to delivery or administration of a composition comprising a construct, a nucleic acid, and/or a nucleic acid vector of the invention. For example, in the first to third broad aspects of the invention administration of a construct, a nucleic acid, and/or a nucleic acid vector is to be taken to include administration of a composition comprising a construct, a nucleic acid, and/or a nucleic acid vector.

In one embodiment of the tenth to fifteenth, forty-first, forty-third, and forty-fifth aspects of the invention, the one or more diluents, carriers and/or excipients are suitable for use in vitro. In another embodiment, the one or more diluents, carriers and/or excipients are suitable for use in vivo (in this instance they may be referred to as "pharmaceutically acceptable"). It will be appreciated that compositions as described in the tenth to fifteenth, forty-first, forty-third, and forty-fifth aspects of the invention will be suitable for use in manufacturing medicaments in accordance with the sixteenth to twenty-first aspects of the invention. It will also be appreciated that compositions as described in the tenth to fifteenth, forty-first, forty-third, and forty-fifth aspects of the invention will be suitable for use in treatment in accordance with the twenty-second to twenty-seventh aspects of the invention. It will further be appreciated that constructs, nucleic acids, and nucleic acid vectors described in the fortieth, forty-second, and forty-fourth aspects of the invention and compositions described in the tenth to fifteenth, forty-first, forty-third, and forty-fifth aspects of the invention will be suitable for use in methods of targeting delivery of a peptide compound to hypoxic cells in accordance with the first to third and twenty-eighth to thirty-third aspects of the invention.

"Pharmaceutically acceptable diluents, carriers and/or excipients" is intended to include substances that are useful in preparing a pharmaceutical composition, may be co-administered with a construct or nucleic acid encoding a construct of the invention while allowing it to perform its intended function, and are generally safe, non-toxic and neither biologically nor otherwise undesirable. Pharmaceutically acceptable diluents, carriers and/or excipients include those suitable for veterinary use as well as human pharmaceutical use. Examples of pharmaceutically acceptable diluents, carriers and/or excipients include solutions, solvents, dispersion media, delay agents, emulsions, and the like.

In addition to standard diluents, carriers and/or excipients, a composition for use in accordance with the invention may be formulated with one or more additional constituents, or in such a manner, so as to enhance the activity of a construct, nucleic acid encoding a construct, and/or compound for delivery to a cell, help protect the integrity or increase the half-life or shelf life of such agents, or provide other desirable benefits, for example. By way of example, the composition may further comprise constituents which provide protection against proteolytic degradation, enhance bioavailability, decrease antigenicity, or enable slow release upon administration to a subject. For example, slow release vehicles include macromers, poly(ethylene glycol), hyaluronic acid, poly(vinylpyrrolidone), or a hydrogel. By way of further example, the compositions may also include preserving agents, solubilising agents, stabilising agents, wetting agents, emulsifying agents, sweetening agents, colouring agents, flavouring agents, coating agents, buffers and the like. Those of skill in the art to which the invention relates will readily identify further additives which may be desirable for a particular purpose.

Furthermore, while not necessary for the performance of the invention, cell permeability of the constructs, nucleic acids encoding the constructs and/or compounds may be increased, or facilitated, through formulation of the composition. For example, the constructs, nucleic acids encoding the constructs, and/or compounds of the invention may be formulated into liposomes. Further examples are provided in WO 91/09958, WO 03/064459, WO 00/29427, and WO 01/13957.

Additionally, a pharmaceutical composition in accordance with the invention may be formulated with additional active ingredients which may be of benefit to in particular instances for particular diseases and disorders. Persons of ordinary skill in the art to which the invention relates will readily appreciate suitable additional active ingredients having regard to the description of the invention herein and the purposes for which the compound and/or construct is required, including, for example, the nature and progression of any disease to be treated.

As a general example, agents used to treat age-related macular degeneration and/or diabetic retinopathy such as an antisense oligonucleotide to reduce production of proteins in the inflammatory or complement pathway such as Ang2, Tie2, integrin or Cx43, or an antisense oligonucleotide interfering with production of any VEGF or PDGF or their receptors may be used. A further example is the use of an anti-VEGF and/or anti-PDGF antisense oligonucleotide to reduce neovascularisation in age related macular degeneration, diabetic retinopathy or a cancer.

Compositions of the invention may be formulated into any customary form such as solutions, orally administrable liquids, injectable liquids, injectable solutions, tablets, coated tablets, capsules, pills, granules, suppositories, transdermal patches, suspensions, emulsions, sustained release formulations, gels, aerosols, powders, injectable colloidal systems (such as nanoparticles, liposomes, and microemulsions), hydrogels, and solid implants (including biodegradable implants, such as those based on poly(lactic-co-glycolic acid) (PLGA)), for example. Additionally, sustained release formulations may be utilised. The form chosen will reflect the purpose for which the composition is intended and the mode of delivery or administration to a sample (e.g. a population of cells) or a subject.

For example, compositions of the invention may be formulated into customary forms for ocular delivery, for example injectable liquids, injectable solutions, injectable colloidal systems (such as nanoparticles, liposomes, and microemulsions), injectable hydrogels, and solid implants.

Skilled persons will readily recognise appropriate formulation methods. However, by way of example, certain methods of formulating compositions may be found in Gennaro A R: Remington: The Science and Practice of Pharmacy, 20th ed., Lippincott, Williams & Wilkins, 2000.

It will be appreciated by those of general skill in the art to which the invention relates, having regard to the nature of the invention and the results reported herein, that the present invention is applicable to a variety of different animals. Accordingly, a "subject" includes any animal of interest. However, in one particular embodiment the "subject" is a mammal, more particularly human.

In the fourth, sixth, eighth, tenth, twelfth, fourteenth, sixteenth, eighteenth, twentieth, twenty-second, twenty-fourth, and/or twenty-sixth aspects the invention relates to methods of treating a diseases or disorder associated with hypoxia, the manufacture of medicaments for treating a disease or disorder associated with hypoxia, and uses of constructs for the treatment of a disease or disorder associated with hypoxia.

As used herein, the phrase "disease or disorder associated with hypoxia" and the like should be interpreted broadly to include primary diseases or disorders as well as diseases or disorders that are secondary to physical injury. The phrase should be interpreted to include diseases and disorders of structure and/or function. It should be taken into include syndromes. The phrase should be interpreted broadly to include an association, linkage, or correlation with generalised, local, or cellular hypoxia and includes acute and chronic hypoxia. As will be understood by skilled persons, hypoxia refers to a tissue that has been exposed to a concentration of oxygen that is significantly lower than the normal physiological concentration of oxygen in healthy well-perfused tissue. It should be interpreted broadly to include circumstances where there is a reduction in oxygen delivery as well as circumstances where there is a complete lack of oxygen delivery. Preferably, the hypoxic tissue or hypoxic cell(s) within the tissue exhibits upregulation of syndecan-4 as a result of the hypoxia. Hypoxia which triggers syndecan-4 upregulation may be transient, and does not need to be a sustained or particular level of hypoxia.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder is associated with ischemia. In another embodiment, the disease or disorder is associated with haemorrhage. In another embodiment, the disease or disorder is associated with neovascularisation. In one embodiment, the disease or disorder is associated with hypoperfusion.

In another embodiment of the fourth, sixth, eighth, tenth, twelfth, fourteenth, sixteenth, eighteenth, twentieth, twenty-second, twenty-fourth, and/or twenty-sixth aspects of the invention, the disease or disorder involves inflammation. In a particular embodiment, the disease or disorder involves chronic inflammation.

It will be appreciated that the disease or disorder may be associated with two or more of the foregoing.

As used herein, the phrase "associated with ischemia" or "associated with ischemic hypoxia" should be interpreted broadly to include an association, linkage, or correlation with hypoxia associated with insufficient blood flow to a tissue or organ. For example, as will be understood by those skilled in the art, ischemic hypoxia may be the result of embolism, aneurysm, heart attack, trauma, or insufficient blood flow secondary to a pathophysiological process, including insufficient capillary blood flow. It should be taken to include acute and chronic ischemia. It should be taken to include partial and total ischemia.

As used herein, the term "associated with haemorrhage" should be interpreted broadly to include arterial, venous and capillary haemorrhage. It should be taken to include primary and secondary haemorrhage, and external and internal haemorrhage.

As used herein, the phrase "associated with neovascularisation" should be interpreted broadly to include an association, linkage, or correlation with the formation of new blood vessels, including microvascular networks, capable of perfusion by red blood cells. It should be taken to include both normal and abnormal neovascularisation.

As used herein, the phrase "disease or disorder involving inflammation", and the like, should be taken to include diseases or disorders involving inflammatory processes associated with acute inflammation and/or chronic inflammation. It should be taken to include a range of severities of inflammatory response.

As used herein, the phrase "associated with hypoperfusion" should be interpreted broadly to include an association, linkage, or correlation with local or systemic hypoperfusion. It should be taken to include both acute and chronic hypoperfusion. It should not be taken to indicate a particular degree of hypoperfusion.

It will be appreciated that the disease or disorder associated with hypoxia may affect any organ or organ system of the body. For example, the disease or disorder may affect the integumentary system, the musculoskeletal system, the nervous system (including the central nervous system, peripheral nervous system, and sensory nervous system, for example), the cardiovascular system, the lymphatic system, the respiratory system, the endocrine system, the urinary system, the digestive system, or the reproductive system.

Persons of ordinary skill in the art will readily be able to identify diseases or disorders associated with hypoxia, including those associated with ischemic hypoxia, haemorrhage, and/or neovascularisation, and those involving inflammation.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is cancer. In one embodiment, the cancer is brain glioma, for example astrocytomas, ependymomas, and oligodendrogliomas. In another embodiment, the cancer is epidermal carcinoma. In another embodiment, the cancer is ovarian carcinoma.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is stroke. In one embodiment, the disease or disorder is transient ischemic attacks. In one embodiment, the disease or disorder associated with hypoxia is Alzheimer's disease. In one embodiment, the disease or disorder is Parkinson's disease. In one embodiment, the disease or disorder associated with hypoxia is multiple sclerosis. In one embodiment, the disease or disorder associated with hypoxia is vascular dementia.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is cardiac ischemia. In one embodiment, the disease or disorder associated with hypoxia is ischemic colitis. In one embodiment, the disease or disorder associated with hypoxia is acute limb ischemia. In one embodiment, the disease or disorder associated with hypoxia is cutaneous ischemia.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is sepsis. For example, sepsis secondary to bacterial, fungal, and/or viral infection of any organ system. By way of non-limiting example the infection could be pneumonia, appendicitis, peritonitis, urinary tract infection, cholecystitis, cholangitis, cellulitis, meningitis, or encephalitis. By way of further non-limiting example the sepsis could be secondary to acute pancreatitis, colitis, autoimmune diseases, coeliac disease, glomerulonephritis, hepatitis, inflammatory bowel disease, pre-perfusion injury, and transplant rejection In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is a disease or disorder of the eye. The phrase "disease or disorder of the eye" should be interpreted broadly as described elsewhere herein. In one embodiment, the disease or disorder is of the posterior cavity of the eye. In one embodiment, the disease or disorder is of the anterior cavity of the eye.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is AMD (including wet and/or dry AMD). In one embodiment, the disease or disorder associated with hypoxia is diabetic retinopathy. In one embodiment, the disease or disorder associated with hypoxia is retinal vein and/or branch occlusion, retinal artery occlusion, or retinal stroke. In one embodiment, the disease or disorder associated with hypoxia is macular oedema. In one embodiment, the disease or disorder associated with hypoxia is uveitis. In one embodiment, the disease or disorder associated with hypoxia is blepharitis. In one embodiment, the disease or disorder associated with hypoxia is severe dry eye syndrome. In one embodiment, the disease or disorder associated with hypoxia is optic neuritis.

In one embodiment of the fourth, sixth, eighth, tenth, twelfth, fourteenth, sixteenth, eighteenth, twentieth, twenty-second, twenty-fourth, and/or twenty-sixth aspects of the invention, the disease or disorder associated with hypoxia is associated with upregulation of one or more heparan sulfate proteoglycan (HSPG), for example a syndecan or a glypican. In one particular embodiment, the disease or disorder associated with hypoxia is associated with upregulation of syndecan-1, syndecan-2, syndecan-3, syndecan-4 or glypican-4. In one particular embodiment, the disease or disorder associated with hypoxia is associated with upregulation of syndecan-4.

Persons of ordinary skill in the art will readily be able to identify diseases or disorders associated with hypoxia that are also associated with upregulation of one or more heparin sulphate proteoglycan.

In the fifth, seventh, ninth, eleventh, thirteenth, fifteenth, seventeenth, nineteenth, twenty-first, twenty-third, twenty-fifth, and twenty-seventh aspects the invention relates to methods of treating a disease or disorder of the eye, the manufacture of medicaments for treating a disease or disorder of the eye, and uses of constructs for the treatment of a disease or disorder of the eye.

As used herein, the phrase "disease or disorder of the eye" and the like should be interpreted broadly to include diseases or disorders that are directly or primarily of the eye, including those that are secondary to physical injury, as well as diseases or disorders secondary to a disease that directly or primarily affect another organ or organ system. The phrase should be interpreted to include diseases and disorders of structure and/or function. It should be taken into include syndromes.

In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder is of the posterior cavity of the eye. In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder is of the anterior cavity of the eye.

As used herein, "the posterior cavity of the eye" (and the like) refers to the part of the eye posterior to the lens, including the anterior hyaloid membrane, vitreous humor, retina, choroid, and optic nerve.

As used herein, "the anterior cavity of the eye" (and the like) refers to the part of the eye anterior to the lens, including the lens, iris, conjunctiva, trabecular network, ocular tear glands, eyelid, and cornea.

In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder of the eye is associated with hypoxia. In one embodiment, the disease or disorder of the eye is associated with ischemic hypoxia. In another embodiment, the disease or disorder of the eye is associated with haemorrhage. In another embodiment, the disease or disorder of the eye is associated with neovascularisation. The terms "associated with hypoxia" and the like should be taken as described elsewhere herein.

In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder of the eye is one that involves inflammation. In a particular embodiment, the disease or disorder is one that involves chronic inflammation. In another particular embodiment, the disease or disorder is one that involves acute inflammation. For example, acute inflammation may occur in acute retinal vein or branch vein occlusion. The terms "inflammation" and the like should be taken as described elsewhere herein.

It will be appreciated that the disease or disorder of the eye may be associated with two or more of the foregoing.

Persons of ordinary skill in the art will readily be able to identify diseases or disorders of the eye associated with hypoxia, hypoperfusion, ischemic hypoxia, haemorrhage, and/or neovascularisation. By way of example only, diseases or disorders of the eye associated with hypoxia include AMD, diabetic retinopathy, glaucoma, retinal vein and/or branch vein occlusion, retinal artery occlusion or retinal stroke, and diabetic macular oedema. By way of example only, diseases or disorders of the eye associated with hypoperfusion include AMD, diabetic retinopathy, glaucoma, retinal vein and/or branch vein occlusion, retinal artery occlusion or retinal stroke, and diabetic macular oedema, uveitis, blepharitis, severe dry eye syndrome, diabetic peripheral neuropathy, and optic neuritis. By way of example only, diseases or disorders of the eye associated with ischemic hypoxia include AMD, diabetic retinopathy, glaucoma, retinal vein and/or branch vein occlusion, retinal artery occlusion or retinal stroke, and diabetic macular oedema. By way of example only, disease or disorders of the eye associated with haemorrhage include AMD, diabetic retinopathy, retinal vein and/or branch vein occlusion, retinal artery occlusion or retinal stroke, diabetic macular oedema, uveitis, blepharitis, severe dry eye syndrome, diabetic peripheral neuropathy, and optic neuritis. By way of example only, diseases or disorders of the eye associated with neovascularisation include AMD, diabetic retinopathy, retinal vein and/or branch vein occlusion, and diabetic macular oedema. By way of example only, disease or disorders of the eye involving inflammation include AMD, diabetic retinopathy, retinal vein and/or branch vein occlusion, diabetic macular oedema, blepharitis, severe dry eye syndrome, diabetic peripheral neuropathy, and optic neuritis.

In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder of the eye is associated with connexin43 hemichannel dysfunction. In one embodiment, the disease or disorder of the eye is associated with uncontrolled pathological connexin43 hemichannel opening.

Persons of ordinary skill in the art will readily be able to identify diseases or disorders of the eye associated with connexin43 hemichannel dysfunction. By way of example only, disease associated with connexin43 hemichannel dysfunction include AMD, diabetic retinopathy, glaucoma, retinal vein and/or branch vein occlusion, retinal artery occlusion or retinal stroke, diabetic macular oedema, uveitis, blepharitis, severe dry eye syndrome, diabetic peripheral neuropathy, and optic neuritis.

In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder of the eye is associated with upregulation of one or more heparan sulfate proteoglycan (HSPG), for example a syndecan or a glypican. In one particular embodiment, the disease or disorder of the eye is associated with upregulation of syndecan-1, syndecan-2, syndecan-3, syndecan-4 or glypican-4. In one particular embodiment, the disease or disorder of the eye is associated with upregulation of syndecan-4.

Persons of ordinary skill in the art will readily be able to identify diseases or disorders of the eye associated with upregulation of one or more heparin sulphate proteoglycan. By way of example only, diseases or disorders of the eye associated with upregulation of one or more heparin sulphate proteoglycan include AMD, diabetic retinopathy, glaucoma, retinal vein and/or branch vein occlusion, retinal artery occlusion or retinal stroke, diabetic macular oedema, uveitis, blepharitis, severe dry eye syndrome, and optic neuritis.

In one embodiment of the fifth, seventh, ninth, eleventh, thirteenth, fifteenth, seventeenth, nineteenth, twenty-first, twenty-third, twenty-fifth, and twenty-seventh aspects of the invention, the disease or disorder of the eye is age related macular degeneration (AMD), including wet and/or dry AMD. In one embodiment, the disease or disorder of the eye is diabetic retinopathy. In one embodiment, the disease or disorder of the eye is retinal vein and/or branch vein occlusion. In one embodiment, the disease or disorder of the eye is retinal artery occlusion. In one embodiment, the disease or disorder of the eye is retinal stroke. In one embodiment, the disease or disorder of the eye is diabetic macular oedema.

In one embodiment, the disease or disorder is uveitis. In one embodiment, the disease or disorder of the eye is blepharitis. In one embodiment, the disease or disorder of the eye is severe dry eye syndrome. In one embodiment, the disease or disorder of the eye is optic neuritis. In one embodiments, the disease or disorder of the eye is diabetic peripheral neuropathy.

In one embodiment of the first to fifteenth aspects of the invention, the construct, nucleic acid, or nucleic acid vector, or composition comprising the construct, nucleic acid, or nucleic acid vector, is administered systemically. In one embodiment, administration is enteral, for example oral or by suppository. In one embodiment, administration is parenteral, for example by intravenous injection, subcutaneous injection, or intramuscular injection.

In one embodiment of the first to fifteenth aspects of the invention, the construct, nucleic acid, or nucleic acid vector, or composition comprising the construct, nucleic acid, or nucleic acid vector is administered topically. For example, administration may be by way of cream, ointment, gel, eye drops, ear drops, or inhalation. For example, administration may be by way of a topical device such as a transdermal device, soft contact lens, or external ocular insert.

In one embodiment of the first to fifteenth aspects of the invention, the construct or composition comprising the construct may be administered locally. For example, administration may be by way of periocular injection (for example subconjunctival injection or subtenon injection) or intraocular injection (for example intracameral injection, intravitreal injection or suprachoroidal injection). In one embodiment, administration may be by way of a local implant or device such as, for example, an intraocular insert or implant or a vaginal ring device. Examples of intraocular implants include a biodegradable polymer such as PLGA (as is used for Ozurdex®), self-assembling polymeric particles, a cell-based implant producing the drug construct, or a pellet encased in a semipermeable membrane (as is used for Retisert® or Vitrosert®).

For example, administration may be by way of chemical penetration enhancers such as surfactants (as described in Som, I., Bhatia, K., Yasir, M., 2012. Status of surfactants as penetration enhancers in transdermal drug delivery. J. Pharm. Bioallied Sci. 4, 2-9), terpenes (for example as described in Aqil, M., Ahad, A., Sultana, Y., Ali, A., 2007. Status of terpenes as skin penetration enhancers. Drug Discov. Today 12, 1061-1067), or physical methods such as microneedles, thermal ablation, microdermabrasion, electroporation and cavitational ultrasound (for example as described in Mark R. Prausnitz and Robert Langer. Transdermal drug delivery Nat Biotechnol. 2008 26(11): 1261-1268. and Escobar-Chavez, J. J., Bonilla-Martinez, D., Villegas-Gonzalez, M. A., Revilla-Vazquez, A. L., 2009. Electroporation as an efficient physical enhancer for skin drug delivery. J. Clin. Pharmacol. 49, 1262-1283) and iontophoresis including pulse depolarization (PDP) iontophoresis (for example as described in Aramaki, Y., Arima, H., Takahashi, M., Miyazaki, E., Sakamoto, T., Tsuchiya, S., 2003. Intradermal delivery of antisense oligonucleotides by the pulse depolarization iontophoretic system. Biol. Pharm. Bull. 26, 1461-1466 and Sakamoto, T., Miyazaki, E., Aramaki, Y., Arima, H., Takahashi, M., Kato, Y., Koga, M., Tsuchiya, S., 2004. Improvement of dermatitis by iontophoretically delivered antisense oligonucleotides for interleukin-10 in NC/Nga mice. Gene Ther. 11, 317-324).

In one embodiment of the fifth, seventh, ninth, eleventh, thirteenth, and/or fifteenth aspects of the invention, the construct, nucleic acid, or nucleic acid vector, or composition comprising the construct, nucleic acid, or nucleic acid vector, is administered by periocular injection. For example, administration may be by subconjunctival injection or subtenon injection.

In one embodiment of the fifth, seventh, ninth, eleventh, thirteenth, and/or fifteenth aspects of the invention, the construct, nucleic acid, or nucleic acid vector, or composition comprising the construct, nucleic acid, or nucleic acid vector, is administered by intraocular injection. For example, administration may be by intracameral injection, intravitreal injection or suprachoroidal injection. In one embodiment, the administration is by way of an intraocular insert or implant. A range of intraocular inserts or implants may be suitable. For example, an intraocular implant could include a biodegradable polymer such as PLGA (as is used for Ozurdex®), self-assembling polymeric particles, a cell-based implant producing the drug construct, or a pellet encased in a semipermeable membrane (as is used for Retisert® or Vitrosert®).

Skilled persons may identify other appropriate administration modes for methods of the invention.

In one embodiment of the sixteenth to twenty-first aspects of the invention, the medicament is formulated for systemic administration. In one embodiment, the medicament is formulated for enteral administration, for example oral or by suppository. In one embodiment, the medicament is formulated for parenteral administration, for example by intravenous injection, subcutaneous injection, or intramuscular injection.

In one embodiment of the sixteenth to twenty-first aspects of the invention, the medicament is formulated for topical administration. For example, the medicament may be formulated for administration by way of cream, ointment, gel, eye drops, ear drops, or inhalation. For example, the medicament may be formulated for administration by way of a topical device such as a transdermal device, a soft contact lens or external ocular insert.

In one embodiment of the sixteenth to twenty-first aspects of the invention, the construct or composition comprising the construct is formulated for local administration. For example, the medicament may be formulated for administration may by way of periocular injection (for example subconjunctival injection or subtenon injection) or intraocular injection (for example intracameral injection, intravitreal injection or suprachoroidal injection). In one embodiment, the medicament may be formulated for administration may by way of a local implant or device such as, for example, an intraocular implant or a vaginal ring device.

In one embodiment of the seventeenth, nineteenth, and/or twenty-first aspects of the invention, the medicament is formulated for administration by periocular injection. For example, the medicament may be formulated for administration by subconjunctival injection or subtenon injection.

In one embodiment of the seventeenth, nineteenth, and/or twenty-first aspects of the invention, the medicament is formulated for administration by intraocular injection. For example, the medicament may be formulated for administration by intracameral injection, intravitreal injection or suprachoroidal injection. In one embodiment, the medicament is formulated for administration by way of an intraocular insert or implant.

In one embodiment of the twenty-second to twenty-seventh aspects of the invention, the use is by systemic administration. In one embodiment, the use is by enteral administration, for example oral or by suppository. In one embodiment, the use is by parenteral administration, for example by intravenous injection, subcutaneous injection, or intramuscular injection.

In one embodiment of the twenty-second to twenty-seventh aspects of the invention, the use is by topical administration. For example, the use may be by administration of cream, ointment, gel, eye drops, ear drops, or an inhalable formulation. For example, the use may be by way of administration via a topical device such as a transdermal device, soft contact lens, or external ocular insert.

In one embodiment of the twenty-second to twenty-seventh aspects of the invention, the use is by local administration. For example, the use may be by administration of a periocular injection (for example subconjunctival or subtenon injection) or intraocular injection (for example intracameral injection, intravitreal injection, or suprachoroidal injection). In one embodiment, the use may be by administration via a local implant or device such as, for example, an intraocular implant or a vaginal ring device In one embodiment of the twenty-third, twenty-fifth, and/or twenty-seventh aspects of the invention, the use in treating a disease or disorder of the eye is by periocular injection. For example, the use may be by subconjunctival or subtenon injection.

In one embodiment of the twenty-third, twenty-fifth, and/or twenty-seventh aspects of the invention, the use in treating a disease or disorder of the eye may be by intraocular injection. For example, the use may be by intracameral injection, intravitreal injection or suprachoroidal injection. In one embodiment, the use may be by administration by way of an intraocular insert or implant.

Where reference is made to a medicament comprising a construct, nucleic acid, or nucleic acid vector it will be appreciated that the medicament may comprise a composition comprising a construct, nucleic acid, or nucleic acid vector.

As will be appreciated, the dose administered, period of administration, and general administration regime in accordance with the fourth to fifteenth aspects of the invention may differ between subjects depending on such variables as the compound or therapeutic agent comprising the construct, particular disease or disorder being treated, the severity of any symptoms of a subject to be treated, the mode of administration chosen, and the age, sex and/or general health of a subject.

It should be appreciated that administration may occur daily, and may include a single daily dose, administration of a number of discrete divided doses, or continuous administration as may be appropriate. For example, continuous administration may be achieved using an external or internal device or implant, such as, for example, an external ocular device or an intraocular device It should be appreciated that administration may occur less frequently than daily, for example administration may be by way of an initial dose, with redosing administered weekly, fortnightly, monthly, bimonthly and so on, depending on the formulation and mode of administration. Furthermore, it should be appreciated that the dosing regimen may involve an initial period of relatively frequent loading doses followed by less frequent maintenance doses. For example, in the case of intravitreal injection a number of loading doses may be administered approximately monthly, followed by approximately bimonthly maintenance doses. By way of example only, administration may comprise 2, 3, 4, 5 or 6 loading doses.

By way of example, unit doses may be administered once or more than once per day, for example 1, 2, 3, 4, 5 or 6 times a day to achieve a desired total daily dose. By way of example, a unit dose of a construct of the invention may be administered in a single daily dose or a number of discrete doses or continuously.

In embodiments of the fourth to fifteenth aspects of the invention where the compound is a peptide capable of interacting with an intracellular domain of Cx43, systemic unit doses may be administered once or more than once per day, for example 1, 2, 3, 4, 5 or 6 times a day to achieve a desired total daily dose. By way of example, a unit dose of a construct of the invention may be administered in a single daily dose or a number of discrete doses, or continuously to achieve a daily dose of approximately 70 mg to approximately 1,750 mg of the peptide capable of interacting with an intracellular domain of Cx43.

By way of example, a systemic unit dose of a construct of the invention may be administered once or more than once a day (for example 1, 2, 3, 4, 5 or 6, typically 1 to 4 times a day), such that the total daily dose is in the range (for a 70 kg adult) of approximately 70 mg to approximately 1,750 mg, that is in the range of approximately 1 to approximately 25 mg/kg/day of the peptide capable of interacting with an intracellular domain of Cx43.

By way of further example, a construct of the invention may be administered systemically once or more than once a day to achieve a dose of the peptide capable of interacting with an intracellular domain of Cx43 of approximately 1 mg to approximately 2 mg/kg of body weight per day or approximately 5 mg to approximately 25 mg/kg of body weight per day.

In embodiments of the fourth to fifteenth aspects of the invention where the compound is a peptide capable of interacting with an intracellular domain of Cx43, a construct of the invention may be administered systemically to achieve a circulating concentration of the peptide capable of interacting with an intracellular domain of Cx43 in the range of approximately 5 micromolar to approximately 20 micromolar. In another example, a construct of the invention may be administered to achieve a circulating concentration of approximately 5 micromolar. In another example, a construct of the invention may be administered systemically to achieve a circulating concentration of approximately 10 micromolar. In another example, a construct of the invention may be administered systemically to achieve a circulating concentration of approximately 15 micromolar. In another example, a construct of the invention may be administered systemically to achieve a circulating concentration of approximately 20 micromolar.

In embodiments of the fourth to fifteenth aspects of the invention where the compound is a peptide capable of interacting with an intracellular domain of Cx43, a construct of the invention may be administered by systemic infusion at a concentration sufficient to maintain a circulating concentration of the peptide capable of interacting with an intracellular domain of Cx43 of approximately 2.5 micromolar to approximately 250 micromolar for a desired period. In another example, a construct of the invention may be administered by systemic infusion at a concentration sufficient to maintain a circulating concentration of the peptide capable of interacting with an intracellular domain of Cx43 of approximately 2.5 micromolar to approximately 100 micromolar. In another example, a construct of the invention may be administered by systemic infusion at a concentration sufficient to maintain a circulating concentration of approximately 10 micromolar to approximately 100 micromolar for a desired period. In another example, a construct of the invention may be administered by systemic infusion at a concentration sufficient to maintain a circulating concentration of approximately 100 micromolar to approximately 250 micromolar for a desired period.

In embodiments of the fourth to fifteenth aspects of the invention where the compound is a peptide capable of interacting with an intracellular domain of Cx43, a construct of the invention may be administered topically to achieve a tissue concentration of the peptide capable of interacting with an intracellular domain of Cx43 in the range of approximately 1 micromolar to approximately 100 micromolar. In another example, a construct of the invention may be administered intravitreally to achieve a tissue concentration of 1, 2, 3, 4 or 5 micromolar. In another example, a construct of the invention may be administered intravitreally to achieve a tissue concentration of approximately 10, 15 or 20 micromolar. In another example, a construct of the invention may be administered intravitreally to achieve a tissue concentration of approximately 30, 40, 50, 60, 70, 80, 90, or 100 micromolar. In another example, a construct of the invention may be administered intravitreally to achieve a tissue concentration in the range of approximately 1 to approximately 20 micromolar. In another example, a construct of the invention may be administered intravitreally to achieve a tissue concentration in the range of approximately 1 to approximately 5 micromolar, or in the range of approximately 5 to approximately 10 micromolar, or in the range of approximately 10 to approximately 20 micromolar.

It should be appreciated that topical administration may be suitable, for example, for the treatment of diseases or disorders of the anterior cavity of the eye, such as, for example, severe dry eye or blepharitis. It should also be appreciated that topical administration may be suitable, for example, for the treatment of diseases or disorders of the skin or mucosa (e.g. oral mucosa, nasal mucosa, vaginal mucosa), for example cancer.

Persons skilled in the art will readily be able to determine appropriate dosages based on the variables mentioned above, in particular having regard to the compound or therapeutic agent comprising the construct.

Data obtained from cell culture assays and animal studies can be used in formulating a range of dosages for use in humans. The dosage may vary within this range depending upon the dosage form and route of administration. A therapeutically effective dose can be estimated initially from cell culture assays. A dose may be formulated in cell cultures or animal models to achieve a cellular concentration range that includes the IC50 (i.e., the concentration of the test compound that achieves a half-maximal inhibition of symptoms) as determined in cell culture. Such information can be used to more accurately determine useful doses in humans. The exact formulation, route of administration and dosage can be chosen by the individual physician in view of the patient's condition. (See, e.g., Fingl et al., 1975, In: The Pharmacological Basis of Therapeutics, Ch. 1, p. 1).

Administration could occur at any time during the progression of the disease or disorder of the to be treated, or prior to or after the development of the disease or disorder.

In one embodiment of the first to ninth aspects of the invention, a construct of the invention or a composition comprising a construct of the invention is administered on a daily basis for an extended period to assist with ongoing management of symptoms of a disease or disorder. In another embodiment of the first to ninth aspects of the invention, a construct of the invention or a composition comprising a construct of the invention is administered on a daily basis for an extended period or throughout the subject's life to prevent or delay the development of a disease or disorder.

It will be appreciated that medicaments of the sixteenth to twenty-first aspects of the invention may be formulated for administration of an appropriate dose in accordance with the foregoing.

It will be appreciated that the use in treatment of the twenty-second to twenty-seventh aspects of the invention may involve administration of an appropriate dose in accordance with the foregoing.

It should be appreciated that a method of the first to ninth aspects of the invention may further comprise additional steps such as the delivery of additional agents or compositions to a subject.

In one embodiment of the first to ninth aspects of the invention, the construct, nucleic acid, or nucleic acid vector is administered concurrently with one or more additional therapeutic agent. In one embodiment of the first to ninth aspects of the invention, the construct, nucleic acid, or nucleic acid vector is administered sequentially with one or more additional therapeutic agent.

In one embodiment of the tenth to fifteenth aspects of the invention, the composition comprises one or more additional therapeutic agent.

In one embodiment of the sixteenth to twenty-first aspects of the invention, the medicament comprises one or more additional therapeutic agent.

In one embodiment of the sixteenth to twenty-first aspects of the invention, the medicament is formulated for concurrent administration with one or more additional therapeutic agent. In another embodiment of the sixteenth to twenty-first aspects of the invention, the medicament is formulated for sequential administration with one or more additional therapeutic agent.

In one embodiment of the twenty-second to twenty-seventh aspects of the invention, the use in treatment comprises simultaneous administration with one or more additional therapeutic agent. In another embodiment of the twenty-second to twenty-seventh aspects of the invention, the use in treatment comprises concurrent administration with one or more additional therapeutic agent. In another embodiment of the twenty-second to twenty-seventh aspects of the invention, the use in treatment comprises sequential administration with one or more additional therapeutic agent.

A "therapeutic agent" as used herein, is to be taken broadly to include those agents or drugs that are considered to be useful for or have merit in the treatment of the target disease or disorder associated with hypoxia or the target disease or disorder of the eye. "Therapeutic agents" include, for example, chemotherapeutic drugs, immunotherapeutic drugs, targeted therapy drugs (including, for example, small-molecules or monoclonal antibodies), vaccines and gene therapy. Such drugs may alleviate, reduce, ameliorate, or prevent one or more of the clinical symptoms or diagnostic markers associated with the target disease or disorder associated with hypoxia or the target disease or disorder of the eye.

For example, in a particular embodiment the invention provides a method of treating stroke comprising administering to a subject a construct comprising (a) a targeting carrier peptide derived from the X-protein of the Hepatitis B virus and (b) a peptide capable of interacting with an intracellular domain of connexin43 (Cx43) in combination with a tissue plasminogen activator (tPA) or recombinant tissue plasminogen activator (rtPA). For example, the rtPA may be alteplase (Activase, Actilyse), reteplase (Retavase, Rapilysin), tenecteplase (TNKase), or desmoteplase.

In another example, in a particular embodiment the invention provides a method of treating myocardial infarction comprising administering to a subject a construct comprising (a) a targeting carrier peptide derived from the X-protein of the Hepatitis B virus and (b) a peptide capable of interacting with an intracellular domain of connexin43 (Cx43) in combination with a tissue plasminogen activator (tPA) or recombinant tissue plasminogen activator (rtPA). For example, the rtPA may be alteplase (Activase, Actilyse), reteplase (Retavase, Rapilysin), tenecteplase (TNKase), or desmoteplase.

In a further example, in a particular embodiment the invention provides a method of treating cancer comprising administering to a subject a construct comprising (a) a targeting carrier peptide derived from the X-protein of the Hepatitis B virus and (b) a peptide capable of interacting with an intracellular domain of connexin43 (Cx43) in combination with a therapeutic agent for use in treating cancer. For example, the therapeutic agent may be temozolomide, docetaxel, 5-fluorouracil, doxorubicin, cyclophosphamide, methotrexate, bleomycin, vinblastine, dacarbazine, mustine, vincristine, procarbazine, prednisolone, etoposide, cisplatin, epirubicin, capecitabine, folinic acid, oxaliplatin, or a combination thereof. Persons skilled in the art will readily be able to identify appropriate therapeutic agents and combinations having regard to the cancer to be treated and the disclosure herein.

In certain embodiments of the first to ninth aspects, where the compound is a peptide capable of interacting with an intracellular domain of Cx43, a construct of the invention may be administered locally to achieve a final tissue concentration of the peptide capable of interacting with an intracellular domain of Cx43 in the range of approximately 1 micromolar to approximately 100 micromolar. For example, a construct of the invention may be administered locally to achieve a final tissue concentration of 1, 2, 3, 4 or 5 micromolar. In another example, a construct of the invention may be administered locally to achieve a final tissue concentration of approximately 10, 15 or 20 micromolar. In another example, a construct of the invention may be administered locally to achieve a final tissue concentration of approximately 30, 40, 50, 60, 70, 80, 90, or 100 micromolar. In another example, a construct of the invention may be administered locally to achieve a final tissue concentration in the range of approximately 1 to approximately 20 micromolar. In another example, a construct of the invention may be administered locally to achieve a final tissue concentration in the range of approximately 1 to approximately 5 micromolar, or in the range of approximately 5 to approximately 10 micromolar, or in the range of approximately 10 to approximately 20 micromolar.

For example, in the case of diseases or disorders of the lungs (such as, for example, lung cancer, asbestosis, asthma, bronchiectasis, bronchitis, chronic cough, croup, cystic fibrosis, hantavirus, idiopathic pulmonary fibrosis, influenza, pandemic flu, pertussis, pleurisy, pneumonia, pulmonary embolism, pulmonary hypertension, respiratory syncytial virus, sarcoidosis, or tuberculosisadministration may be via aerosol delivery. For example, in the case of diseases or disorders affected the spinal cord (such as spinal cord tumours) administration may be via an intrathecal drug delivery system. For example, in the case of diseases or disorders of the eye administration may be via periocular injection, intraocular injection, or an intraocular insert or implant.

In particular embodiments of the first, fourth, and/or fifth aspects of the invention where the compound is a peptide capable of interacting with an intracellular domain of Cx43 a construct of the invention may be administered intravitreally to achieve a final intraocular concentration of the peptide capable of interacting with an intracellular domain of Cx43 in the range of approximately 1 micromolar to approximately 100 micromolar. For example, a construct of the invention may be administered intravitreally to achieve a final intraocular concentration of 1, 2, 3, 4 or 5 micromolar. In another example, a construct of the invention may be administered intravitreally to achieve a final concentration of approximately 10, 15 or 20 micromolar. In another example, a construct of the invention may be administered intravitreally to achieve a final intraocular concentration of approximately 30, 40, 50, 60, 70, 80, 90, or 100 micromolar. In another example, a construct of the invention may be administered intravitreally to achieve a final intraocular concentration in the range of approximately 1 to approximately 20 micromolar. In another example, a construct of the invention may be administered intravitreally to achieve a final intraocular concentration in the range of approximately 1 to approximately 5 micromolar, or in the range of approximately 5 to approximately 10 micromolar, or in the range of approximately 10 to approximately 20 micromolar.

In particular embodiments of the first, fourth, and/or fifth aspects of the invention, a construct of the invention may be administered intravitreally at a dose in the range of approximately 0.04 mg to approximately 5 mg. For example, a construct of the invention may be administered intravitreally at a dose of approximately 0.04 mg to 2.5 mg. For example, a construct of the invention may be administered intravitreally at dose of approximately 0.04 mg to 1 mg. For example, a construct of the invention may be administered at a dose of approximately 1 mg to approximately 2.5 mg. For example a construct of the invention may be administered at a dose of approximately 2.5 mg to approximately 5 mg.

In particular embodiments of the first and/or fourth aspects of the invention relating to treatment of cancer and where the compound is a peptide capable of interacting with an intracellular domain of Cx43, a construct of the invention may be administered intratumorally to achieve a final tissue concentration of the peptide capable of interacting with an intracellular domain of Cx43 in the range of approximately 1 micromolar to approximately 100 micromolar. For example, a construct of the invention may be administered intratumorally to achieve a final tissue concentration of 1, 2, 3, 4 or 5 micromolar. In another example, a construct of the invention may be administered intratumorally to achieve a final tissue concentration of approximately 10, 15 or 20 micromolar. In another example, a construct of the invention may be administered intratumorally to achieve a final tissue concentration of approximately 30, 40, 50, 60, 70, 80, 90, or 100 micromolar. In another example, a construct of the invention may be administered intratumorally to achieve a final tissue concentration in the range of approximately 1 to approximately 20 micromolar. In another example, a construct of the invention may be administered intratumorally to achieve a final tissue concentration in the range of approximately 1 to approximately 5 micromolar, or in the range of approximately 5 to approximately 10 micromolar, or in the range of approximately 10 to approximately 20 micromolar.

In particular embodiments of the first and/or fourth aspects of the invention relating to treatment of cancer and where the compound is a peptide capable of interacting with an intracellular domain of Cx43, a construct of the invention may be administered intratumourally at a dose in the range of approximately 0.04 mg to approximately 5 mg. For example, a construct of the invention may be administered intravitreally at a dose of approximately 0.04 mg to 2.5 mg. For example, a construct of the invention may be administered intravitreally at dose of approximately 0.04 mg to 1 mg. For example, a construct of the invention may be administered at a dose of approximately 1 mg to approximately 2.5 mg. For example a construct of the invention may be administered at a dose of approximately 2.5 mg to approximately 5 mg.

In certain embodiments of the second, third, sixth, seventh, eighth and/or ninth aspects of the invention involving a nucleic acid encoding a peptide capable of interacting with an intracellular domain of Cx43, a nucleic acid and/or nucleic acid vector may be administered to achieve an expressed construct such that the tissue concentration of the peptide capable of interacting with an intracellular domain of Cx43 is in the range of approximately 1 micromolar to approximately 250 micromolar. In another example, to achieve a tissue concentration of 1, 2, 3, 4 or 5 micromolar. In another example, to achieve a tissue concentration of approximately 10, 15 or 20 micromolar. In another example, to achieve a tissue concentration of approximately 30, 40, 50, 60, 70, 80, 90, or 100 micromolar. In another example, to achieve a tissue concentration in the range of approximately 1 to approximately 20 micromolar. In another example, to achieve a tissue concentration in the range of approximately 1 to approximately 5 micromolar, or in the range of approximately 5 to approximately 10 micromolar, or in the range of approximately 10 to approximately 20 micromolar.

Data obtained from cell culture assays and animal studies can be used in formulating a range of dosages for use in humans. The dosage may vary within this range depending upon the dosage form and route of administration. A therapeutically effective dose can be estimated initially from cell culture assays. A dose may be formulated in cell cultures or animal models to achieve a cellular concentration range that includes the IC50 (i.e., the concentration of the test compound that achieves a half-maximal inhibition of symptoms) as determined in cell culture. Such information can be used to more accurately determine useful doses in humans.

The exact formulation, route of administration and dosage can be chosen by the individual physician in view of the patient's condition. (See, e.g., Fingl et al., 1975, In: The Pharmacological Basis of Therapeutics, Ch. 1, p. 1).

Administration could occur at any time during the progression of the disease or disorder to be treated, or prior to or after the development of the disease or disorder, having regard to the particular disease or disorder being treated. For example, when the disease or disorder is AMD administration could occur during early, intermediate, and/or late AMD. For example, when the disease or disorder is diabetic retinopathy administration could occur when there is mild non-proliferative retinopathy, when there is moderate non-proliferative retinopathy, when there is severe nonproliferative retinopathy, and/or when there is proliferative diabetic retinopathy. For example, when the disease or disorder is stroke, administration could occur prior to reperfusion, during reperfusion or after reperfusion, and could be in conjunction with a clot breakdown compound (such as, for example, tissue plasminogen activator, Alteplase, Streptokinase, Tenecteplase or Reteplase) or clot retrieval through surgical means; particularly but not exclusively where the construct being administered comprises a peptide capable of interacting with an intracellular domain of Cx43. Administration could follow treatment with a clot breakdown compound (such as, for example, tissue plasminogen activator, Alteplase, Streptokinase, Tenecteplase or Reteplase) or following clot retrieval through surgical means; particularly but not exclusively where the construct being administered comprises a peptide capable of interacting with an intracellular domain of Cx43. For example, when the disease or disorder is a cancer administration could occur at any stage, such as when judged through the TNM grading system where T refers to the size and extent of the main tumour, the N refers to nearby lymph nodes that have cancer, and the M refers to whether the cancer has metastasized. Administration could be at Stage 0 when abnormal cells are present but have not spread to nearby tissue, or at Grades 1, II or II when cancer is present (and the higher the number the larger the cancer and the more it has spread into nearby tissues), or Stage IV when the cancer has spread to distant parts of the body.

In one embodiment of the fourth to ninth aspects of the invention, a construct, nucleic acid, or nucleic acid vector of the invention, or a composition comprising a construct, nucleic acid, or nucleic acid vector of the invention, is administered on a daily basis for an extended period to assist with ongoing management of symptoms of a disease or disorder. In another embodiment of the fourth to ninth aspects of the invention, a construct, nucleic acid, or nucleic acid vector of the invention, or a composition comprising a construct, nucleic acid, or nucleic acid vector of the invention, is administered on a daily basis for an extended period or throughout the subject's life to prevent or delay the development of a disease or disorder.

In one embodiment of the seventeenth aspect of the invention or the sixteenth aspect of the invention wherein the compound is a peptide capable of interacting with an intracellular domain of Cx43, the medicament is formulated for systemic administration of a dose of the peptide capable of interacting with an intracellular domain of Cx43 in the range of approximately 70 mg to 1,750 mg.

In one embodiment of the seventeenth aspect of the invention or the sixteenth aspect of the invention wherein the compound is a peptide capable of interacting with an intracellular domain of Cx43, the medicament is formulated for systemic administration of a dose to achieve a circulating concentration of the peptide capable of interacting with an intracellular domain of Cx43 in the range of approximately 5 micromolar to 20 micromolar.

In one embodiment of the seventeenth aspect of the invention or the sixteenth aspect of the invention wherein the compound is a peptide capable of interacting with an intracellular domain of Cx43, the medicament is formulated for administration by systemic infusion of a dose to achieve a circulating concentration of the peptide capable of interacting with an intracellular domain of Cx43 in the range of approximately 2.5 micromolar to 250 micromolar.

In one embodiment of the seventeenth aspect of the invention or the sixteenth aspect of the invention wherein the compound is a peptide capable of interacting with an intracellular domain of Cx43, the medicament is formulated for topical administration of a dose to achieve a tissue concentration of the peptide capable of interacting with an intracellular domain of Cx43 in the range of approximately 1 micromolar to 100 micromolar.

In one embodiment of the sixteenth aspect of the invention wherein the compound is a peptide capable of interacting with an intracellular domain of Cx43, the medicament is formulated for local administration of a dose to achieve a tissue concentration of the peptide capable of interacting with an intracellular domain of Cx43 in the range of approximately 1 micromolar to 100 micromolar.

In one embodiment of the seventeenth aspect of the invention or the sixteenth aspect of the invention wherein the compound is a peptide capable of interacting with an intracellular domain of Cx43, the medicament is formulated for intravitreal administration of a dose to achieve a tissue concentration of the peptide capable of interacting with an intracellular domain of Cx43 in the range of approximately 1 micromolar to 100 micromolar.

In one embodiment of the sixteenth aspect of the invention wherein the compound is a peptide capable of interacting with an intracellular domain of Cx43, the medicament is formulated for intratumoural administration of a dose to achieve a tissue concentration of the peptide capable of interacting with an intracellular domain of Cx43 in the range of approximately 1 micromolar to 100 micromolar.

In one embodiment of the sixteenth aspect of the invention wherein the compound is a peptide capable of interacting with an intracellular domain of Cx43, the medicament is formulated for local administration of a dose in the range of approximately 0.04 mg to approximately 5 mg.

In one embodiment of the seventeenth aspect of the invention or the sixteenth aspect of the invention wherein the compound is a peptide capable of interacting with an intracellular domain of Cx43, the medicament is formulated for intravitreal administration of a dose in the range of approximately 0.04 mg to approximately 5 mg.

In one embodiment of the sixteenth aspect of the invention wherein the compound is a peptide capable of interacting with an intracellular domain of Cx43, the medicament is formulated for intratumoural administration of a dose in the range of approximately 0.04 mg to approximately 5 mg.

In one embodiment of the twenty-third aspect of the invention or the twenty-second aspect of the invention wherein the compound is a peptide capable of interacting with an intracellular domain of Cx43, the use is by administration of a dose of the peptide capable of interacting with an intracellular domain of Cx43 in the range of approximately 70 mg to 1,750 mg.

In one embodiment of the twenty-third aspect of the invention or the twenty-second aspect of the invention wherein the compound is a peptide capable of interacting with an intracellular domain of Cx43, the is by systemic administration of a dose of the peptide capable of interacting with an intracellular domain of Cx43 in the range of approximately 70 mg to 1,750 mg.

In one embodiment of the twenty-third aspect of the invention or the twenty-second aspect of the invention wherein the compound is a peptide capable of interacting with an intracellular domain of Cx43, the use is by administration of a dose to achieve a circulating concentration of the peptide capable of interacting with an intracellular domain of Cx43 in the range of approximately 2.5 micromolar to 250 micromolar.

In one embodiment of the twenty-third aspect of the invention or the twenty-second aspect of the invention wherein the compound is a peptide capable of interacting with an intracellular domain of Cx43, the is by administration of a dose to achieve a tissue concentration of the peptide capable of interacting with an intracellular domain of Cx43 in the range of approximately 1 micromolar to 100 micromolar.

In one embodiment of the twenty-second aspect of the invention wherein the compound is a peptide capable of interacting with an intracellular domain of Cx43, the use is by local administration of a dose in the range of approximately 0.04 mg to approximately 5 mg.

In one embodiment of the twenty-third aspect of the invention or the twenty-second aspect of the invention wherein the compound is a peptide capable of interacting with an intracellular domain of Cx43, the use is by intravitreal administration of a dose in the range of approximately 0.04 mg to approximately 5 mg.

In one embodiment of the twenty-second aspect of the invention wherein the compound is a peptide capable of interacting with an intracellular domain of Cx43, the use is by intratumoural administration of a dose in the range of approximately 0.04 mg to approximately 5 mg.

In one embodiment of the nineteenth and/or twenty-first aspects of the invention or the eighteenth and/or twentieth aspect of the invention wherein the compound is a peptide capable of interacting with an intracellular domain of Cx43, the medicament is formulated for administration of a nucleic acid and/or a nucleic acid vector at a dose to achieve an expressed construct such that the tissue concentration of the peptide capable of interacting with an intracellular domain of Cx43 is in the range of approximately 1 micromolar to approximately 250 micromolar.

In one embodiment of the nineteenth and/or twenty-first aspects of the invention or the eighteenth and/or twentieth aspect of the invention wherein the compound is a peptide capable of interacting with an intracellular domain of Cx43, the is by administration of a dose to achieve an expressed construct such that the tissue concentration of the peptide capable of interacting with an intracellular domain of Cx43 is in the range of approximately 1 micromolar to approximately 250 micromolar.

To the extent that a peptide of use in accordance with the present invention or a construct of the invention (for example, a targeting carrier peptide derived from the X-protein of the Hepatitis B virus or a peptide capable of interacting with an intracellular domain of Cx43) may be produced by recombinant techniques, the invention provides: nucleic acids encoding peptides of use in the invention, nucleic acids encoding constructs of the invention, vectors comprising nucleic acids encoding peptides of use in the invention, and vectors comprising nucleic acids encoding constructs of the invention, which may aid in cloning and expression of peptides.

In addition, it should be appreciated that nucleic acids encoding constructs of the invention and of use in the invention and/or nucleic acid vectors comprising nucleic acids encoding constructs of the invention and of use in the invention could be used (including therapeutically); for example in accordance with the second, third, sixth, seventh, eighth, ninth, twelfth to fifteenth, and/or twenty-fourth to twenty-seventh aspects as detailed herein.

For example, a nucleic acid/expression vector encoding the construct could be administered to a subject or contacted to a cell or population of cells, with the peptide/construct subsequently being expressed. Accordingly, the invention includes nucleic acids and nucleic acid vectors suitable for these purposes.

It should be understood that a nucleic acid of the invention, or of use in accordance with the invention, is an "isolated" or "purified" nucleic acid. An "isolated" or "purified" nucleic is one which has been identified and separated from the environment in which it naturally resides, or artificially synthesized. It should be appreciated that these terms do not reflect the extent to which the nucleic has been purified or separated from the environment in which it naturally resides. Nucleic acids of the invention or of use in accordance with the invention may be isolated from natural sources, or preferably derived by chemical synthesis or recombinant techniques which will be readily known to persons skilled in the art.

Those of general skill in the art to which the invention relates will readily be able to identify a variety of nucleic acids which encode peptides and functionally equivalent variants of use in the invention (for example, a targeting carrier peptide derived from the X-protein of the Hepatitis B virus or a peptide capable of interacting with an intracellular domain of Cx43) and constructs of the invention on the basis of the amino acid sequences provided herein, the genetic code and the understood degeneracy therein, and published nucleic acid sequences (for example, see Guo, Y. and Hou, J. Establishment of the consensus sequence of hepatitis B virus prevailing in the mainland of China. Zhonghua M M Guo Wei Sheng Wu Ji Mian Yi Xue Za Zhi 19: 189-2000, 1999).

However, by way of example, the following nucleic acids are suitable in respect of the targeting carrier peptide derived from the X-protein of the Hepatitis B virus:

ctt tgt cta cgt ccc (SEQ ID NO: 73)
(peptide comprising LCLRP (SEQ ID NO: 5))

ctt tgt cta cgt ccc gtc ggc (SEQ ID NO: 74)
(peptide comprising LCLRPVG (SEQ ID NO: 6))

ctt tgt cta cgt ccc gtc ggc gct gaa
(SEQ ID NO: 75)
(peptide comprising LCLRPVGAE (SEQ ID NO: 7))

ctt tgt cta cgt ccc gtc ggc gct gaa tcc cgc
(SEQ ID NO: 76)
(peptide comprising LCLRPVGAESR (SEQ ID NO: 8))

ctt tgt cta cgt ccc gtc ggc gct gaa tcc cgc gga
cga ccc gtc tcg ggg ccg ttt ggg (SEQ ID NO: 77)
(peptide comprising LCLRPVGAESRGRPVSGPFG
(SEQ ID NO: 10))

gtc ctt tgt cta cgt (SEQ ID NO: 78)
(peptide comprising VLCLR (SEQ ID NO: 20))

ctt tgt cta cgt (SEQ ID NO: 79)
(peptide comprising LCLR (SEQ ID NO: 16))

By way of further example, skilled persons will readily be able to derive nucleic acid sequences encoding for peptides capable of interacting with the intracellular domain of Cx43 with reference to published sequence information, for example GenBank Accession number U64573.1 available at www.ncbi.nlm.nih.gov, and the reader is specifically directed to this database by way of reference and the entry is included in the general description of the invention herein.

Nucleic acid vectors and/or nucleic acid constructs will generally contain heterologous nucleic acid sequences. That is, the nucleic acid vectors and/or nucleic acid constructs contain nucleic acid sequences that are not adjacent to sequences encoding the peptide of use in the invention in the nucleic acid coding for the native protein/peptide from which the peptide of use in the invention is derived. The nucleic acid vectors and/or nucleic acid constructs may also contain nucleic acid sequences that do not code for the construct per se. For example, nucleic acid vectors and/or nucleic acid constructs may contain regulatory sequences such as promoters, operators, repressors, enhancers, termination sequences, origins of replication, and other appropriate regulatory sequences as are known in the art. Further, they may contain secretory sequences to enable an expressed protein to be secreted from its host cell. In addition, nucleic acid expression constructs may contain fusion sequences (such as those that encode a heterologous amino acid sequence) which lead to the expression of inserted nucleic acid sequences of the invention as fusion proteins or peptides.

Heterologous nucleic acid sequences of use may include, for example, those that code for amino acid sequences which can aid in subsequent isolation and purification of the peptide (for example, ubiquitin, his-tag, a c-myc tag, a GST tag, or biotin). Heterologous nucleic acid sequences may also include those that code peptide linkers which aid in linking the peptide to another compound to form a construct of the invention, as described above.

The nucleic acid constructs or vectors may be either RNA or DNA, either prokaryotic or eukaryotic, and typically are viruses or a plasmid. Suitable nucleic acid constructs are preferably adapted to deliver a nucleic acid of the invention into a host cell and are either capable or not capable of replicating in such cell. Recombinant nucleic acid constructs comprising nucleic acids of the invention may be used, for example, in the cloning, sequencing, and expression of nucleic acid sequences of the invention.

Those of skill in the art to which the invention relates will recognise many nucleic acid constructs suitable for use in the present invention. However, the use of cloning vectors such as pUC and pBluescript and expression vectors such as pCDM8, adeno-associated virus (AAV) or lentiviruses are of particular use.

In accordance with the invention, transformation of a nucleic acid vector into a host cell can be accomplished by any method by which a nucleic acid sequence can be inserted into a cell. For example, transformation techniques include transfection, electroporation, microinjection, lipofection, adsorption, cell-penetrating carrier peptide delivery, and biolistic bombardment.

As will be appreciated, transformed nucleic acid sequences of the invention may remain extrachromosomal or can integrate into one or more sites within a chromosome of a host cell in such a manner that their ability to be expressed is retained.

Any number of host cells known in the art may be utilised in cloning and expressing nucleic acid sequences of use in the invention and/or nucleic acid sequences of the invention. For example, these include but are not limited to microorganisms such as bacteria transformed with recombinant bacteriophage DNA, plasmid DNA or cosmid DNA expression vectors; yeast transformed with recombinant yeast expression vectors; insect cell systems infected with recombinant virus expression vectors (e.g., baculovirus); animal cell systems such as CHO (Chinese hamster ovary) cells using the pEE14 plasmid system; plant cell systems infected with recombinant virus expression vectors (e.g., cauliflower mosaic virus, CaMV; tobacco mosaic virus, TMV) or transformed with recombinant plasmid expression vectors (e.g., Ti plasmid).

A recombinant peptide of use in accordance with the invention or a recombinant peptide construct of the invention may be recovered from a transformed host cell, or culture media, following expression thereof using a variety of techniques standard in the art. For example, detergent extraction, sonication, lysis, osmotic shock treatment and inclusion body purification. The protein may be further purified using techniques such as affinity chromatography, ion exchange chromatography, filtration, electrophoresis, hydrophobic interaction chromatography, gel filtration chromatography, and chromatofocusing.

Additional or alternative methodology for recombinant expression of peptides of the invention may be obtained from Sambrook, and Maniatis, Molecular Cloning: A Laboratory Manual, Second Edition, Cold Spring Harbor Laboratory Press, Cold Spring Harbor, N.Y. (1989), for example.

Examples of peptide therapeutic agents of use in the aspects of the present invention involving treatment of diseases and/or disorders of the eye, such as age-related macular degeneration, diabetic retinopathy, ocular tumour, and/or retinal stroke, include an antisense oligonucleotide to reduce production of proteins in the inflammatory or complement pathway such as Ang2, Tie2, integrin or Cx43, or an antisense oligonucleotide interfering with production of any VEGF or PDGF or their receptors may be used. A further example is the use of an anti-VEGF and/or anti-PDGF antisense oligonucleotide to reduce neovascularisation in age related macular degeneration, diabetic retinopathy or a cancer.

Constructs of the invention may be produced using recombinant cloning and expression techniques, and accordingly the invention should be taken to include nucleic acids encoding the constructs and vectors comprising such nucleic acids.

Skilled persons will readily appreciate the sequence of nucleic acids encoding constructs of the invention having regard to the nucleic acid and peptide sequences of the targeting carrier peptides described herein before and the nature of the peptide compound to be delivered to a cell. Similarly, skilled persons will readily appreciate appropriate vectors for cloning and expressing the constructs. However, by way of example, the nucleic acid vectors (for example, pUC vectors, adeno-associated virus, lentivirus) and techniques detailed elsewhere herein (including those described in WO 91/09958, WO 03/064459, WO 00/29427, and WO 01/13957 for example) may be used.

Certain terms may be referred to herein in the plural; for example, "cells", "compounds", "agents". This should be taken to include reference to the singular, unless the context requires otherwise.

EXAMPLES

Materials and Methods
Peptide Sequence

Gap19 (KQIEIKKFK [SEQ ID NO: 3]), the fusion peptide designated XG19 (clrpv KQIEIKKFK [SEQ ID NO: 1]) and the fusion peptide TAT-Gap19 (YGRKKRRQRRRKQIEIKKFK [SEQ ID NO: 80]) as well as FITC labelled peptides were all obtained from ChinaPeptide Co Ltd, at 95% purity. Peptide5 (VDCFLSRPTEKT [SEQ ID NO: 81]) was purchased from Auspep. The peptides were resuspended in PBS (phosphate buffered saline) and stored at −20° C.

Cell culture and maintenance Unless otherwise mentioned, all cell culture reagents were purchased from Gibco® or Invitrogen™ (Life Technologies). ARPE-19 cells are from a human retinal pigment epithelium cell line purchased from American Type Culture Collection (ATCC), and were maintained in T25 flasks in DMEM/F12 (DMEM/F-12, GlutaMAX™ medium containing 10% heat inactivated foetal bovine serum (FBS), and 1% Antibiotic-Antimicotic (Sigma)) at 37° C. with 5% CO2.

Primary human retinal microvascular endothelial cells (hRMEC; Neuromics) were cultured and maintained in T25 flasks in EGM-2™ BulletKit™ media (Lonza) containing endothelial basal media (EBM-2; Lonza) and EGM-2 SingleQuots™ (Lonza), supplemented with 10% fetal bovine serum and 1% Antibiotic-Antimicotic (Sigma) at 37° C. with 5% CO2. VEGF was excluded from the EGM-2 media.

Cells were grown to 70-80% confluence, split once or twice weekly and were maintained at less than thirty passages. For experiments, cells were harvested with TrypLE™ Express, centrifuged at 1500 rpm for 7 mM, resuspended in culture medium, and counted using trypan blue and the Neubauer haemocytometer. The required concentration of cells was plated and grown overnight to allow them to attach to the bottom of the well.

Hyperglycaemia and Inflammation Solution

Hyperglycaemia and inflammation solution was produced by the addition of glucose to DMEM/F12, GlutaMAX™ to achieve a final glucose concentration of 32.5 mM. The inflammatory cytokines TNFα and Il-1β (PeproTech) were added to achieve a final concentration of 10 ng/ml each. Antibiotic-Antimycotic was added to the solution to achieve a 1% concentration. The solution was made fresh before application to cells.

Image Acquisition and Analysis

Visualisation of cells and tissues was carried out using an Olympus BX-10 confocal microscope with a FV-1000 laser scanning confocal system. Images were acquired using Olympus FV-10 software and area measurements were made using ImageJ. All statistical analysis was carried out using Graphpad Prism 7 software.

Cellular Uptake

ARPE-19 or hRMEC cells were harvested and seeded in 8-well chamber slides at a density of 2×105 cells/ml in 0.4 ml of DMEM/F12 or EGM-2™ BulletKit™ media and incubated over 2 nights at 37° C., 5% $CO_2$. Peptides or control channel blockers, carbenoxolone (CBX) (Sigma) or lanthanum chloride ($LaCl_3$; Sigma) were mixed with DMEM/F12 or EGM-2™ BulletKit™ media at appropriate concentrations and applied onto cells for 1 h at 37° C., 5% $CO_2$. For cell uptake under hypoxic conditions, peptides were delivered in hypoxic, acidic ion-shifted Ringers (HAIR) solution (13) for 1 h at 37° C., 5% CO2. For cell uptake under hyperglycaemia and inflammation conditions peptides were delivered in hyperglycaemia and inflammation solution for 24 h at 37° C., 5% $CO_2$. The solutions were removed and cells were washed in PBS and fixed in 4% formaldehyde PBS with nuclei were counterstained with DAPI. Coverslips were mounted in anti-fade medium (Citifluor™ AF1) and cells were visualised by confocal microscopy.

MTT Assay

ARPE-19 cells were exposed to DMEM/F12 (normal medium) or HAIR solution for 1 h. XG19 was mixed in DMEM/F12 or HAIR solution and applied to ARPE-19 cells at 0, 5, 10 or 20 μM concentrations for either 1 or 24 h at 37° C., 5% $CO_2$. After the incubation period, the solutions in each well were removed and replaced with 0.5 mg/mL, MTT (Thermo Fisher Scientific) in PBS and incubated for 4 h at 37° C. and 5% $CO_2$. The MTT/PBS solution was then removed and replaced with HCl-isopropanol solution (0.04 M) to dissolve formed formazan. The intensity of purple colour was quantified by measuring absorbance at 570 nm with correction of interference at 650 nm (BioTek Synergy HT).

EthD-1 Uptake

Peptides were applied onto cells for uptake as previously mentioned. Peptide solutions were removed from the cells exposed to 2 μM ethidium homodimer-1 (EthD-1) in either Hanks Buffered Salt Solution (137 mM NaCl, 5.4 mM KCl, 0.25 mM $Na_2HPO_4$, 0.1 g glucose, 0.44 mM $KH_2PO_4$, 1.0 mM $MgSO_4$, 4.2 mM $NaHCO_3$)+EGTA (5 mM) (low calcium solution) to open hemichannels or high calcium (Ca') solution (Hanks Buffered Salt Solution+1.3 mM $CaCl_2$)) for 30 mM at 37° C., 5% $CO_2$. The solutions were removed, cells were washed in PBS and fixed in 4% formaldehyde PBS before counterstaining nuclei with DAPI. Coverslips were mounted in anti-fade medium (Citifluor™ AF1) and slides were imaged.

ATP Release Assay

Peptides were applied onto cells for uptake studies as previously described. Peptide solutions were removed from the cells, which were then exposed to either low calcium ($Ca^{2+}$) solution or HAIR solution to open hemichannels or high calcium solution to close hemichannels for 30 mM at 37° C., 5% $CO_2$. Solutions were transferred into a black 96 well plate and ATP measurements were performed as per the instructions of the ATP luminescence kit (Sigma) and using a Victor X Light luminescence plate reader (Perkin Elmer 2030).

Gap Junction Assay

Peptides were applied onto cells for uptake as previously mentioned. Peptide solutions were removed from the cells and the cells were exposed to 0.1% luciferase yellow/PBS dye (LY). A vertical and horizontal scrape was created in the cell monolayer using a pipette tip. The cells were then incubated at room temperature for 15 min. The LY dye solution was removed, cells were washed in PBS and fixed in 4% formaldehyde PBS with nuclei counterstained with DAPI. Coverslips were mounted in anti-fade medium (Citifluor™ AF1) and slides were imaged.

Syndecan-4 Labelling of ARPE-19 Cells

ARPE-19 cells were treated with either DMEM/F-12, hyperglycaemia and inflammation solution, or HAIR solution for 1 h before washing the cells in PBS and fixing in 4% formaldehyde/PBS at room temperature for 10 min. The formaldehyde solution was washed off with PBS and the cells were labelled with primary antibody (anti-Syndecan-4 (R&D Systems)) overnight. The primary antibody was then washed off with PBS before applying the secondary antibody (donkey anti-goat 488) and DAPI in PBS for 1 h at RT in a humid box. Coverslips were mounted in anti-fade medium (Citifluor™ AF1) and slides were imaged.

Laser Induced Choroidal Neovascularisation Mouse Model

General Procedure

Female C57BL/6 mice were acquired from the University of Auckland, Vernon Jansen Unit (VJU) and were 6 weeks of age at Day 0 of experimentation. All animals were housed in the VJU for the duration of the study and had access to food and water ad libitum. All animal procedures were approved by the University of Auckland Animal Ethics Committee and were in accordance with The Association for Research in Vision and Ophthalmology (ARVO) Statement for the Use of Animals in Ophthalmic and Visual Research guidelines (www.arvo.org/About/policies/statement-for-the-use-of-animals-in-ophthalmic-and-vision-research/)(. Mice were weighed before anesthetising them via intraperitoneal injection of a ketamine (50 mg/kg)/domitor (0.5 mg/kg) mixture and placed onto the mouse stage for laser photocoagulation or ocular assessments (fundus imaging and optical coherence tomography (OCT). The mouse stage was heated to maintain the mouse body temperature and prevent cataract formation. Pupils were dilated with 1% tropicamide dilating eye drops to increase the visualisation of the retina. Lubricating Poly Gel was applied to each eye to act as a coupling medium between the Micron IV eyepiece (Phoenix Research Labs) and the ocular surface. After completion of laser photocoagulation or ocular assessments, the lubricating gel was washed off with saline and antibiotic solution was applied onto both eyes to prevent infection. Mice were then woken with an intraperitoneal injection of Atipamezole (5 mg/kg) and allowed to recover on a 35° C. warming pad. On day 8 all animals were culled by $CO_2$ asphyxiation and cervical dislocation. The eyes were enucleated, fixed in 4% paraformaldehyde in PBS, frozen in optimum cutting temperature compound and stored at −80° C. before sectioning onto slides for immunohistochemistry analysis.

Laser Photocoagulation

The laser injector was attached to the Micron IV and the laser was assembled as per the manufacturer's guidelines. The mouse retina was viewed using the bright field live fundus image and the optic disc was centralised as per methods used by Gong et al. 2015 (34). The laser aiming beam was visualised on the fundus image before creating four sequential laser burns at equal distance (2 disc diameters) from the optic disc using a green argon laser pulse of 532 nm, a fixed diameter of 50 µm, at duration of 70 ms and 240 mW power. Major blood vessels were avoided when creating laser burns. Fundus images were taken immediately after laser photocoagulation for up to 60 sec to observe for subretinal bubble formation and lesion growth.

Fundus Imaging and Measurements

The fundus/OCT eye piece was attached to the Micron IV as per the manufacturer's guidelines. Bright field fundus images were taken on day 0 (before and after laser photocoagulation), 1 and 7. Cross-sectional area measurements were made using ImageJ software.

Optical Coherence Tomography (OCT)

The fundus/OCT eye piece was attached to the Micron IV as per the manufacturer's guidelines (Phoenix Research Labs). The bright field live fundus image was used to orientate the OCT reference arm and acquire OCT scans using the Micron OCT software. Several OCT scans were taken over each lesion from superior to inferior. OCT images were qualitatively assessed by observing classic signs of choroidal neovascularisation such as Bruch's membrane rupture (hypo-reflective region in the RPE/choroid layer) at day 0, butterfly-like lesions at day 1 and hyper-reflectivity increase in the retinal layers at the site of the lesion at day 7. Ellipsoid measurements of lesions on day 7 were acquired using ImageJ software using the methods described by Sulaiman et al. 2015 (35).

CNV Mouse Model Study

Fifteen mice were acquired and maintained as described above in groups of five over three weeks. Mice were anesthetized and laser photocoagulation was carried out and fundus images were acquired as described above Immediately following laser photocoagulation in both eyes, mice received an intraperitoneal injection of XG19 in saline at concentrations of 25 µM (low dose) or 250 µM (high dose) or saline alone before acquiring fundus and OCT images. Fundus and OCT images were acquired on days 1 and 7 as described above. On day 8, the animals were culled and ocular tissues excised and processed for immunohistochemistry as described above.

Rat Sepsis and Acute Pancreatitis models

This animal study was approved by the University of Auckland Animal Ethics Committee and adhered to standards outlined in the "Animal Research: Reporting of In Vivo Experiments (ARRIVE; www.nc3rs.org.uk/arrive-guidelines) guidelines". Male Sprague Dawley rats (-450 g) were fed with 18% protein rodent diet and allowed ad libitum access to food and water before surgery. General anaesthesia was induced with 3-4% isofluorane and 02 at 2 L/min, and maintained with 1.5-2.5% isoflurane with 02 at 2 L/min. The rat was placed on a warming plate to keep the body temperature at 36-38° C., and their temperature was monitored by a rectal probe. A 14G modified angiocath was inserted into trachea and connected to a small animal mechanical ventilator. The inspired 02/air was administered at 40-45%, and the respiratory rate and peak inspiratory pressure set at 60-80 breaths/min and 14-18 $cmH_2O$, respectively. The end tidal $CO_2$ was maintained at 35-45 ml/L and monitored by a capnograph. Maintenance fluid (0.9% NaCl) was administered into the right femoral vein, and a 2F pressure transducer was inserted into the right femoral artery to monitor the mean arterial pressure.

For the moderate severity Acute Pancreatitis (AP) model, the bile duct was temporally occluded and the main pancreatic duct was cannulated using a 24 G angiocath and slowly infused with 5% sodium taurocholate solution at 0.1 ml/min until reaching 1 ml/kg body weight. The angiocath was removed 10 min after the infusion, the bile duct opened, and the pancreatic duct was ligated to prevent the efflux.

For the Sepsis model, 0.5 cm incision was made on the cecum and faeces spread to all four quadrants of abdomen. The intestine was returned back to the abdominal cavity. Induction of AP and sepsis took 10-15 min. Sham rats underwent the same anaesthesia and transverse abdominal incision protocol as the disease models, but without any specific disease induction. The total duration for sham rats was matched to the AP and Sepsis models in order to control the effect from anaesthesia. Maintenance fluid was continuously administered into the rats, but its infusion rate was dependent on the rat model: a minimum of 6 ml/kg/hr was selected for AP model to give a mild-moderate disease severity, whereas a minimum of 18 ml/kg/hr was given to the sepsis model to sufficiently resuscitate the rats to ensure survival during the 5 h experimental period. Mortality rate on each model was: 15% for sepsis and 0% for AP and sham, respectively.

During 5 hr of disease progression, intraoperative mean arterial pressure, heart rate and body temperature were continuously monitored using the LabChart 5. At the end of 5 h disease progression, blood was collected from the inferior vena cava into K2EDTA vacutainers. Lungs were excised and mounted in optimal cutting temperature compound and frozen at −80° C. before cutting and mounting 12 µm sections onto slides for immunohistochemistry.

Human Sinus Tissues

Mucosal biopsies were obtained from the middle meatus in three patients undergoing functional endoscopic sinus surgery (FESS) for chronic rhinosinusitis (CRS). The control group consisted of three patients with obstruction but no sinusitis undergoing septoplasty. Biopsies were mounted in optimal cutting temperature compound and snap frozen in liquid nitrogen before cutting and mounting 12 µm sections onto slides for immunohistochemistry Glioma Mouse Model The syngeneic SMA560 glioma tumour cells ($1 \times 10^5$ SMA560 glioma cells) was inserted via a 10 µl intracranial injection (27 gauge needle) into the brain of anaesthetized VmDK mice through the coronal suture after a small incision was made in the scalp. The mice were culled prior to developing neurological symptoms 14 days post tumour cell implantation. The brains were removed, cut with a scalpel blade through the injection site and placed in neutral buffered formalin for histological processing then embedded in paraffin before cutting and mounting 12 µm sections onto slides for immunohistochemistry.

A431 and SKOV3 Tumour Tissue

Human tumour cells A431 and SKOV3 were administered via subcutaneous injection into the flank of nude immunocompromised mice. The tumours were harvested and frozen in optimum cutting temperature compound and stored at −80° C. before sectioning onto slides for immunohistochemistry analysis.

Immunohistochemistry of Tissue Sections

Before beginning immunohistochemistry labelling of paraffin embedded brain tissue sections (12 µm) from mouse glioma model, the sections were deparaffinised by washing in xylene twice for three minutes, washing in xylene 1:1 with 100% ethanol for three minutes, washing in 100% ethanol twice for three minutes, 95% ethanol for three minutes, 70% ethanol for three minutes, 50% ethanol for three minutes before rehydrating the slides by rinsing in cold running water. Antigen was retrieved by applying sodium citrate buffer (10 mM sodium citrate, 0.05% Tween 20, pH 6.0) for 1 h in a pressure cooker. Slides were then blocked in 1% bovine serum albumin (BSA)/PBS for 1 h at room temperature.

Frozen tissue (mounted in optimal cutting temperature compound) sections (12 µm) from human donor retinas (normal and diabetic retinopathy), human sinus tissue (normal and CRS), mouse ocular tissues (laser induced CNV mouse model), rat lung tissue (AP and sepsis models) and tumour tissues (A431 and SKOV3), were dried overnight at room temperature and then fixed in a mixture of 25% absolute ethanol and 75% acetone for 10 min at room temperature in a fume hood. Sections were dried at room temperature for 10 min before blocking in 1% bovine serum albumin (BSA)/PBS for 1 h at room temperature.

The blocking solution was tapped off and sections were covered with 20 µg/ml of -Syndecan-4 antibody (R&D Systems) in 1% BSA/PBS overnight at room temperature in a humid box. Control sections were treated in 1% BSA/PBS alone. Antibodies were washed off using 0.05% Tween20/PBS and tissues were covered in solutions containing secondary antibodies (donkey anti-goat 488) and DAPI in 1% BSA/PBS for 2 h at room temperature in a humid box. Sections were washed in 0.05% Tween20/PBS. Coverslips were mounted in anti-fade medium (Citifluor™ AF1) and slides were imaged.

Results

Example 1

XG19 uptake into hRMEC and ARPE-19 cells is more efficient than Gap19 alone

The uptake of XG19 was tested in vitro using primary hRMEC (FIG. 1) as well as immortalized ARPE-19 cells (FIG. 2). Cellular uptake of XG19 was compared to Gap19 to observe if the addition of the LCLRPV (SEQ ID NO: 2) sequence improved cellular uptake.

XG19 uptake by hRMEC cells occurred in a dose dependant manner as observed by increasing FITC fluorescence (white area in the FITC panel of FIG. 1) with increasing concentration of XG19. In this assay uptake was observed even at the lowest concentration of XG19 (10 µM). Gap19 uptake was undetectable even up to 50 µM as no fluorescence was observed and was comparable to the no peptide control (as indicated by the absence of white area in the FITC panel of the respective treatments, FIG. 1). Some uptake was observed at 100 µM Gap19 however this was still lower than 10 µM XG19. Therefore, the addition of LCLRPV (SEQ ID NO: 2) to Gap19 increased the uptake efficiency of Gap19 into hRMEC cells. This assay showed that XG19 could penetrate hRMECs and the addition of LCLRPV (SEQ ID NO: 2) to Gap19 improved uptake in these cells.

Cellular uptake of XG19 into ARPE-19 cells occurred in a dose dependant manner as observed by increasing FITC fluorescence (white area in the FITC panel of FIG. 2) with increasing XG19 concentration. Gap19 alone was undetectable inside the cells up to 100 µM, similar to the no peptide control (as indicated by the absence of white area in the FITC panel of Gap19 treatments and no peptide treatment). Therefore, the addition of LCLRPV (SEQ ID NO: 2) to Gap19 improved the uptake efficiency of Gap19 into ARPE-19 cells as a greater amount of XG19 was delivered inside the cells at lower Gap19 concentrations.

Since ARPE19 is an immortalised cell line it was easier to culture and could survive multiple passages whereas primary cells were only reliable for a very limited number of passages.

For this reason the remaining experiments were carried out using ARPE-19 cells.

Example 2

TAT-Gap19 Uptake into ARPE-19 Cells is More Efficient than XG19 or Gap19 Alone, However XG19 does not Localise to the Nucleus The uptake efficiency of Gap19 has previously been improved by combining Gap19 with TAT peptide to create TAT-Gap19 (6, 7). The uptake efficiency of XG19 was compared to Gap19 and TAT-Gap19 in ARPE-19 cells (FIG. 3). TAT-Gap19 uptake by ARPE-19 cells occurred in a dose dependant manner as observed by increased FITC fluorescence (white area in the FITC panel of FIG. 3) with increasing concentrations of TAT-Gap19. Uptake was observed even at the lowest concentration of TAT-Gap19 (10 µM) and cells were saturated with TAT-Gap19 at 20 µM. Gap19 uptake was undetectable even up to 100 µM (as indicated by the absence of white area in the FITC panel of FIG. 3) which was comparable to the no peptide control.

While XG19 uptake was detected as low as 10 µM increasing up to 50 µM the overall uptake of TAT-GAP19 was much greater than for XG19 at all the tested concentrations (as indicated by increased white area in FITC panel of FIG. 3.). This could be due to the difference in uptake mechanism between the two peptides. TAT enters cells largely through macropinocytosis among other mechanisms (8, 9) while LCLRPV (SEQ ID NO: 2) enters cells in a Syndecan-4 specific manner (10,11). Therefore, while the uptake of TAT-Gap19 is more efficient than XG19 in this assay due to its multiple uptake mechanisms, it highlights its non-specificity with regards to targeting certain cell types, as uptake is not limited by a single factor whereas XG19 is excluded from non Syndecan-4 expressing cells such as erythrocytes and non-adherent monocytes (10, 11).

Upon closer observation of peptide uptake (FIG. 4 and FIG. 4A), it was found that while both peptides were taken up by the cells, XG19 was only visualised in the cytoplasm (grey area in the FITC panel of XG19, FIG. 4A) while TAT-Gap19 was visualised in the cytoplasm (grey area in the FITC panel of TAT-Gap19, FIG. 4A) as well as the nucleus (white spots in the FITC panel of TAT-Gap19, FIG. 4A) which was not seen with XG19 treatment. Therefore, while the uptake of TAT-Gap19 was greater than XG19, transport to the nucleus could have undesired effects on cell function and viability in the long term. TAT has previously been used for the transport of other peptides and molecules to the cell nucleus (12, 13); however, delivery of Gap19 to the nucleus could result in reduced efficacy as less peptide is delivered to its site of action. Transport to the cell nucleus could also be potentially toxic.

Example 3

XG19 Uptake into ARPE-19 Cells does not Result in Cytotoxicity Increasing concentrations of XG19 (5, 10 or 20 µM) were applied to ARPE-19 cells for either one hour or twenty-four hours before conducting an MTT cytotoxicity assay. Untreated cells were used as a positive viability control. This was to evaluate the toxicity of XG19 in vitro at both short and long durations. As seen in FIG. 5, XG19 treated cells showed no significant difference in viability when compared to untreated cells at both one and twenty-four hour time points. This showed that the initial uptake process of XG19 into the cell is not toxic. Furthermore once inside the cells XG19 remains non-toxic even at twenty-four hours. This showed that application of XG19 is non-toxic as uptake or storage of the peptide inside cells did not result in cellular toxicity. This is consistent with previous literature regarding toxicity (10, 11).

Example 4

XG19 Inhibits Cx43 Hemichannel Mediated Eth-D1 Dye Uptake

Hemichannel opening can be stimulated in vitro (14), and the entry of small molecules such as ethidium homodimer (EthD-1) dye can therefore be used to observe hemichannel function. The ability of XG19 to inhibit hemichannel opening post cellular uptake, was observed using the EthD-1 uptake assay (FIG. 6). The FITC labelled XG19 used in the cellular uptake experiments was also tested to observe whether the FITC label would interfere with the peptide function.

Cells exposed to the low calcium solution resulted in increased uptake of EthD-1 as low calcium stimulated the opening of hemichannels permitting the entry of the dye into the cell (top left panel of FIG. 6). The EthD-1 dye only has a light fluorescence when in the cytoplasm at low concentrations becoming hyper-fluorescent at higher concentrations as it binds to the cell nucleus.

High calcium solution closed Cx43 hemichannels and therefore inhibited EthD-1 dye uptake (top right panel of FIG. 6). Both XG19 and FITC-XG19 were able to inhibit EthD-1 dye uptake as the fluorescence observed was similar to the high calcium control (bottom panels respectively of FIG. 6). Therefore both XG19 and FITC-XG19 were in a biologically available form post cellular uptake and were able to function as hemichannel blockers. Furthermore the FITC label did not interfere with XG19 function.

Hemichannel inhibition was quantified and plotted on a graph (FIG. 6, right) by measuring the mean EthD-1 fluorescence intensity in four areas per treatment (n=4; mean±SD). One-way ANOVA post hoc comparisons using the Dunnett's multiple comparisons test indicated that high calcium (**p<0.0001), XG19 and FITC-XG19 (*p<0.001) all resulted in significant reduction of the mean fluorescence intensity compared to low calcium treatment, therefore inhibiting hemichannel function.

This confirmed that XG19 functions as a Cx43 hemichannel blocker with the Gap19 component of the peptide being in a bioavailable form post LCLRPV (SEQ ID NO: 2) mediated uptake. Furthermore the identification of retained XG19 functionality after FITC coupling has the potential for this peptide to be used in future in vitro or in vivo assays where visualization of the peptide may be required.

Previous experiments observing ethidium bromide uptake in a similar assay have shown that up to 172 µM of Gap19 had no effect on Cx43 hemichannel inhibition with efficacy only improved when the concentration was increased to 344-688 µM of Gap19 (6). We have shown that even at 5 µM XG19 can be efficacious in this assay due to the increased uptake efficiency of this fusion peptide.

Example 5

XG19 Inhibits Cx43 Hemichannel Mediated ATP Release

During injury open Cx43 hemichannels permit the release of small molecules such as ATP into the extracellular environment providing signals to stimulate the production of inflammatory factors therefore perpetuating the inflammatory condition (15, 16). In vitro measurements of ATP release can be used to assess Cx43 hemichannel opening (17). The ability of XG19 to inhibit ATP release by inhibiting Cx43 hemichannel opening was assessed using the ATP release assay and compared to a known Cx43 hemichannel blocker Peptide 5 (Pep5) as well as the non-specific hemichannel and gap junction blocker carbenoxolone (CBX). Peptide 5 targets extracellular domains of Cx43.

ARPE-19 cells treated with the low calcium solution resulted in a time dependent ATP release measured as luminescence (FIG. 7). Statistical analysis by two-way ANOVA and post hoc comparisons using Dunnett's multiple comparisons test revealed that 25 min treatment with XG19 reduce ATP release, but not significantly compared to the low calcium control whereas treatment with PepS (*p<0.001) and CBX (**p<0.0001) did.

After 30 min of incubation with XG19 (*p<0.05), PepS and CBX (**p<0.0001) all treatments reduced ATP release compared to low calcium. At 35 and 40 min all treatments significantly reduced (**p<0.0001) ATP release compared to the low calcium control. ATP release from PepS and XG19 treated groups, while lower than the low calcium group, were both greater than CBX. This is likely due to the specific blocking nature of PepS and XG19 only blocking Cx43 hemichannels whereas CBX non-specifically blocks multiple types of channels resulting in lower ATP release. PepS has been shown to inhibit Cx43 hemichannel function in multiple assays improving cell survival (18, 19, 20). Therefore, the function of PepS in this assay validates XG19 as a Cx43 hemichannel blocker and further confirmed that Gap19 component of XG19 is in a bioavailable form post LCLRPV (SEQ ID NO: 2) mediated uptake. Furthermore the similar effect achieved with XG19 compared to PepS at 20 times less the concentration further adds to the XG19 potential as a therapeutic.

Example 6

XG19 Function is Maintained 24 Hours Post Uptake

Hemichannel function was assessed by measuring ATP release from cells, one hour and twenty-four hours post XG19 uptake. This was to observe XG19 function at extended time points post-uptake. As seen in FIG. 8, XG19 inhibition of Cx43 hemichannels resulted in a significant reduction in ATP release compared to untreated cells at both 1 and 24 h time points. Statistical analysis was carried out by two-way ANOVA and post hoc comparisons using Sidak's multiple comparisons test. Significance was in comparison to the untreated control at each time point ($p^{}<0.01$, $p^{*}<0.001$, $p^{****}<0.0001$). This showed that XG19 was bioavailable and functional, 24 h post uptake. This suggested that XG19 was stable inside cells for up to 24 h and exhibited functional block of ATP release during injury. Therefore XG19 is functional both immediately and 24 h post uptake.

Example 7

XG19 does not Inhibit Gap Junction Function

Intercellular communication via gap junctions is essential for physiological communication and long term block of gap junction communication could be detrimental to the cell (21). Gap junction function can be assessed in a Lucifer Yellow (LY) dye scrape/load assay (22). Cells that were left unscraped (FIG. 9, top left panel) did not take up the LY dye whereas when the monolayer was scraped (FIG. 9, top right panel) the cells at the site of the scrape allowed the LY dye into the cell, which was then passed onto neighbouring cells via open gap junctions.

Cells treated with the non-specific hemichannel and gap junction blocker CBX (FIG. 9, bottom left panel) took up LY into cells immediately adjacent to the scrape; however, the dye was not further transported to any neighbouring cells due to blocked gap junctions.

Cells treated with 5 µM XG19 resulted in dye uptake at the site of the scrape which was transferred to neighbouring cells via gap junctions (FIG. 9, bottom right panel) similar to the untreated control. This suggested that while XG19 blocks hemichannels, it maintains gap junction function which is required to maintain normal physiological cell-to-cell communication. Previous experiments have shown the ability of Gap19 to maintain gap junction function post uptake (6). The ability of XG19 to maintain gap junction function shows that LCLRPV (SEQ ID NO: 2) does not interfere with Gap19 maintenance of gap junction function post XG19 uptake.

Example 8

Hyperglycaemic and Inflamed Cells Increase Syndecan-4 Expression Syndecan-4 expression was observed in normal and hyperglycaemic and inflamed ARPE-19 cells over time (FIG. 10). Syndecan-4 expression was relatively unchanged in normal media over time whereas cells exposed to hyperglycaemia and inflammation solution showed an increased Syndecan-4 expression from 1 to 3 h with a slight decline at 6 and 24 h. The Syndecan-4 expression of cells in hyperglycaemia and inflammation solution was greater than cells in normal media at every time point as shown by the increased fluorescence (white area in the AF488 panel of FIG. 10). Syndecan-4 expression was assessed by measuring mean fluorescence intensity of FITC in four areas for each treatment (n=3) in cells exposed to media or hyperglycaemia and inflammation solution for 1, 3, 6 or 24 h and plotted on a graph (bottom FIG. 10). Two-way ANOVA and post hoc comparisons using Sidak's test revealed that Syndecan-4 expression was significantly increased in hyperglycaemia and inflammation solution at, 3 h (**$p<0.0001$), 6 h ($p<0.01$) and 24 h (***$p<0.001$) compared to normal media, while there was no significant increase at 1 h. This indicated that ARPE-19 cells upregulate Syndecan-4 expression in response to hyperglycaemia and inflammation. Since Syndecan-4 is the target ligand used by XG19 for cellular uptake, an increased Syndecan-4 expression in hyperglycaemic and inflamed cells could allow for more targeted delivery of the peptide specifically to diseased cells.

Example 9

XG19 Uptake is Increased in Hyperglycaemic and Inflamed Cells

To observe if cell uptake of XG19 was altered in the hyperglycaemic and inflamed cells; XG19 was applied to normal and hyperglycaemic and inflamed cells and cellular uptake was compared to Gap19 (FIG. 11). XG19 uptake was observed in media as well as in hyperglycaemia and inflammation solution. Gap19 uptake was undetectable in either condition (absence of white area in FITC panel, FIG. 11). The uptake of XG19 in hyperglycaemia and inflammation solution was greater than in normal media as indicated by the greater fluorescence in hyperglycaemia and inflammation solution (white area in FITC panel, FIG. 11). This suggested that XG19 uptake was increased in hyperglycaemic and inflamed cells, which the inventors postulate was due to the over-expression of Syndecan-4 in APRE-19 cells in response to hyperglycaemia and inflammation. Furthermore, the increased uptake of Gap19 in hyperglycaemic and inflamed cells was LCLRPV-dependent (SEQ ID NO: 2) as native Gap19 uptake was not increased in these cells. The inventors finding of increased uptake of XG19 by hyperglycaemic and inflamed cells and their discovery of Syndecan-4 expression in the RPE and choroid makes XG19 a candidate therapeutic for AMD as it has the potential to be more readily taken up by cells most affected by the disease and therefore could result in improved therapeutic efficacy.

Example 10

Hypoxic Cells Increase Syndecan-4 Expression

In AMD, retinal pigment epithelium cells become hypoxic due to localised sites of ischemia. Hypoxia can alter the expression of cell surface proteins such as Syndecan-4 (23). Syndecan-4 expression was observed in hypoxic and normal cells over time (FIG. 12). Syndecan-4 expression was relatively unchanged in normal media over time whereas cells exposed to hypoxic solution showed an increased Syndecan-4 expression from 1 to 3 and from 3 to 6 h with a slight decline at 24 h likely due to some cell death caused by over exposure to the hypoxic solution, therefore reducing the cell density and Syndecan-4 expression. The Syndecan-4 expression of cells in hypoxic solution was greater than cells in normal media at every time point as shown by the increased fluorescence (white area in the AF488 panel of FIG. 12). Syndecan-4 expression was assessed by measuring mean fluorescence intensity of FITC in four areas for each treatment (n=4) in cells exposed to media or hypoxic solution for 1, 3, 6 or 24 h and plotted on a graph (bottom FIG. 12).

Two-way ANOVA and post hoc comparisons using Sidak's test revealed that Syndecan-4 expression significantly increased in hypoxic solution at 1 h ($p<0.01$), 3 h (*$p<0.001$), 6 h (****$p<0.0001$) and 24 h (*$p<0.05$) compared to normal media. This indicates that ARPE-19 cells up regulate Syndecan-4 expression in response to hypoxia. Since Syndecan-4 is the target ligand used by XG19 for cellular uptake, an increased Syndecan-4 expression in hypoxic cells could allow for more targeted delivery of the peptide specifically to diseased cells.

Example 11

XG19 Uptake is Increased in Hypoxic Cells

To observe if cell uptake of XG19 was altered in the hypoxic condition; XG19 was applied to normal and hypoxic cells and cellular uptake was compared to Gap19 (FIG. 13). XG19 uptake was observed in both media as well as in hypoxic solution while Gap19 uptake was undetectable in either condition (absence of white area in FITC panel, FIG. 13). The uptake of XG19 in hypoxic solution was greater than in normal media as indicated by the greater fluorescence in hypoxic solution (white area in FITC panel, FIG. 13). This suggests that XG19 uptake is improved in hypoxic cells, which the inventors postulate may be due to the over-expression of Syndecan-4 in APRE-19 cells in response to hypoxia. Furthermore, the increased uptake of Gap19 in hypoxic cells was LCLRPV (SEQ ID NO: 2) dependent as native Gap19 uptake was not increased in hypoxic cells. The inventors finding of increased uptake of XG19 by hypoxic cells and their discovery of Syndecan-4 expression in the RPE and choroid makes XG19 a candidate therapeutic for AMD as it has the potential to be more readily taken up by cells most affected by the disease and therefore could result in improved therapeutic efficacy.

Example 12

XG19 Maintains Cell Viability During Hypoxic Injury

Cell viability was assessed in hypoxic cells by applying HAIR solution to untreated and XG19 treated cells and compared to cells in normal media in a MTT assay. This was to observe if XG19 could prevent the reduction in cell viability which occurs during hypoxia. As seen in FIG. 14, the viability of hypoxic cells was significantly reduced compared to cells in normal media which suggested that hypoxic cells were experiencing injury and dying.

There was no significant difference seen in the XG19 treated cells compared to the untreated cells in normal media. This showed that XG19 treated cells prevented cell death during hypoxia mediated injury. One-way ANOVA was carried out with post hoc Dunnett's test and significance was represented as a difference from the untreated cells in normal media control (***$p<0.001$). Therefore XG19 increased cell survival and prevented the effects of injury during hypoxia.

Example 13

XG19 Inhibits Cx43 Hemichannel Mediated ATP Release During Hypoxia

Hypoxia was induced by applying HAIR solution to untreated or XG19 treated cells and ATP release was measured. As seen in FIG. 15, XG19 treated cells had a significant reduction in ATP release compared to untreated cells in HAIR solution. One-way ANOVA was carried out with post hoc Dunnett's test and significance was represented as a difference from the untreated cells in HAIR solution (*$p<0.001$, **$p<0.0001$). This showed that hypoxia resulted in ATP release via Cx43 hemichannels. XG19 was able to inhibit hemichannel opening during this hypoxic injury therefore resulting in reduced ATP release. Therefore XG19 was able to reduce ATP release during hypoxic injury which promotes cell survival during injury.

Example 14

XG19 Reduces Lesion Area in a Laser Induced Choroidal Neovascularisation (CNV) Mouse Model Laser induced lesions were created in C57BL6 mice on day 0 as previously described in methods. Fundus images were acquired on Day 1 and Day 7 and area measurements of the lesions were made using ImageJ software. As seen in FIG. 16, there were no observed differences in lesion area between the Saline (n=8 eyes), low dose XG19 (n=8 eyes) or high dose XG19 (n=7 eyes) groups on Day 1. On Day 7 there was no change in lesion area in the Saline group compared to Day 1, while both the XG19 treated groups were smaller on Day 7 compared to Day 1. Furthermore High dose XG19 treated mice resulted in the smallest lesion area measurements while Saline treated mice resulted in the largest lesion area measurements. These results suggest that XG19 is having a dose dependent effect on the reduction of the lesion area thus reducing the spread of injury.

Example 15

XG19 Treated Mice Result in Significantly Smaller Lesion Volume in a Laser Induced Choroidal Neovascularisation (CNV) Mouse Model The retinal layers were visualised in mice from the CNV model described in Example 14 by OCT. OCT images acquired on Day 7 were used to measure ellipsoid volume of the CNV lesions using ImageJ software. As seen in FIG. 17, Saline treated mice (n=8 eyes) resulted in the largest volume measurements while mice treated with Low dose XG19 (n=8 eyes) or High dose XG19 (n=7 eyes) resulted in significantly smaller volume measurements as determined by one-way ANOVA carried out with post hoc Dunnett's test and significance represented as a difference from the Saline group (**$p<0.01$, mean+SD). This showed that XG19 treatment was able to significantly reduce CNV lesion volume compared to saline treatment. Furthermore there was no significant difference between the low dose and high dose XG19 groups, which suggested that the effective therapeutic concentration can be achieved with the lower XG19 dose. Ellipsoid volume measurement has been shown to be comparable to classic ex vivo techniques of choroidal flatmount to assess CNV lesions (35). Previous literature using choroidal flatmounts have shown CNV lesions growth is due to blood vessel growth, subretinal fluid accumulation and apoptosis of the tissue (35-38). Therefore the reduced CNV volume seen in our results was indicative of tissue healing and normalisation of the RPE choroid complex.

Example 16

Syndecan-4 and GFAP Expression is Reduced in XG19 Treated Mice in a Laser Induced Choroidal Neovascularisation (CNV) Mouse Model The mice from the CNV model described in Examples 14 and 15 were culled on day 8 and the eyes were enucleated, sectioned and labelled for Syndecan-4 and GFAP expression. Saline injected mice showed elevated Syndecan-4 and GFAP expression compared to XG19 injected mice (FIG. 18). Our in vitro data has shown an increase in Syndecan-4 during inflammation and hypoxia (Examples 8 and 10) while ex vivo DR tissue also showed increased Syndecan-4 in diseased tissue (Example 18). GFAP expression has been shown to be elevated in CNV mouse models due to inflammation and ischaemia at the site of the lesion (38). This showed that XG19 has reduced inflammation and ischaemia in the mouse retina and therefore XG19 promotes healing in this mouse model of CNV.

Example 17

Syndecan-4 Expression in Human Retinal Sections

XG19 has a high affinity for the cell surface protein Syndecan-4 facilitating cellular uptake. Human retinal donor tissues were sectioned and labelled for Syndecan-4 expression (FIG. 19). The unlabelled sections used as an antibody control showed some background fluorescence in the RPE layer due to autofluorescent pigment present in these cells (AF488 panel, FIG. 19). This was also seen in the sections labelled for Syndecan-4 (white area of AF488 panel of Syndecan-4 labelled sections, FIG. 10); however, the labelling was more prominent covering the entirety of the RPE suggesting true Syndecan-4 labelling. Furthermore, Syndecan-4 labelling was also observed in the choroid, in particular on endothelial cells around blood vessels (white area of AF488 panel of Syndecan-4 labelled sections, FIG. 19). The RPE and choroid are most affected in AMD and therefore the preferred target sites for XG19. The discovery of expression of Syndecan-4 in these tissues means that XG19 will be targeted specifically to these cells potentially improving therapeutic efficacy and reducing any potential side effects.

Example 18

Syndecan-4 and GFAP Expression is Increased in Human Diabetic Retinopathy Tissue Human donor tissue sections form patients with diabetic retinopathy (DR) and without (normal) were labelled for Syndecan-4, GFAP and nuclei were stained with DAPI. Sections were taken from both the macular and paramacular region (FIGS. 20 and 21 respectively). In both the paramacular and macular sections there was increased Syndecan-4 labelling in the DR tissue compared to the normal tissue. There was also increased labelling in the blood vessels and in parts of the tissue which showed dysregulation due to blood vessel growth. Blood vessel growth in DR is poorly regulated and results in the formation of leaky blood vessels making the tissue ischaemic and hypoxic. The increased Syndecan-4 expression seen at these sites is indicative of hypoxia in this area. GFAP expression was also increased in DR tissue in both macular and paramacular regions. The combination of GFAP and Syndecan-4 expression in the DR tissue suggests that this tissue is experiencing inflammation and is injured. Syndecan-4 labelling was also seen in the ILM (FIG. 20) which is of interest as the ILM can often act as a barrier for drug delivery. It has been proposed that activated Müller cells at this site have the potential to improve drug delivery by transporting drug molecules from the ILM to the outer retina (32). Uptake at the ILM will provide an advantage for drug delivery. Therefore, the upregulation of Syndecan-4 in this tissue can be targeted by XG19 in order to reduce inflammation in this area.

Example 19

Syndecan-4 expression is increased in rat models of acute pancreatitis and sepsis Lung tissues from rat models of acute pancreatitis (AP) and sepsis were labelled for syndecan-4 and compared to Sham animals. Both disease models result in global inflammation. The sepsis and AP tissues (FIGS. 22 and 23 respectively) had elevated Syndecan-4 expression compared to the Sham animals. There was increased Syndecan-4 expression in the bronchioles and the alveoli suggesting that the diseases affect the airways. AP has been known to cause pulmonary complications and hypoxia (27) while severe sepsis can result secondary complications such as acute respiratory distress syndrome (ARDS) (28). The upregulation of Syndecan-4 in these tissues provides a target for preferential uptake during these disease states. Therefore constructs of the invention can be used to deliver therapeutics to address secondary respiratory complications during sepsis and AP.

Example 20

Syndecan-4 Expression is Elevated in Chronic Rhinosinusitis Tissue

Chronic rhinosinusitis (CRS) is an inflammatory condition which affects the sinus. Blockages in the sinus caused by inflammation, allergy, or swelling can result in this tissue becoming hypoxic and worsening the condition (26). The inventors have observed Syndecan-4 elevation in ocular tissues under these conditions, therefore normal sinus and CRS human tissue sections were labelled for Syndecan-4 expression. As seen in FIG. 24, normal sinus tissue showed modest Syndecan-4 labelling with slight elevation around the glands. Syndecan-4 labelling in CRS tissue showed elevated labelling around the glands and was widely distributed throughout the tissue. The expression of Syndecan-4 was quantified by measuring the mean fluorescence intensity of the imaged areas from three normal and three CRS tissues (n=3). This showed that CRS tissues had elevated Syndecan-4 expression compared to normal sinus tissues. This showed that inflamed or hypoxic tissues outside the eye also have elevated Syndecan-4 expression confirming they are a potential target for drug delivery using constructs of the invention.

Example 21

Syndecan-4 Expression in Mouse Glioma Model

Sections from a mouse model of glioma (tumour) were labelled for Syndecan-4, GFAP nuclei were stained with DAPI (FIG. 25 and FIG. 25A). In FIG. 25 the mouse brain tissue expressed an elevated amount of GFAP due to a large number of activated astrocytes, indicating inflammation in this area. There is increased elevation where the brain tissue meets the tumour and can be clearly seen as the tumour does not express GFAP (FIG. 25). This is because the tumour has completely infiltrated this area of brain tissue, killing any astrocytes in this area and therefore lacking GFAP expression. There is also increased elevation of GFAP surrounding a distinct group of cells arising from an extension of the tumour in the brain tissue. In the Syndecan-4 panel this distinct group of cells has elevated Syndecan-4 expression similar to what is seen at the interface of the tumour and brain tissue and within the main body of the tumour. This suggests that the distinct group of cells with elevated Syndecan-4 in the brain tissue are an extension of the tumour. The elevated GFAP surrounding these cells suggests that the infiltrating tumour cells are injuring the brain tissue and causing inflammation. The elevated Syndecan-4 expression at the tumour edge and at sites of tumour infiltration make tumours an ideal target for uptake of constructs of the invention.

In FIG. 25A we see that in the tumour hemisphere blood vessels show elevated Syndecan-4 and GFAP labelling compared to the adjacent hemisphere. The blood vessel in the adjacent hemisphere had normal elongated nuclei found along the blood vessel whereas the blood vessel in the tumour hemisphere contained many nuclei in close proximity suggesting unregulated proliferation of the blood vessel. This suggested that the blood vessels in the tumour hemisphere were poorly formed. In the tumour hemisphere the blood vessel and the surrounding tissue showed elevated GFAP and Syndecan-4 labelling which showed high inflammation in this area. This also showed that Syndecan-4 is present in the blood brain barrier (BBB) especially during injury and therefore constructs of the invention could deliver therapeutics for brain injury as the constructs will be more readily taken up at these sites.

Example 22

Hypoxic A341 Tumours Express Syndecan-4 Human A431 tumours grown subcutaneously in mouse flank were excised sectioned and labelled for Syndecan-4 and nuclei were stained for DAPI. This tumour model yields hypoxic tumours. As seen in FIG. 26, Syndecan-4 expression was seen throughout the tumour tissue. There were elevated areas of Syndecan-4 in the central regions of the tumours which appeared in distinct cell clusters. Given that this is a tumour hypoxia model it is likely that Syndecan-4 expression at these sites indicates hypoxic regions of the tumour tissue.

Example 23

Hypoxic SKOV3 Tumours Express Syndecan-4

Human SKOV3 tumours grown subcutaneously in nude mouse flank to form xenografts were excised sectioned and labelled for Syndecan-4 and nuclei were stained for DAPI. SKOV3 is a human ovarian carcinoma cell line used frequently in models of oncology drug development. This tumour model yields hypoxic tumours. As seen in FIG. 27, Syndecan-4 expression was seen throughout the tumour tissue at low levels. There were elevated areas of Syndecan-4 in the tumour which appeared either in distinct cell clusters or in areas immediately around the clusters. Given that these tumours are known to be hypoxic it is likely that Syndecan-4 expression at these sites indicates regions of elevated hypoxia in these tumours.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge.

Throughout this specification, unless the context requires otherwise, the words "comprise", "comprising" and the like, are to be construed in an inclusive sense as opposed to an exclusive sense, that is to say, in the sense of "including, but not limited to".

What we claim is:

1. A polypeptide construct comprising:
   (a) a targeting carrier peptide derived from the X-protein of the Hepatitis B virus and
   (b) a peptide capable of interacting with an intracellular domain of connexin43 (Cx43).

2. The polypeptide construct according to claim 1, wherein the targeting carrier peptide:

A) comprises an amino acid sequence selected from the group consisting of:

```
                                                      (SEQ ID NO: 4)
   LCL;

(SEQ ID NO: 5)
   LCLRP;

(SEQ ID NO: 2)
   LCLRPV;

(SEQ ID NO: 6)
   LCLRPVG;

(SEQ ID NO: 7)
   LCLRPVGAE;

(SEQ ID NO: 8)
   LCLRPVGAESR;

(SEQ ID NO: 9)
   LCLRPVGAESRGRPV;
   and (SEQ ID NO: 10)
   LCLRPVGAESRGRPVSGPFG;
   ```
   or B) consists of an amino acid sequence selected from the group consisting of:

```
                                                      (SEQ ID NO: 4)
   LCL;

(SEQ ID NO: 5)
   LCLRP;

(SEQ ID NO: 2)
   LCLRPV;

(SEQ ID NO: 6)
   LCLRPVG;

(SEQ ID NO: 7)
   LCLRPVGAE;

(SEQ ID NO: 8)
   LCLRPVGAESR;
   ```

-continued

LCLRPVGAESRGRPV; (SEQ ID NO: 9)
and

LCLRPVGAESRGRPVSGPFG; (SEQ ID NO: 10)

or

C) consists of an amino acid sequence selected from the group consisting of:

LCLX; (SEQ ID NO: 11)

XLCL; (SEQ ID NO: 12)

XLCLX; (SEQ ID NO: 13)

LCLK; (SEQ ID NO: 14)

LCLH; (SEQ ID NO: 15)

LCLR; (SEQ ID NO: 16)

LCLE; (SEQ ID NO: 17)

LCLN; (SEQ ID NO: 18)

LCLQ; (SEQ ID NO: 19)

VLCLR; (SEQ ID NO: 20)
and

LCLD; (SEQ ID NO: 21)

wherein X is any amino acid.

3. The polypeptide construct for use in a method according to claim 1, wherein the targeting carrier peptide:
A) comprises an amino acid selected from the group consisting of:

XCXR; (SEQ ID NO: 22)

ICIR; (SEQ ID NO: 23)
and

VCVR, (SEQ ID NO: 24)

wherein X is any hydrophobic amino acid; or
B) consists of an amino acid selected from the group consisting of:

XCXR; (SEQ ID NO: 22)

ICIR; (SEQ ID NO: 23)
and

VCVR, (SEQ ID NO: 24)

wherein X is any hydrophobic amino acid.

4. The polypeptide construct according to claim 1, wherein the peptide capable of interacting with an intracellular domain of connexin43 (Cx43) is capable of inhibiting:
A) the interaction of the intracellular C-terminal tail of Cx43 with the intracellular loop of Cx43; and/or
B) Cx43 hemichannel opening.

5. The polypeptide construct according to claim 1, wherein the peptide capable of interacting with an intracellular domain of Cx43:
A) comprises an amino acid sequence selected from the group consisting of:

KQIEIKKFK; (SEQ ID NO: 3)

DGVNVEMHLKQIEIKKFKYGIEEHGK; (SEQ ID NO: 67)

DGANVDMHLKQIEIKKFKYGIEEHGK; (SEQ ID NO: 68)

RPSSRASSRASSRPRPDDLEI; (SEQ ID NO: 69)

RQPKIWFPNRRKPWKKRPRPDDLEI; (SEQ ID NO: 70)

RPRPDDLEI; (SEQ ID NO: 71)
and

SRPRPDDLEI; (SEQ ID NO: 72)

or

B) consists of an amino acid sequence selected from the group consisting of:

KQIEIKKFK; (SEQ ID NO: 3)

DGVNVEMHLKQIEIKKFKYGIEEHGK; (SEQ ID NO: 67)

DGANVDMHLKQIEIKKFKYGIEEHGK; (SEQ ID NO: 68)

RPSSRASSRASSRPRPDDLEI; (SEQ ID NO: 69)

RQPKIWFPNRRKPWKKRPRPDDLEI; (SEQ ID NO: 70)

RPRPDDLEI; (SEQ ID NO: 71)
and

SRPRPDDLEI. (SEQ ID NO: 72)

6. The polypeptide construct according to claim 1, wherein the targeting carrier peptide is connected by a linker to the peptide capable of interacting with an intracellular domain of Cx43; optionally wherein the linker is a glycine linker or a polyglutamine linker.

7. A polypeptide construct comprising:
(a) a targeting carrier peptide derived from the X-protein of the Hepatitis B virus and
(b) a peptide capable of interacting with an intracellular domain of connexin43 (Cx43), wherein the targeting carrier peptide:

A) comprises an amino acid sequence selected from the group consisting of:

```
                        (SEQ ID NO: 22)
XCXR;

(SEQ ID NO: 23)
ICIR;
and (SEQ ID NO: 24)
VCVR,
``` wherein X is any hydrophobic amino acid; or

B) consists of an amino acid sequence selected from the group consisting of:

```
                        (SEQ ID NO: 22)
XCXR;

(SEQ ID NO: 23)
ICIR;
and (SEQ ID NO: 24)
VCVR,
``` wherein X is any hydrophobic amino acid.

8. The polypeptide construct according to claim 7 wherein the peptide capable of interacting with an intracellular domain of connexin43 (Cx43):

A) is capable of inhibiting the interaction of the intracellular C-terminal tail of Cx43 with the intracellular loop of Cx43; and/or B) is capable of inhibiting Cx43 hemichannel opening; and/or C) comprises an amino acid sequence selected from the group consisting of:

```
                        (SEQ ID NO: 3)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID NO: 69)
RPSSRASSRASSRPRPDDLEI;

(SEQ ID NO: 70)
RQPKIWFPNRRKPWKKRPRPDDLEI;

(SEQ ID NO: 71)
RPRPDDLEI;
and (SEQ ID NO: 72)
SRPRPDDLEI;
``` and/or

D) consists of an amino acid sequence selected from the group consisting of:

```
                        (SEQ ID NO: 3)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID NO: 69)
RPSSRASSRASSRPRPDDLEI;

(SEQ ID NO: 70)
RQPKIWFPNRRKPWKKRPRPDDLEI;

(SEQ ID NO: 71)
RPRPDDLEI;
and (SEQ ID NO: 72)
SRPRPDDLEI.
```

9. The construct according to claim 7, wherein the targeting carrier peptide is connected by a linker to the peptide capable of interacting with an intracellular domain of Cx43; optionally, wherein the linker is a glycine linker or a polyglutamine linker.

10. A protein construct comprising:

(a) a targeting carrier peptide derived from the X-protein of the Hepatitis B virus, wherein the targeting carrier peptide comprises LCL (SEQ ID NO: 4), and (b) a peptide capable of interacting with an intracellular domain of connexin43 (Cx43).

11. A The polypeptide construct according to claim 10, wherein the targeting carrier peptide:

A) comprises an amino acid sequence selected from the group consisting of:

```
                        (SEQ ID NO: 5)
LCLRP;

(SEQ ID NO: 2)
LCLRPV;

(SEQ ID NO: 6)
LCLRPVG;

(SEQ ID NO: 7)
LCLRPVGAE;

(SEQ ID NO: 8)
LCLRPVGAESR;

(SEQ ID NO: 9)
LCLRPVGAESRGRPV;
and (SEQ ID NO: 10)
LCLRPVGAESRGRPVSGPFG;
``` or

B) consists of an amino acid sequence selected from the group consisting of:

```
                        (SEQ ID NO: 4)
LCL;

(SEQ ID NO: 5)
LCLRP;

(SEQ ID NO: 2)
LCLRPV;

(SEQ ID NO: 6)
LCLRPVG;

(SEQ ID NO: 7)
LCLRPVGAE;
```

-continued

```
                             (SEQ ID NO: 8)
LCLRPVGAESR;

(SEQ ID NO: 9)
LCLRPVGAESRGRPV;
and (SEQ ID NO: 10)
LCLRPVGAESRGRPVSGPFG;
``` or

C) comprises an amino acid sequence selected from the group consisting of:

```
                             (SEQ ID NO: 11)
LCLX;

(SEQ ID NO: 12)
XLCL;

(SEQ ID NO: 13)
XLCLX;

(SEQ ID NO: 14)
LCLK;

(SEQ ID NO: 15)
LCLH;

(SEQ ID NO: 16)
LCLR;

(SEQ ID NO: 17)
LCLE;

(SEQ ID NO: 18)
LCLN;

(SEQ ID NO: 19)
LCLQ;

(SEQ ID NO: 20)
VLCLR;
and (SEQ ID NO: 21)
LCLD;
``` wherein X is any amino acid; or

D) consists of an amino acid sequence selected from the group consisting of:

```
                             (SEQ ID NO: 11)
LCLX;

(SEQ ID NO: 12)
XLCL;

(SEQ ID NO: 13)
XLCLX;

(SEQ ID NO: 14)
LCLK;

(SEQ ID NO: 15)
LCLH;

(SEQ ID NO: 16)
LCLR;

(SEQ ID NO: 17)
LCLE;

(SEQ ID NO: 18)
LCLN;
```

```
                             (SEQ ID NO: 19)
LCLQ;

(SEQ ID NO: 20)
VLCLR;
and (SEQ ID NO: 21)
LCLD;
``` wherein X is any amino acid.

12. The polypeptide construct according to claim 10, wherein the peptide capable of interacting with an intracellular domain of connexin43 (Cx43):

A) is capable of inhibiting the interaction of the intracellular C-terminal tail of Cx43 with the intracellular loop of Cx43: and/or B) is capable of inhibiting Cx43 hemichannel opening; and/or C) comprises an amino acid sequence selected from the group consisting of:

```
                             (SEQ ID NO: 3)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID N: 69)
RPSSRASSRASSRPRPDDLEI;

(SEQ ID NO: 70)
RQPKIWFPNRRKPWKKRPRPDDLEI;

(SEQ ID NO: 71)
RPRPDDLEI;
and (SEQ ID NO: 72)
SRPRPDDLEI;
``` and/or

D) consists of an amino acid sequence selected from the group consisting of:

```
                             (SEQ ID NO: 3)
KQIEIKKFK;

(SEQ ID NO: 67)
DGVNVEMHLKQIEIKKFKYGIEEHGK;

(SEQ ID NO: 68)
DGANVDMHLKQIEIKKFKYGIEEHGK;

(SEQ ID NO: 69)
RPSSRASSRASSRPRPDDLEI;

(SEQ ID NO: 70)
RQPKIWFPNRRKPWKKRPRPDDLEI;

(SEQ ID NO: 71)
RPRPDDLEI;
and (SEQ ID NO: 72)
SRPRPDDLEI.
```

13. The polypeptide construct according to claim 12, wherein the targeting carrier peptide:

A) comprises an amino acid sequence selected from the group consisting of:

LCLRP; (SEQ ID NO: 5)

LCLRPV; (SEQ ID NO: 2)

LCLRPVG; (SEQ ID NO: 6)

LCLRPVGAE; (SEQ ID NO: 7)

LCLRPVGAESR; (SEQ ID NO: 8)

LCLRPVGAESRGRPV; (SEQ ID NO: 9)
and

LCLRPVGAESRGRPVSGPFG; (SEQ ID NO: 10)

or

B) consists of an amino acid sequence selected from the group consisting of:

LCLRP; (SEQ ID NO: 5)

LCLRPV; (SEQ ID NO: 2)

LCLRPVG; (SEQ ID NO: 6)

LCLRPVGAE; (SEQ ID NO: 7)

LCLRPVGAESR; (SEQ ID NO: 8)

LCLRPVGAESRGRPV; (SEQ ID NO: 9)
and

LCLRPVGAESRGRPVSGPFG; (SEQ ID NO: 10)

or

C) comprises an amino acid sequence selected from the group consisting of:

LCLX; (SEQ ID NO: 11)

XLCL; (SEQ ID NO: 12)

XLCLX; (SEQ ID NO: 13)

LCLK; (SEQ ID NO: 14)

LCLH; (SEQ ID NO: 15)

LCLR; (SEQ ID NO: 16)

LCLE; (SEQ ID NO: 17)

LCLN; (SEQ ID NO: 18)

LCLQ; (SEQ ID NO: 19)

VLCLR; (SEQ ID NO: 20)
and

LCLD; (SEQ ID NO: 21)

wherein X is any amino acid; or

D) consists of an amino acid sequence selected from the group consisting of:

LCLX; (SEQ ID NO: 11)

XLCL; (SEQ ID NO: 12)

XLCLX; (SEQ ID NO: 13)

LCLK; (SEQ ID NO: 14)

LCLH; (SEQ ID NO: 15)

LCLR; (SEQ ID NO: 16)

LCLE; (SEQ ID NO: 17)

LCLN; (SEQ ID NO: 18)

LCLQ; (SEQ ID NO: 19)

VLCLR; (SEQ ID NO: 20)
and

LCLD; (SEQ ID NO: 21)

wherein X is any amino acid.

14. The polypeptide construct according to claim 10, wherein the targeting carrier peptide is connected by a linker to the peptide capable of interacting with an intracellular domain of Cx43; optionally wherein the linker is a glycine linker or a polyglutamine linker.

15. A polypeptide construct comprising the amino acid sequence of SEQ ID NO: 1, wherein:
(i) all amino acids of SEQ ID NO: 1 are L-amino acids; or
(ii) all amino acids of SEQ ID NO: 1 comprise L-amino acids, D-amino acids, or a mixture thereof.

16. A nucleic acid molecule encoding the polypeptide construct of claim 1.

17. A vector comprising the nucleic acid molecule of claim 16.

18. A nucleic acid molecule encoding the protein construct of claim 7.

19. A vector comprising the nucleic acid molecule of claim 18.

20. A nucleic acid molecule encoding the polypeptide construct of claim 10.

21. A vector comprising the nucleic acid molecule of claim 20.

22. A nucleic acid encoding the polypeptide construct of according to claim 15.

23. A vector comprising the nucleic acid molecule of claim 22.

24. A method of treating a subject having a disease or disorder of the eye, comprising administering to the subject a polypeptide construct according to claim 1.

25. A method according to claim 24, wherein the polypeptide construct is IchpvKQIEIKKFK (SEQ ID NO:1), wherein the lowercase letters represent a D-isomer.

26. The method according to claim 24, wherein the disease or disorder of the eye is selected from the group consisting of: AMD (including wet and/or dry AMD), diabetic retinopathy, glaucoma, retinal vein and/or branch occlusion, retinal artery occlusion, retinal stroke, macular oedema, uveitis, blepharitis, severe dry eye syndrome, diabetic peripheral neuropathy, and optic neuritis.

27. A method for targeting delivery of a peptide capable of interacting with an intracellular domain of connexin43 to hypoxic cells in a subject, comprising administering to the subject the polypeptide construct of claim 1.

28. The method according to claim 27, wherein the subject has a disease or disorder associated with hypoxia.

29. The method according to claim 28, wherein the disease or disorder is cancer, stroke or cardiovascular disease.

30. The method according to claim 29, wherein the cardiovascular disease is selected from the group consisting of cardiac ischemia, pericarditis, myocardial infarction, and ischemic valve disease.

* * * * *

UNITED STATES PATENT AND TRADEMARK OFFICE
CERTIFICATE OF CORRECTION

PATENT NO. : 11,466,069 B2
APPLICATION NO. : 16/608761
DATED : October 11, 2022
INVENTOR(S) : Colin Richard Green et al.

It is certified that error appears in the above-identified patent and that said Letters Patent is hereby corrected as shown below:

In the Specification

Column 16, Line 18, delete "lchpv" and insert --lclrpv--

Column 62, Line 64, delete "clrpv" and insert --lclrpv--

Signed and Sealed this
Twenty-second Day of November, 2022

Katherine Kelly Vidal
*Director of the United States Patent and Trademark Office*

SEQUENCE LISTING

```
<160> NUMBER OF SEQ ID NOS: 81

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-amino acid

<400> SEQUENCE: 1

Leu Cys Leu Arg Pro Val Gly Gly Lys Gln Ile Glu Ile Lys Lys Phe
1               5                   10                  15

Lys

<210> SEQ ID NO 2
<211> LENGTH: 6
<212> TYPE: PRT
<213> ORGANISM: Hepatitis B virus
```

```
<400> SEQUENCE: 2

Leu Cys Leu Arg Pro Val
1               5

<210> SEQ ID NO 3
<211> LENGTH: 9
<212> TYPE: PRT
<213> ORGANISM: Homo sapiens

<400> SEQUENCE: 3

Lys Gln Ile Glu Ile Lys Lys Phe Lys
1               5

<210> SEQ ID NO 4
<211> LENGTH: 3
<212> TYPE: PRT
<213> ORGANISM: Hepatitis B virus

<400> SEQUENCE: 4

Leu Cys Leu
1

<210> SEQ ID NO 5
<211> LENGTH: 5
<212> TYPE: PRT
<213> ORGANISM: Hepatitis B virus

<400> SEQUENCE: 5

Leu Cys Leu Arg Pro
1               5

<210> SEQ ID NO 6
<211> LENGTH: 7
<212> TYPE: PRT
<213> ORGANISM: Hepatitis B virus

<400> SEQUENCE: 6

Leu Cys Leu Arg Pro Val Gly
1               5

<210> SEQ ID NO 7
<211> LENGTH: 9
<212> TYPE: PRT
<213> ORGANISM: Hepatitis B virus

<400> SEQUENCE: 7

Leu Cys Leu Arg Pro Val Gly Ala Glu
1               5

<210> SEQ ID NO 8
<211> LENGTH: 11
<212> TYPE: PRT
<213> ORGANISM: Hepatitis B virus

<400> SEQUENCE: 8

Leu Cys Leu Arg Pro Val Gly Ala Glu Ser Arg
1               5                   10

<210> SEQ ID NO 9
<211> LENGTH: 15
<212> TYPE: PRT
<213> ORGANISM: Hepatitis B virus
```

-continued

```
<400> SEQUENCE: 9

Leu Cys Leu Arg Pro Val Gly Ala Glu Ser Arg Gly Arg Pro Val
1               5                   10                  15

<210> SEQ ID NO 10
<211> LENGTH: 20
<212> TYPE: PRT
<213> ORGANISM: Hepatitis B virus

<400> SEQUENCE: 10

Leu Cys Leu Arg Pro Val Gly Ala Glu Ser Arg Gly Arg Pro Val Ser
1               5                   10                  15

Gly Pro Phe Gly
            20

<210> SEQ ID NO 11
<211> LENGTH: 4
<212> TYPE: PRT
<213> ORGANISM: Hepatitis B virus
<220> FEATURE:
<221> NAME/KEY: MOD_RES
<222> LOCATION: (4)..(4)
<223> OTHER INFORMATION: Any naturally occurring amino acid

<400> SEQUENCE: 11

Leu Cys Leu Xaa
1

<210> SEQ ID NO 12
<211> LENGTH: 4
<212> TYPE: PRT
<213> ORGANISM: Hepatitis B virus
<220> FEATURE:
<221> NAME/KEY: MOD_RES
<222> LOCATION: (1)..(1)
<223> OTHER INFORMATION: Any naturally occurring amino acid

<400> SEQUENCE: 12

Xaa Leu Cys Leu
1

<210> SEQ ID NO 13
<211> LENGTH: 5
<212> TYPE: PRT
<213> ORGANISM: Hepatitis B virus
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (5)..(5)
<223> OTHER INFORMATION: Any naturally occurring amino acid

<400> SEQUENCE: 13

Xaa Leu Cys Leu Xaa
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 14

Leu Cys Leu Lys
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Cys Leu His
1

<210> SEQ ID NO 16
<211> LENGTH: 4
<212> TYPE: PRT
<213> ORGANISM: Hepatitis B virus

<400> SEQUENCE: 16

Leu Cys Leu Arg
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Cys Leu Glu
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Cys Leu Asn
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Cys Leu Gln
1

<210> SEQ ID NO 20
<211> LENGTH: 5
<212> TYPE: PRT
<213> ORGANISM: Hepatitis B virus
```

```
<400> SEQUENCE: 20

Val Leu Cys Leu Arg
1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Cys Leu Asp
1

<210> SEQ ID NO 22
<211> LENGTH: 4
<212> TYPE: PRT
<213> ORGANISM: Hepatitis B virus
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
<222> LOCATION: (3)..(3)
<223> OTHER INFORMATION: Any hydrophobic amino acid

<400> SEQUENCE: 22

Xaa Cys Xaa Arg
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Cys Ile Arg
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Cys Val Arg
1

<210> SEQ ID NO 25
<211> LENGTH: 35
<212> TYPE: PRT
<213> ORGANISM: Hepatitis B virus
```

```
<400> SEQUENCE: 25

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
            20                  25                  30

Pro Phe Gly
        35

<210> SEQ ID NO 26
<211> LENGTH: 35
<212> TYPE: PRT
<213> ORGANISM: Hepatitis B virus

<400> SEQUENCE: 26

Met Ala Ala Arg Met Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
            20                  25                  30

Pro Phe Gly
        35

<210> SEQ ID NO 27
<211> LENGTH: 35
<212> TYPE: PRT
<213> ORGANISM: Hepatitis B virus

<400> SEQUENCE: 27

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Phe Gly
        35

<210> SEQ ID NO 28
<211> LENGTH: 35
<212> TYPE: PRT
<213> ORGANISM: Hepatitis B virus

<400> SEQUENCE: 28

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Val Ser Arg
            20                  25                  30

Pro Phe Gly
        35

<210> SEQ ID NO 29
<211> LENGTH: 35
<212> TYPE: PRT
<213> ORGANISM: Hepatitis B virus

<400> SEQUENCE: 29

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly
        35
```

<210> SEQ ID NO 30
<211> LENGTH: 35
<212> TYPE: PRT
<213> ORGANISM: Hepatitis B virus

<400> SEQUENCE: 30

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly
        35

<210> SEQ ID NO 31
<211> LENGTH: 35
<212> TYPE: PRT
<213> ORGANISM: Hepatitis B virus

<400> SEQUENCE: 31

Met Ala Ala Arg Leu Cys Cys Gln Leu Asp Pro Thr Arg Asp Val Leu
1               5                   10                  15

Cys Leu Arg Pro Val Gly Ala Glu Ser Arg Gly Arg Pro Val Ser Gly
            20                  25                  30

Pro Leu Gly
        35

<210> SEQ ID NO 32
<211> LENGTH: 35
<212> TYPE: PRT
<213> ORGANISM: Hepatitis B virus

<400> SEQUENCE: 32

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly
        35

<210> SEQ ID NO 33
<211> LENGTH: 35
<212> TYPE: PRT
<213> ORGANISM: Hepatitis B virus

<400> SEQUENCE: 33

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly
        35

<210> SEQ ID NO 34
<211> LENGTH: 35
<212> TYPE: PRT
<213> ORGANISM: Hepatitis B virus

```
<400> SEQUENCE: 34

Met Ala Ala Arg Leu Cys Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly
        35

<210> SEQ ID NO 35
<211> LENGTH: 35
<212> TYPE: PRT
<213> ORGANISM: Hepatitis B virus

<400> SEQUENCE: 35

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Val Ser Gly
            20                  25                  30

Ser Leu Gly
        35

<210> SEQ ID NO 36
<211> LENGTH: 35
<212> TYPE: PRT
<213> ORGANISM: Hepatitis B virus

<400> SEQUENCE: 36

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 37
<211> LENGTH: 35
<212> TYPE: PRT
<213> ORGANISM: Hepatitis B virus

<400> SEQUENCE: 37

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 38
<211> LENGTH: 35
<212> TYPE: PRT
<213> ORGANISM: Hepatitis B virus

<400> SEQUENCE: 38

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35
```

<210> SEQ ID NO 39
<211> LENGTH: 35
<212> TYPE: PRT
<213> ORGANISM: Hepatitis B virus

<400> SEQUENCE: 39

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 40
<211> LENGTH: 35
<212> TYPE: PRT
<213> ORGANISM: Hepatitis B virus

<400> SEQUENCE: 40

Met Ala Thr Arg Leu Cys Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly
        35

<210> SEQ ID NO 41
<211> LENGTH: 35
<212> TYPE: PRT
<213> ORGANISM: Hepatitis B virus

<400> SEQUENCE: 41

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 42
<211> LENGTH: 35
<212> TYPE: PRT
<213> ORGANISM: Hepatitis B virus

<400> SEQUENCE: 42

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Ser Leu Gly
        35

<210> SEQ ID NO 43
<211> LENGTH: 35
<212> TYPE: PRT
<213> ORGANISM: Hepatitis B virus

```
<400> SEQUENCE: 43

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Pro Gly
            20                  25                  30

Pro Leu Gly
        35

<210> SEQ ID NO 44
<211> LENGTH: 35
<212> TYPE: PRT
<213> ORGANISM: Hepatitis B virus

<400> SEQUENCE: 44

Met Ala Ala Arg Met Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 45
<211> LENGTH: 35
<212> TYPE: PRT
<213> ORGANISM: Hepatitis B virus

<400> SEQUENCE: 45

Met Ala Ala Arg Val Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 46
<211> LENGTH: 35
<212> TYPE: PRT
<213> ORGANISM: Hepatitis B virus

<400> SEQUENCE: 46

Met Ala Ala Arg Leu Tyr Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly
        35

<210> SEQ ID NO 47
<211> LENGTH: 35
<212> TYPE: PRT
<213> ORGANISM: Hepatitis B virus

<400> SEQUENCE: 47

Met Ala Ala Arg Leu Tyr Cys Gln Leu Asp Pro Ser Arg Asp Val Leu
1               5                   10                  15

Cys Leu Arg Pro Val Gly Ala Glu Ser Arg Gly Arg Pro Leu Ser Gly
            20                  25                  30

Pro Leu Gly
        35
```

<210> SEQ ID NO 48
<211> LENGTH: 35
<212> TYPE: PRT
<213> ORGANISM: Hepatitis B virus

<400> SEQUENCE: 48

Met Ala Ala Arg Leu Cys Cys Gln Leu Asp Pro Ser Arg Asp Val Leu
1               5                   10                  15

Cys Leu Arg Pro Val Ser Ala Glu Ser Ser Gly Arg Pro Leu Pro Gly
            20                  25                  30

Pro Phe Gly
        35

<210> SEQ ID NO 49
<211> LENGTH: 35
<212> TYPE: PRT
<213> ORGANISM: Hepatitis B virus

<400> SEQUENCE: 49

Met Ala Ala Arg Leu Cys Cys Gln Leu Asp Thr Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly
        35

<210> SEQ ID NO 50
<211> LENGTH: 35
<212> TYPE: PRT
<213> ORGANISM: Hepatitis B virus

<400> SEQUENCE: 50

Met Ala Ala Arg Met Cys Cys Lys Leu Asp Pro Ala Arg Asp Val Leu
1               5                   10                  15

Cys Leu Arg Pro Ile Gly Ala Glu Ser Arg Gly Arg Pro Leu Pro Gly
            20                  25                  30

Pro Leu Gly
        35

<210> SEQ ID NO 51
<211> LENGTH: 35
<212> TYPE: PRT
<213> ORGANISM: Hepatitis B virus

<400> SEQUENCE: 51

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Val Ser Gly
            20                  25                  30

Ser Leu Gly
        35

<210> SEQ ID NO 52
<211> LENGTH: 35
<212> TYPE: PRT
<213> ORGANISM: Hepatitis B virus

<400> SEQUENCE: 52

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Ser Leu Ser Gly
            20                  25                  30

Ser Leu Gly
        35

<210> SEQ ID NO 53
<211> LENGTH: 35
<212> TYPE: PRT
<213> ORGANISM: Hepatitis B virus

<400> SEQUENCE: 53

Met Ala Ala Arg Leu Cys Cys Gln Leu Asp Thr Ala Arg Asp Val Leu
1               5                   10                  15

Cys Leu Arg Pro Val Gly Ala Glu Ser Arg Gly Arg Pro Phe Ser Gly
            20                  25                  30

Ser Val Gly
        35

<210> SEQ ID NO 54
<211> LENGTH: 35
<212> TYPE: PRT
<213> ORGANISM: Hepatitis B virus

<400> SEQUENCE: 54

Met Ala Ala Arg Leu Cys Cys Gln Leu Asp Pro Ala Arg Asp Val Leu
1               5                   10                  15

Cys Leu Arg Pro Val Ser Ala Glu Ser Cys Gly Arg Pro Val Ser Gly
            20                  25                  30

Ser Leu Gly
        35

<210> SEQ ID NO 55
<211> LENGTH: 35
<212> TYPE: PRT
<213> ORGANISM: Hepatitis B virus

<400> SEQUENCE: 55

Met Ala Ala Arg Leu Cys Cys Gln Leu Asp Pro Ala Arg Asp Val Leu
1               5                   10                  15

Cys Leu Arg Pro Val Ser Ala Glu Ser Cys Gly Arg Pro Val Ser Gly
            20                  25                  30

Ser Leu Gly
        35

<210> SEQ ID NO 56
<211> LENGTH: 35
<212> TYPE: PRT
<213> ORGANISM: Hepatitis B virus

<400> SEQUENCE: 56

Met Ala Ala Arg Leu Tyr Cys Gln Leu Asp Ser Ser Arg Asp Val Leu
1               5                   10                  15

Cys Leu Arg Pro Val Gly Ala Glu Ser Arg Gly Arg Pro Phe Ser Gly
            20                  25                  30

Pro Leu Gly
        35

```
<210> SEQ ID NO 57
<211> LENGTH: 35
<212> TYPE: PRT
<213> ORGANISM: Hepatitis B virus

<400> SEQUENCE: 57

Met Ala Ala Arg Leu Tyr Cys Gln Leu Asp Ser Ser Arg Asp Val Leu
1               5                   10                  15

Cys Leu Arg Pro Val Gly Ala Glu Ser Arg Gly Arg Pro Leu Ala Gly
            20                  25                  30

Pro Leu Gly
        35

<210> SEQ ID NO 58
<211> LENGTH: 35
<212> TYPE: PRT
<213> ORGANISM: Hepatitis B virus

<400> SEQUENCE: 58

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Leu Ser Trp
            20                  25                  30

Ser Leu Gly
        35

<210> SEQ ID NO 59
<211> LENGTH: 35
<212> TYPE: PRT
<213> ORGANISM: Hepatitis B virus

<400> SEQUENCE: 59

Met Ala Ala Arg Leu Cys Cys Gln Leu Asp Pro Ala Arg Asp Val Leu
1               5                   10                  15

Cys Leu Arg Pro Val Ser Ala Glu Ser Cys Gly Arg Ser Val Ser Gly
            20                  25                  30

Ser Leu Gly
        35

<210> SEQ ID NO 60
<211> LENGTH: 34
<212> TYPE: PRT
<213> ORGANISM: Hepatitis B virus

<400> SEQUENCE: 60

Met Ala Ala Arg Leu Cys Cys Gln Leu Asp Thr Ser Arg Asp Val Leu
1               5                   10                  15

Cys Leu Arg Pro Val Gly Ala Glu Ser Cys Gly Arg Pro Phe Ser Gly
            20                  25                  30

Pro Leu

<210> SEQ ID NO 61
<211> LENGTH: 35
<212> TYPE: PRT
<213> ORGANISM: Hepatitis B virus
```

<400> SEQUENCE: 61

Met Ala Ala Arg Leu Cys Cys Gln Leu Asp Pro Ala Arg Asp Val Leu
1               5                   10                  15

Cys Leu Arg Pro Val Gly Ala Glu Ser Ser Gly Arg Thr Leu Pro Gly
            20                  25                  30

Ser Leu Gly
        35

<210> SEQ ID NO 62
<211> LENGTH: 31
<212> TYPE: PRT
<213> ORGANISM: Hepatitis B virus

<400> SEQUENCE: 62

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Leu Ser
            20                  25                  30

<210> SEQ ID NO 63
<211> LENGTH: 31
<212> TYPE: PRT
<213> ORGANISM: Hepatitis B virus

<400> SEQUENCE: 63

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Leu Ser
            20                  25                  30

<210> SEQ ID NO 64
<211> LENGTH: 29
<212> TYPE: PRT
<213> ORGANISM: Hepatitis B virus

<400> SEQUENCE: 64

Met Ala Ala Arg Met Cys Cys Gln Leu Asp Pro Ser Gln Asp Val Leu
1               5                   10                  15

Cys Leu Arg Pro Val Gly Ala Glu Ser Arg Gly Arg Pro
            20                  25

<210> SEQ ID NO 65
<211> LENGTH: 32
<212> TYPE: PRT
<213> ORGANISM: Hepatitis B virus

<400> SEQUENCE: 65

Met Ala Ala Arg Leu Cys Cys Gln Leu Asp Pro Ala Arg Asp Val Leu
1               5                   10                  15

Cys Leu Arg Pro Val Gly Ala Glu Pro Cys Arg Arg Pro Val Ser Gly
            20                  25                  30

<210> SEQ ID NO 66
<211> LENGTH: 35
<212> TYPE: PRT
<213> ORGANISM: Hepatitis B virus

```
<400> SEQUENCE: 66

Met Ala Ala Arg Leu Tyr Cys Gln Leu Asp Ser Ser Arg Asn Val Leu
1               5                   10                  15

Cys Leu Arg Pro Val Gly Ala Glu Ser Cys Gly Arg Pro Leu Ser Gly
            20                  25                  30

Pro Val Gly
        35

<210> SEQ ID NO 67
<211> LENGTH: 26
<212> TYPE: PRT
<213> ORGANISM: Homo sapiens

<400> SEQUENCE: 67

Asp Gly Val Asn Val Glu Met His Leu Lys Gln Ile Glu Ile Lys Lys
1               5                   10                  15

Phe Lys Tyr Gly Ile Glu Glu His Gly Lys
            20                  25

<210> SEQ ID NO 68
<211> LENGTH: 26
<212> TYPE: PRT
<213> ORGANISM: Homo sapiens

<400> SEQUENCE: 68

Asp Gly Ala Asn Val Asp Met His Leu Lys Gln Ile Glu Ile Lys Lys
1               5                   10                  15

Phe Lys Tyr Gly Ile Glu Glu His Gly Lys
            20                  25

<210> SEQ ID NO 69
<211> LENGTH: 21
<212> TYPE: PRT
<213> ORGANISM: Homo sapiens

<400> SEQUENCE: 69

Arg Pro Ser Ser Arg Ala Ser Ser Arg Ala Ser Ser Arg Pro Arg Pro
1               5                   10                  15

Asp Asp Leu Glu Ile
            20

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 71
<211> LENGTH: 9
<212> TYPE: PRT
<213> ORGANISM: Rattus sp.
```

-continued

```
<400> SEQUENCE: 71

Arg Pro Arg Pro Asp Asp Leu Glu Ile
1               5

<210> SEQ ID NO 72
<211> LENGTH: 10
<212> TYPE: PRT
<213> ORGANISM: Homo sapiens

<400> SEQUENCE: 72

Ser Arg Pro Arg Pro Asp Asp Leu Glu Ile
1               5                   10

<210> SEQ ID NO 73
<211> LENGTH: 15
<212> TYPE: DNA
<213> ORGANISM: Hepatitis B virus

<400> SEQUENCE: 73
ctttgtctac gtccc                                                        15

<210> SEQ ID NO 74
<211> LENGTH: 21
<212> TYPE: DNA
<213> ORGANISM: Hepatitis B virus

<400> SEQUENCE: 74
ctttgtctac gtcccgtcgg c                                                 21

<210> SEQ ID NO 75
<211> LENGTH: 27
<212> TYPE: DNA
<213> ORGANISM: Hepatitis B virus

<400> SEQUENCE: 75
ctttgtctac gtcccgtcgg cgctgaa                                           27

<210> SEQ ID NO 76
<211> LENGTH: 33
<212> TYPE: DNA
<213> ORGANISM: Hepatitis B virus

<400> SEQUENCE: 76
ctttgtctac gtcccgtcgg cgctgaatcc cgc                                    33

<210> SEQ ID NO 77
<211> LENGTH: 60
<212> TYPE: DNA
<213> ORGANISM: Hepatitis B virus

<400> SEQUENCE: 77
ctttgtctac gtcccgtcgg cgctgaatcc cgcggacgac ccgtctcggg gccgtttggg       60

<210> SEQ ID NO 78
<211> LENGTH: 15
<212> TYPE: DNA
<213> ORGANISM: Hepatitis B virus

<400> SEQUENCE: 78
gtcctttgtc tacgt                                                        15
```

```
<210> SEQ ID NO 79
<211> LENGTH: 12
<212> TYPE: DNA
<213> ORGANISM: Hepatitis B virus

<400> SEQUENCE: 79
ctttgtctac gt                                                         12

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Gly Arg Lys Lys Arg Arg Gln Arg Arg Lys Gln Ile Glu Ile
1               5                   10                  15

Lys Lys Phe Lys
            20

<210> SEQ ID NO 81
<211> LENGTH: 12
<212> TYPE: PRT
<213> ORGANISM: Homo sapiens

<400> SEQUENCE: 81

Val Asp Cys Phe Leu Ser Arg Pro Thr Glu Lys Thr
1               5                   10
```